(12) United States Patent
Ovokaitys et al.

(10) Patent No.: US 8,173,632 B2
(45) Date of Patent: May 8, 2012

(54) PROCESS FOR THE MODIFICATION OF THE SOLID STATE OF A COMPOUND AND CO-AMORPHOUS COMPOSITIONS PRODUCED WITH SAME

(75) Inventors: Todd F. Ovokaitys, Carlsbad, CA (US); John Scott Strachan, Edinburgh (GB)

(73) Assignee: Todd F. Ovokaitys, Carlsbad, CA (US)

( * ) Notice: Subject to any disclaimer, the term of this patent is extended or adjusted under 35 U.S.C. 154(b) by 758 days.

(21) Appl. No.: 12/252,458

(22) Filed: Oct. 16, 2008

(65) Prior Publication Data
US 2009/0131376 A1 May 21, 2009

Related U.S. Application Data

(60) Provisional application No. 60/999,445, filed on Oct. 17, 2007, provisional application No. 60/999,462, filed on Oct. 17, 2007, provisional application No. 60/999,483, filed on Oct. 17, 2007.

(51) Int. Cl.
*A61K 31/396* (2006.01)
*A61K 31/425* (2006.01)
*A61K 31/40* (2006.01)
*A61K 31/35* (2006.01)
*A61K 31/215* (2006.01)

(52) U.S. Cl. .......... 514/210.02; 514/370; 514/420; 514/460; 514/529

(58) Field of Classification Search ............ None
See application file for complete search history.

(56) References Cited

U.S. PATENT DOCUMENTS

| 6,064,500 | A | 5/2000 | Strachan | |
|---|---|---|---|---|
| 6,763,607 | B2 * | 7/2004 | Beyerinck et al. | 34/372 |
| 6,811,564 | B1 | 11/2004 | Strachan | |
| 2002/0034546 | A1 * | 3/2002 | Ullah et al. | 424/475 |
| 2003/0163931 | A1 | 9/2003 | Beyerinck et al. | |
| 2004/0239044 | A1 | 12/2004 | Blatter et al. | |
| 2007/0003615 | A1 * | 1/2007 | Jenkins et al. | 424/464 |

FOREIGN PATENT DOCUMENTS

| WO | 01/00563 | 1/2001 |
|---|---|---|
| WO | 02/059087 | 8/2002 |
| WO | 03/020291 | 3/2003 |
| WO | 2004/071435 | 8/2004 |
| WO | 2007/100614 | 9/2007 |

OTHER PUBLICATIONS

Rouhi, Chemical and Engineering News, The Right Stuff, 2003, 81(8), pp. 32-35.*
Fukuoka et al, Chemical and Pharmaceutical Bulletin, Glassy State of Pharmeceuticals. III. Therrnal Properties and Stability of Glassy Pharmaceuticals and Their Binary Glass Systems, 1989, 37(4), pp. 1047-1050.*
International Search Report and Written Opinion dated Nov. 3, 2008 for PCT/US08/80095.
Johari et al., *Physical Chemistry Chemical Physics*, 2000, 2, 5479-5484.
www.CEN-online.org, "Second Aspirin Polymorph Found", Nov. 21, 2005.
Eurasian Search Report dated May 30, 2011.
Duddu, S.P. et al, "Importance of glass transition temperature in accelerated stability testing of amorphous solids: case study using a lyophilized aspirin formulation", Journal of Pharmaceutical Sciences, American Pharmaceutical Association, Washington, U.S., vol. 85, No. 3, Mar. 1, 1996, pp. 345-347.
Extended European Search Report (Supplementary European Search Report and European Search Opinion) for corresponding European Application No. 08839613.0, mailed Feb. 24, 2012.

* cited by examiner

*Primary Examiner* — Paul A Zucker
(74) *Attorney, Agent, or Firm* — Kenyon & Kenyon LLP

(57) ABSTRACT

The invention provides a process for preparing non-crystalline organic compositions and non-crystalline, co-amorphous blends of organic compounds.

32 Claims, 42 Drawing Sheets

PROCESS FOR THE MODIFICATION OF THE SOLID STATE OF A COMPOUND AND CO-AMORPHOUS COMPOSITIONS PRODUCED WITH SAME

RELATED APPLICATIONS

This application claims benefit of U.S. Provisional Patent Applications Nos. 60/999,445, 60/999,462, and 60/999,483, all filed Oct. 17, 2007, the contents of which are incorporated herein in their entirety. This application is also related to U.S. patent application Ser. No. 12/252,447, titled ROOM TEMPERATURE STABLE NON-CRYSTALLINE ASPIRIN AND METHOD FOR THE PREPARATION THEREOF, filed on even date herewith, the contents of which are also incorporated herein in their entirety.

FIELD OF THE INVENTION

The present invention is directed to a process for modifying the solid state of compounds and to compounds modified with the process of the invention. In particular, the invention is directed a process for the preparation of non-crystalline and crystalline forms of chemical compounds, such as pharmaceutical and nutrient compounds, and to non-crystalline and crystalline compounds prepared with the method of the invention.

BACKGROUND

Many pharmaceutical solids can exist in different physical forms. Polymorphism is often defined as the ability of a compound to exist in at least two crystalline phases, where each crystalline phase has a different arrangement and/or conformation of molecules in a crystalline lattice. Non-crystalline solids consist of disordered arrangements of molecules, and do not possess a distinguishable crystal lattice.

The non-crystalline and different polymorphic forms of a pharmaceutical solid differ in internal solid state structure, and, thus, typically have different chemical and physical properties, including packing, thermodynamic, spectroscopic, kinetic, interfacial, solubility, reactivity, and mechanical properties. Those properties can have a direct impact on the quality and/or performance of a drug product, including its stability, dissolution rate, and bioavailability.

For example, until recently, the original crystalline form of aspirin, known as Form I, was the only known crystalline form of aspirin and the only form of aspirin that is stable at room temperature. However, as reported in *Chemical & Engineering News*, Nov. 21, 2005, Zaworotko et al., *J. Am. Chem. Soc.*, 2005, 127, 16802, reported the synthesis of a second polymorphic form of aspirin. Aspirin Form II is kinetically stable at 100 K (−173° C.), but converts back to Form I at ambient conditions.

Amorphous glass aspirin has also been formed. However, except, possibly, for some microscopic residues, amorphous aspirin has been produced only at very low temperatures. Above the glass transition temperature of about 243 Kelvin (−30° C.), amorphous aspirin converts rapidly to the crystalline Form I. Thus, all prior art forms of aspirin convert to Form I at room temperature. As a result of the low temperature required to create and maintain the amorphous form, there has been essentially no practical application of the amorphous solid state form.

Johari et al., *Physical Chemistry Chemical Physics*, 2000, 2, 5479-5484, also report the vitrification of aspirin by melting and cooling and by ball-milling at ambient temperature to form a vitreous or supercooled viscous liquid aspirin that is stable against crystallization for several days at 298K. The viscous liquid was found to flow slowly when tilted in a container, but did not crystallize for four to five days at 298K. The vitreous aspirin samples did ultimately undergo complete crystallization, which was accelerated when the samples were kept at about 340K.

Johari et al. report that the vitreous state has a higher energy state than the crystal state with a lower frequency of its phonon modes and a greater anharmonicity that make absorption and assimilation directly from the solid state more effective and efficient. In its bulk form, the vitreous aspirin is reported to dissolve more slowly than the same mass of finely powdered crystals of aspirin. As is well known in the art, a bulk sample of a substance has a significantly smaller surface area than finely powdered crystals. That makes the dissolution of the bulk form much more difficult, accounting for the slower dissolution rate of the bulk vitreous aspirin reported by Johari et al.

The most stable form of a drug substance is often used in a formulation, as it has the lowest potential for conversion from one form to another. However, a different form that is sufficiently stable under the predicted storage conditions can be chosen to enhance the bioavailability of the drug product. The other form may be a metastable polymorph, i.e., a polymorphic form that is less stable than the most stable form, but typically does not convert to a different form during normal storage, or a non-crystalline form. A non-crystalline form lacks the regular molecular organization of a crystalline form, and does not need to lose crystal structure during dissolution in gastric juices. Therefore, non-crystalline forms often dissolve more quickly, and have a greater bioavailability than crystalline forms.

Although a non-crystalline form may be desirable for a pharmaceutical composition, the preparation of non-crystalline forms on an industrial scale is often problematic. Processes for the preparation of non-crystalline forms of pharmaceutical compositions include solidification of melt, reduction of particle size, spray-drying, lyophilization (also known as freeze-drying), removal of a solvent from crystalline structure, precipitation of acids and bases by a change in pH, and other such techniques.

Such processes are often unsuitable or impractical for production on an industrial scale. For example, to obtain a non-crystalline active pharmaceutical ingredient by solidification of melt, the active pharmaceutical ingredient has to be heated beyond its melting point, requiring the expenditure of a significant amount of energy, particularly when the active pharmaceutical ingredient has a high specific heat and/or heat of fusion. In addition, the melting the pharmaceutical composition may chemically alter the active pharmaceutical ingredient. Some materials also decompose before melting, and, thus, solidification of melt cannot be used.

Lyophilization is quite expensive on a large scale, and generally has limited capacity. Where the solvent is organic, lyophilization often presents a disposal and/or fire hazard.

Spray-drying requires dispersing a liquid solution in a volume of a heated gas sufficient to evaporate the solvent, leaving particulates of the solute. The heated gas is typically hot air or nitrogen. Spray drying, is typically limited to aqueous solutions unless special expensive safety measures are taken. In addition, contact of the pharmaceutical composition with the heated gas can result in degradation of the composition.

The form of a solid chemical compound, whether non-crystalline or crystalline, affects many of the properties of the compound that are important to the formulation of a pharmaceutical composition. The flowability of a milled solid is particularly important in the preparation of a pharmaceutical product, as flowability affects the ease with which a pharmaceutical composition is handled during processing. When a powdered compound does not flow freely, it may be necessary to use one or more glidants in a tablet or capsule formulation. Glidants used in pharmaceutical compositions include colloidal silicon dioxide, talc, starch, or tribasic calcium phosphate.

Another important property of a pharmaceutical compound that may depend on crystallinity is its dissolution rate in an aqueous fluid. The rate of dissolution of an active ingredient in a patient's stomach fluid can have therapeutic consequences, as the dissolution rate imposes an upper limit on the rate at which an orally-administered active ingredient can reach the bloodstream of a patient. The solid state form of a compound may also affect its behavior on compaction and its storage stability.

The discovery of new non-crystalline and crystalline forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic.

SUMMARY OF THE INVENTION

The invention is directed to non-crystalline compositions, co-amorphous pharmaceutical compositions, and process for the preparation of the compositions of the invention. Preferably, the non-crystalline composition is a co-amorphous pharmaceutical composition, comprising a non-crystalline, co-amorphous blend of at least two pharmaceutical compounds. More preferably, the pharmaceutical compounds are selected from the group consisting of aspirin, ezetimibe, simvastatin, atorvastatin free acid, atorvastatin calcium, and rosuvastatin calcium. Most preferably, the co-amorphous pharmaceutical composition is selected from the group consisting of ezetimibe/simvastatin, ezetimibe/atorvastatin calcium, ezetimibe/atorvastatin free acid, ezetimibe/rosuvastatin calcium, ezetimibe/simvastatin/aspirin, ezetimibe/atorvastatin calcium/aspirin, ezetimibe/atorvastatin free acid/aspirin, and ezetimibe/rosuvastatin calcium/aspirin, as well as co-amorphous compositions comprising at least one statin and aspirin. Co-amorphous statin/aspirin compositions include, but are not limited to, atorvastatin free acid/aspirin, atorvastatin calcium/aspirin, simvastatin/aspirin, and rosuvastatin calcium/aspirin. Preferably, the co-amorphous pharmaceutical composition is homogeneous.

The invention provides a process for preparing a non-crystalline composition comprising at least one organic compound. The process comprises applying laser radiation from at least two different lasers to a solution of the at least one organic compound in a solvent, and evaporating the solvent. Preferably, the laser radiation is pulsed, having pulses with an effective average pulse length of no more than about $10^{-9}$ seconds, and the pulses of laser radiation from each laser has a different wavelength. Preferably, the at least one organic compound is a pharmaceutical composition. More preferably, the at least one organic compound is selected from the group consisting of aspirin, ezetimibe, simvastatin, atorvastatin free acid, atorvastatin calcium, rosuvastatin calcium, and mixtures thereof.

Preferably, the laser radiation used in the process comprises laser emissions modified with a Strachan Device, where the Strachan Device comprises a first diffraction grating and a second diffraction grating and a refractive element positioned between the first and second diffraction gratings. Preferably, the lasers used with the Strachan Device are diode lasers.

The process of the invention, preferably comprises obtaining a solution of the at least one organic compound in a solvent, placing the solution of the at least one organic compound in a covered container, applying the laser radiation to the solution, and evaporating at least a portion of the solvent while applying the laser radiation, thereby forming the non-crystalline composition.

More preferably, the process for preparing a non-crystalline composition of the invention comprises passing laser radiation through a Strachan Device, the Strachan Device comprising a first diffraction grating and a second diffraction grating and a refractive element positioned between the first and second diffraction gratings, canceling a portion of the laser radiation by destructive interference, and producing pulses of laser radiation by constructive interference. The laser radiation passed through the Strachan Device is applied to a solution comprising at least one pharmaceutical composition in a solvent, and the solvent is evaporated.

DETAILED DESCRIPTION OF THE INVENTION

Figure 1:
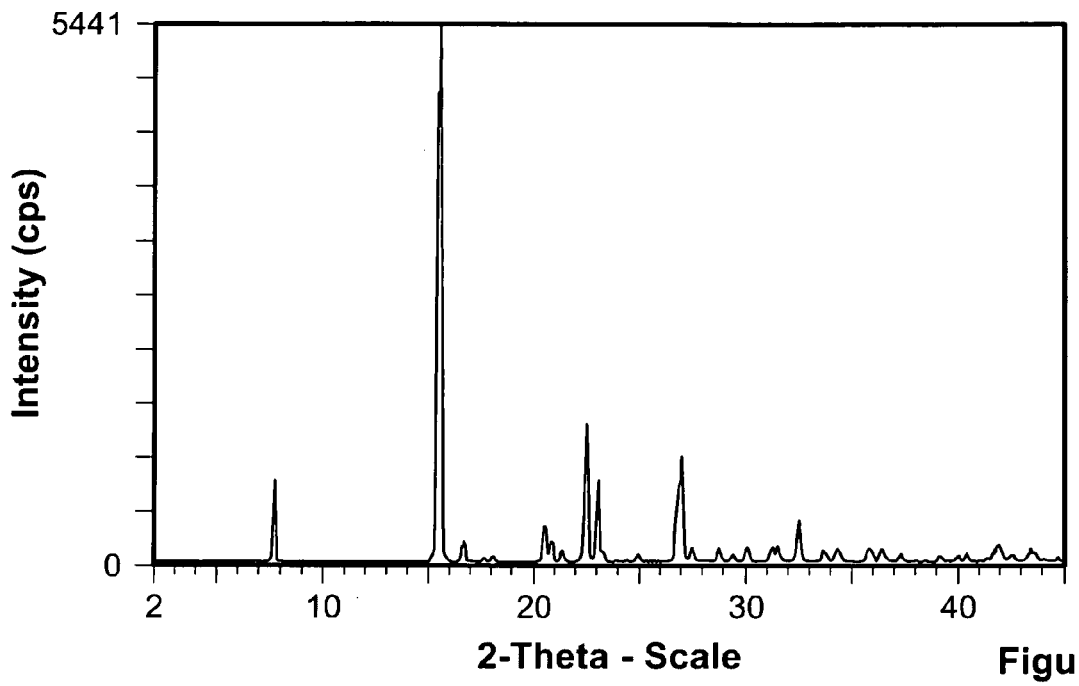
FIG. 1 illustrates the Powder X-ray Diffraction (PXRD) pattern of a crystalline aspirin sample.

As used herein, with regard to the solid state of a compound, the term "non-crystalline" refers to any solid form of the compound that, upon a powder X-ray diffraction (PXRD) analysis, provides a PXRD pattern that is substantially free of any PXRD peaks that are typical of a PXRD pattern of a crystalline form of the compound. Non-crystalline compounds are typically, but need not be, amorphous.

As also used herein, the term "co-amorphous" refers to a non-crystalline blend of two or more non-crystalline compounds, where the co-amorphous blend is produced from a solution of the two or more compounds with the process of the invention. A co-amorphous composition of three non-crystalline compounds may also be referred to as "tri-amorphous." The compounds in a co-amorphous composition are typically intimately intermixed, and are preferably substantially homogeneous. Co-amorphous compositions prepared with the process of the invention are preferably considered solid solutions.

As discussed above, a non-crystalline form of a compound has a PXRD pattern that is free of the characteristic peaks of a crystalline form of the compound. As a result, the characteristic PXRD pattern of the crystalline form cannot be used to confirm the chemical identity of the non-crystalline form. In some cases the PXRD pattern of the non-crystalline form is known, and may be used to confirm the chemical identity. The process of the invention is used to convert a crystalline form of a compound to a non-crystalline or new crystalline form of the same compound. Thus, a method is typically required to confirm that the chemical identity of the converted compound remained unchanged. That is, a confirmation that no chemical reaction occurred during the process of the invention is required. A Fourier Transform Infrared (FTIR) spectroscopy analysis of a non-crystalline composition provides that confirmation.

An FTIR analysis of a non-crystalline solid compound typically results in an FTIR pattern in which the absorption bands may be broadened slightly compared to the FTIR pattern obtained from a crystalline form of the compound. Infrared spectra of crystalline materials typically exhibit sharper and/or higher resolution absorption bands than the non-crystalline form. Some shifting of bands in the infrared spectrum may also be observed, as a result of changes in form between crystalline materials and the non-crystalline form of the same compound. However, the changes in the FTIR spectra between the non-crystalline and crystalline forms are sufficiently small to allow confirmation of the identity of the non-crystalline form of the compound by comparing the FTIR spectra of the crystalline and non-crystalline forms.

The present invention is directed to stable crystalline and non-crystalline forms of organic compositions, particularly pharmaceutical compositions, that are stable at room temperature and to processes for producing the stable crystalline and non-crystalline forms with the process of the invention. The crystalline and non-crystalline forms of pharmaceutical compositions of the invention are stable at a relative humidity of about 30 to about 40 percent and a temperature of about 20° to 30° C. for at least about 24 hours, preferably, for at least about 30 days, more preferably, for at least three months, and, most preferably, for at least about six months. Samples of non-crystalline forms of the pharmaceutical compositions of the invention have remained stable and non-crystalline at a relative humidity of about 30 to about 40 percent and a temperature of about 20° to 30° C. for at least about two years.

Non-crystalline compositions prepared with the process of the invention include, but are not limited to, non-crystalline compositions comprising aspirin, ezetimibe, simvastatin, atorvastatin free acid, atorvastatin calcium, rosuvastatin calcium, and co-amorphous compositions of those compounds. Non-crystalline co-amorphous compositions of the invention prepared with the process of the invention include, but are not limited to, ezetimibe/simvastatin, ezetimibe/atorvastatin calcium, ezetimibe/atorvastatin free acid, ezetimibe/rosuvastatin calcium, ezetimibe/simvastatin/aspirin, ezetimibe/atorvastatin calcium/aspirin, ezetimibe/atorvastatin free acid/aspirin, and ezetimibe/rosuvastatin calcium/aspirin, as well as co-amorphous compositions comprising at least one statin and aspirin. Co-amorphous statin/aspirin compositions include, but are not limited to, atorvastatin free acid/aspirin, atorvastatin calcium/aspirin, simvastatin/aspirin, and rosuvastatin calcium/aspirin. The weight ratio of the pharmaceutical compositions in the treated composition is preferably adjusted to provide the desired dosage of each pharmaceutical composition.

Without being bound by theory, it is believed that the non-crystalline form of a compound has a higher free energy in the intermolecular lattice than any of the crystallized forms of the compound. This imparts a higher solubility in water to the non-crystalline form that may be about 2 to 8 times higher than that of the crystalline form, where the non-crystalline and crystalline forms have similar particle sizes. Such an increase in solubility can translate to faster dissolution, absorption, and clinical action, as well as significantly higher bioavailability.

Thus, the non-crystalline pharmaceutical compositions of the invention provide a more rapid dissolution rate than crystalline forms of the same compositions under conditions following oral ingestion or trans-mucosal delivery, such as sublingual, and provide higher solubility and bioavailability. Accordingly, the non-crystalline pharmaceutical compositions of the invention, which are stable for extended periods of time at a relative humidity of about 30 to about 40 percent and a temperature of from about 20° to about 30° C., should have clinical and other advantages over the crystalline forms.

It should be noted that significantly high molar ratios of aspirin to statins have been readily achieved with the process of the invention. Without being bound by theory, it is believed that the greater aqueous solubility of aspirin compared to that of statins in the co-amorphous statin/aspirin compositions of the invention provide a significantly increased relative aqueous solubility of the statin.

A crystalline form of a compound has a PXRD pattern with characteristic peaks at particular reflection angles of the X-ray beam, measured in degrees 2θ. Typically, the resolution of a measurement is on the order of ±0.2° 2θ. The reflections are the result of the regular arrangement of the molecules in the crystal. In contrast, a partially non-crystalline sample of a compound has a PXRD pattern with substantially blunted or reduced peaks, and a sample of a purely non-crystalline compound has a PXRD pattern that is typically free of any characteristic peaks. The molecules are arranged randomly in a non-crystalline compound, and, thus, the reflection peaks are not observed in the PXRD pattern. Changes in intensity that occur over broad ranges may be observed in some non-crystalline compounds along with baseline noise.

For example, a powder X-ray diffraction (PXRD) analysis of crystalline aspirin and the non-crystalline aspirin prepared with the process of the invention demonstrates the difference in the arrangement of molecules in crystalline and non-crystalline forms. A typical PXRD pattern for commercially available crystalline aspirin is illustrated in FIG. 1. The PXRD pattern of FIG. 1 has a number of peaks, characteristic of crystalline aspirin.

Figure 3:
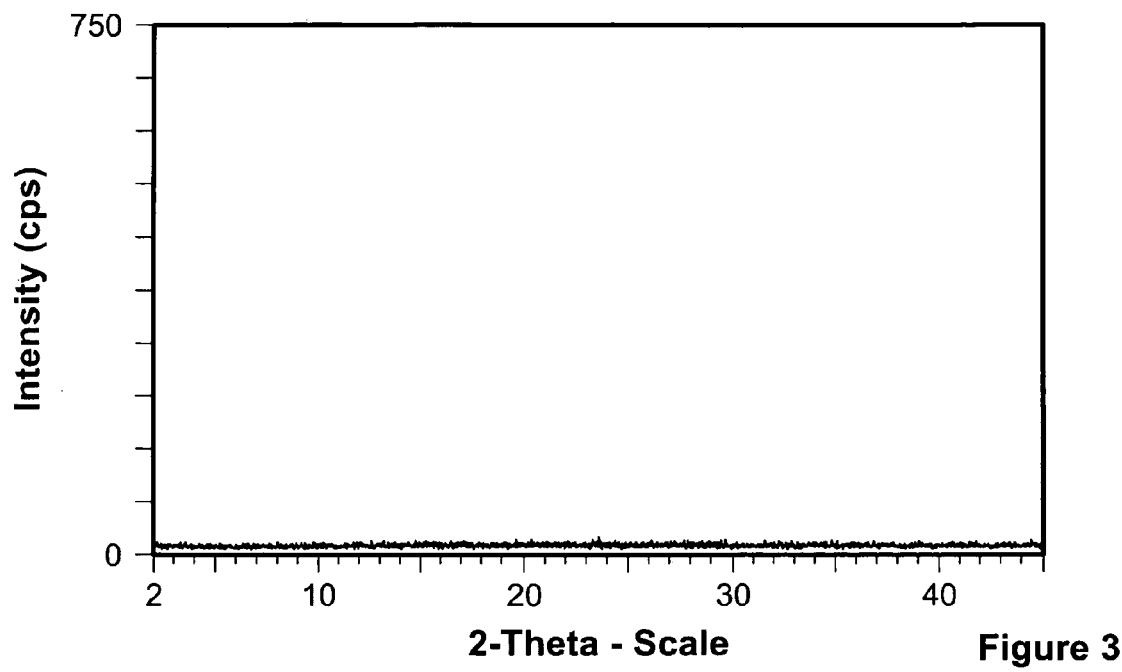
FIG. 3 illustrates the PXRD pattern of a sample of aspirin treated with the process of the invention.

In contrast, FIG. 3 illustrates the PXRD pattern of non-crystalline aspirin prepared with the process of the invention. The PXRD pattern of the non-crystalline aspirin is in marked contrast to the highly crystalline pattern shown in FIG. 1 for the crystalline aspirin. The high intensity PXRD peaks of the crystalline aspirin are substantially absent, indicating that, at most, only very short range ordering is present in the non-crystalline aspirin of the invention. It is important to note that the resolution of the PXRD pattern of FIG. 1 is more than seven times greater than the resolution of the pattern illustrated in FIG. 3. Therefore, any of the peaks observed in the PXRD pattern of the crystalline aspirin in FIG. 1 that may be present in the PXRD pattern of the non-crystalline aspirin in FIG. 3 effectively have intensities no greater than the baseline noise in FIG. 1. This is clear evidence that the aspirin analyzed by PXRD, as illustrated in FIG. 3, is substantially pure non-crystalline aspirin. Ordering of the aspirin molecules in the sample that would result in PXRD peaks is substantially absent.

Given the strong thermodynamic tendency of some compounds, such as aspirin, to crystallize at room temperature, very short range microcrystalline formations may be present in a non-crystalline composition, such as the non-crystalline aspirin illustrated in FIG. 3. However, the room temperature PXRD patterns obtained for non-crystalline compositions prepared with the process of the invention suggests that, at most, microcrystalline structures, having very short range ordering of not more than a few molecules, may be scattered randomly throughout the composition. Substantially the entire sample is made up of a continuous phase of complete randomization typical of a true glass that may contain a few, random microcrystalline structures, having very short range ordering. The physical and chemical properties of the non-crystalline composition prepared with the process of the invention are believed to be substantially the same as those that would be expected of a pure glass. The arrangement of molecules is substantially random, likely malting the non-crystalline composition more soluble than the crystalline form.

As with the disappearance of the characteristic reflection peaks of a PXRD pattern, the Fourier Transform Infrared (FTIR) spectroscopy absorption bands are typically broadened as the amount of the non-crystalline form of the compound increases in the sample. This provides additional evidence of the presence of the non-crystalline form. Infrared spectra of crystalline materials typically exhibit sharper or better resolved absorption bands than the non-crystalline form. Some bands in an infrared spectrum may also be shifted somewhat because of changes in form between crystalline materials and the non-crystalline form of the same compound.

Figure 2:
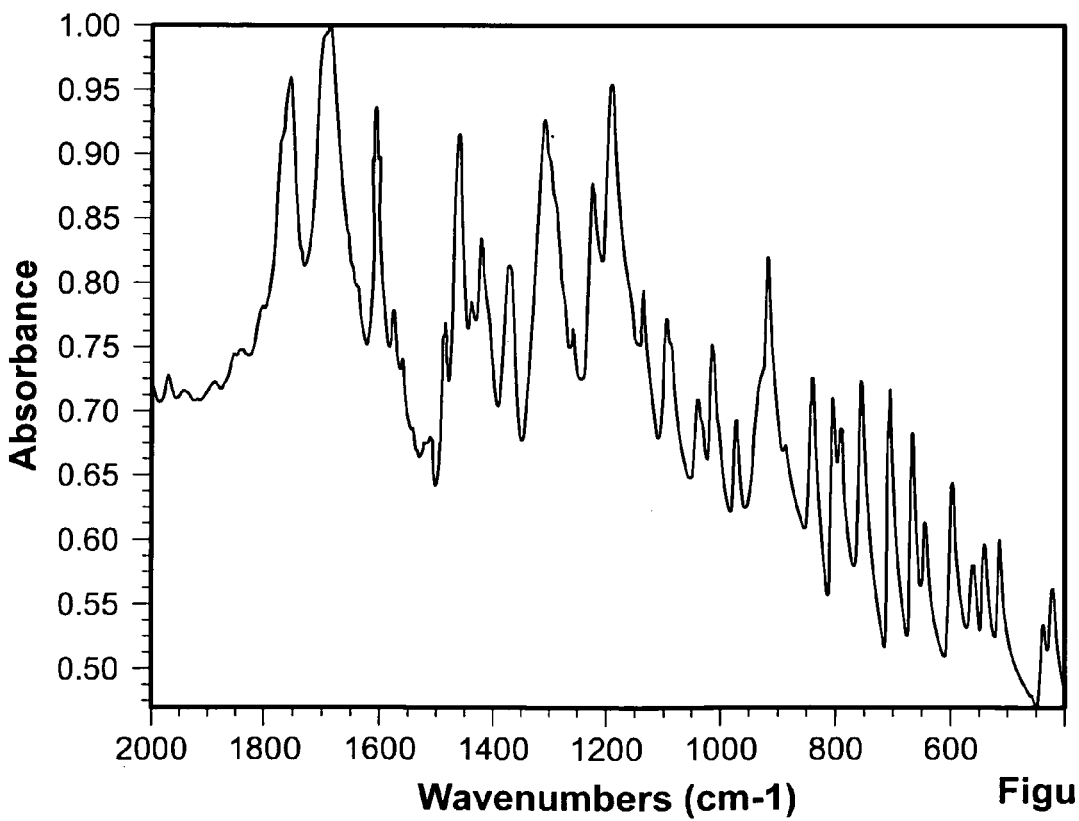
FIG. 2 illustrates a Fourier Transform Infrared (FTIR) spectrum of the crystalline aspirin sample.
Figure 4:
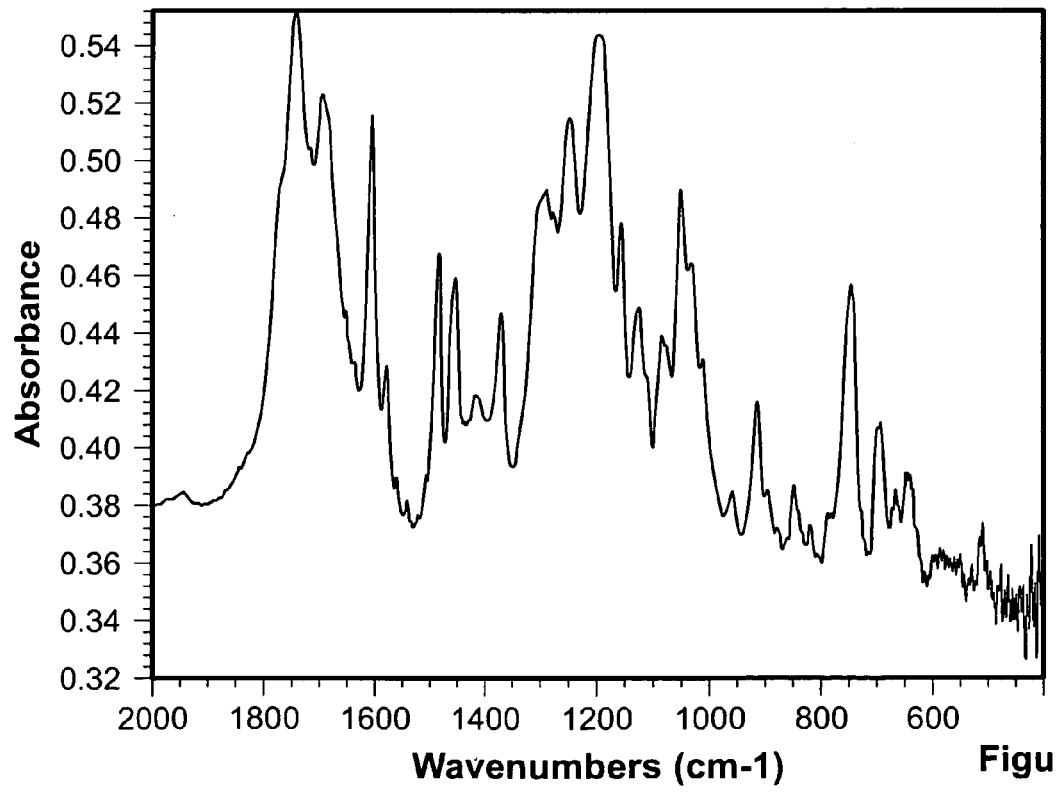
FIG. 4 illustrates the FTIR spectrum of the non-crystalline aspirin.

For example, the results of FTIR analyses of crystalline and non-crystalline aspirin are illustrated in FIGS. 2 and 4, respectively. The aspirin samples are those analyzed by PXRD in FIGS. 1 and 3. The absorption peaks of the FTIR pattern of the crystalline aspirin, illustrated in FIG. 2 are relatively well defined. In contrast, the FTIR pattern of the non-crystalline aspirin illustrated in FIG. 4 provides relatively broad absorption bands. A comparison of the FTIR spectra of crystalline aspirin and the non-crystalline aspirin of the invention demonstrates that the two samples are the same chemical entity. However, the broadening of the FTIR peaks of the sample analyzed in FIG. 4 is consistent with the non-crystalline form of the compound.

The difference in the crystal structure of prior art crystalline compositions and the non-crystalline compositions of the invention is also observed in polarized light microscopy (PLM) photomicrographs of the crystalline and non-crystalline forms. In polarized light microscopy, crystalline compositions produce birefringence. Birefringence appears in anisotropic materials in which the molecules in the crystalline form are arranged in a highly ordered pattern that is absent in the non-crystalline form. As a result, polarized light microscopy photomicrographs of crystalline compositions shows a high degree of birefringence that is not observed in purely non-crystalline compositions, which lacks the ordered arrangement of molecules found in the crystalline form.

For example, birefringence is clearly visible throughout a highly crystalline sample in a polarized light microscopy photomicrograph of the crystalline aspirin, exhibiting high order white interference colors. In contrast, birefringence is not observed in polarized light microscopy photomicrographs of pure isotropic non-crystalline aspirin particles of the invention. The absence of birefringence is evidence of the non-crystalline compositions of the invention. As noted above, birefringence requires the ordered arrangement of molecules that is found in the crystalline form, but is not present in the non-crystalline form.

The non-crystalline compositions of the invention are produced by exposing a solution of one or more chemical compounds to of laser light of different wavelengths from at least two sources, and evaporating the solvent. The laser light may be applied simultaneously or in alternating sequences. The compounds are preferably pharmaceutical compositions.

Preferably, the laser radiation is pulsed at a relatively high pulse repetition rate, having an effective pulse length no greater than the picosecond range ($10^{-12}$ to $10^{-9}$ second), and may be in the femtosecond range ($10^{-15}$ to $10^{-12}$ second) or the sub-femtosecond range ($<10^{-15}$ second). One of the lasers preferably has an emission centered in the lower half of the visible spectrum, i.e., between about 400 and about 550 nm, preferably, in the near ultraviolet (UV) to blue range, more preferably, at a wavelength from about 400 to about 470 nm. The other laser preferably has an emission centered in the upper half of the visible spectrum, i.e., between about 550 and about 700 nm, preferably, in the red to near infrared (IR), more preferably at a wavelength of from about 620 to about 680 nm. Using two lasers having emissions centered at similar wavelengths, i.e., two short wavelength lasers, two long wavelength lasers, or two lasers with emissions centered near 550 nm, may be useful in some applications. However, good results have been obtained with one laser having a center wavelength of from about 400 to about 470 nm and a second laser having a center wavelength of from about 620 to about 680 nm.

Without being bound by theory, it is believed that the output bandwidth of the lasers is broadened by the short effective pulse length. This follows from the Uncertainty Principle. As a result, the short pulses of laser light are believed to provide photons that interact with multiple vibrational and/or electronic states in the process of the invention to provide the non-crystalline forms. As a result, lasers having emissions that correspond to specific absorption bands of the treated compounds are not required.

Preferably, the ultra-short laser pulses are produced by modifying the output of the lasers to generate sparse nodes of constructive interference of electromagnetic (EM) waves, as disclosed by U.S. Pat. Nos. 6,064,500 and 6,811,564 to Strachan, the disclosures of which are incorporated herein in their entirety by reference. As used herein, the term "Strachan Device" refers to a device of the type disclosed by Strachan in those patents. A Strachan Device, as defined in the '500 and '564 patents, and as used herein, comprises a first diffraction grating and a second diffraction grating and a refractive element positioned between the first and second diffraction gratings. When a laser beam, either continuous or pulsed, is passed sequentially through the first diffraction grating, the refractive element, and the second diffraction grating of a Strachan Device, at least a portion of the beam is substantially canceled by destructive interference. The interaction of light beams that pass through the Strachan Device results in destructive interference that substantially cancels the beams as they exit the Strachan Device. The refractive element allows the cancellation to occur over a small percentage of the laser source rather than at a single critical wavelength.

Relatively sparse zones of constructive interference occur between the high and low frequency passes of the cancellation element in selected directions from the aperture. The sparse nodes of constructive interference occur only where the output of the Strachan Device results in constructive interference at a distance from the device. The constructive interference only occurs over ultra-short time periods, and, thus, results in ultra-short pulses of light. The pulses are believed to have effective pulse lengths of no more than about $10^{-9}$ seconds.

With a Strachan Device, fractional changes in the wavelength of the laser or relative amplitudes of wavelengths in the laser cause rapid translation in the location of these nodes, as, for example, fractional changes in current in a laser diode and fluctuations in junction temperature causing variations in the laser center frequency. As a result, a continuous laser beam is transformed into a string of extremely short duration pulses by the simple means of relatively small low frequency amplitude modulation. The amplitude modulation of diode lasers at a frequency of over 1 MHz is well within the skill of those skilled in the art. As a result, effective pulse lengths having a duration in the picosecond range are readily attainable, and femtosecond or sub-femtosecond pulses are attainable with a properly prepared Strachan Device and amplitude modulated diode laser.

For example, with a continuous diode laser, the pulse repetition frequency of the string of extremely short duration pulses is defined by the amplitude modulation frequency of the direct laser diode drive or the acousto-optic or electro-optic modulation device. The inherent current modulation of the direct laser drive method will result in more fluctuation in laser center frequency reducing the period of the coincident pulses while acousto-optic modulation provides a similar effect if the aperture of the modulated beam is greater than the diameter of the optimal modulation aperture of the crystal, as the outer radii will be less deeply modulated than the inner radii causing the effective aperture in the function to alter.

In the present method of producing the non-crystalline compositions, a rapid, alternating sequence of ultra-short laser pulses from at least two different lasers are applied to a solution of the composition, and evaporating the solvent. As discussed above, it is believed that the output bandwidth of the lasers is broadened by the short pulse length. This follows from the Uncertainty Principle. As a result, the short pulses of laser light are believed to provide photons that interact with multiple vibrational and/or electronic states of the composition to provide the non-crystalline form. As a result, lasers having an emission that corresponds to a specific absorption band of the composition are not required, and, thus, the choice of lasers is not critical. Good results have been obtained with all the pharmaceutical compositions discussed below using a laser that emits in the blue-violet band (preferably about 400 to about 470 nm) and a laser that emits in the red to near infrared wavelength band (preferably about 620 to about 680 nm), such as diode lasers. As the chemical structures and, thus, the absorption spectra of the pharmaceutical compositions treated with the process of the invention, as described herein, differ significantly, it is believed that the process of the invention can be extended to a variety of other organic compounds.

Preferably, the preferred alternating sequence comprises sparse nodes of constructive interference of ultra short duration in the two wavelength regions that are produced using at least a pair of lasers and one or more Strachan Devices. Without being bound by theory, it is believed that the alternating sequence of ultra-short laser pulses interacts with the electronic and/or vibrational states of the molecules of the composition, disrupting intermolecular interactions, and, thus, preventing crystal formation and/or disrupting the crystal structure.

The room temperature stable non-crystalline compositions of the invention are preferably produced by the alternating application of amplitude modulated sparse constructive nodes from at least two different lasers that are passed through a Strachan Device, and applied to a solution of the composition in a solvent. Preferably, the alternating applications are repeated frequently.

Useful solvents are typically organic solvents in which the composition is at least moderately soluble, that evaporate at about room temperature to about 130° C., and are nontoxic. Preferably, the composition is dissolved in an alcohol, and, more preferably, ethanol. Solvents are preferably anhydrous, and the most preferred solvent is anhydrous ethanol, i.e., 100 percent or absolute ethanol.

Preferably, the laser radiation is applied to the solution until the solvent is substantially evaporated. More preferably, the solution is heated during the application of the laser radiation and evaporation of the solvent, but may be cooled during the evaporation process, preferably to room temperature. Most preferably, the laser radiation is first applied to the solution, where the solution is covered with a transparent cover that substantially prevents evaporation of the solvent. The transparent cover is then removed, and the application of laser radiation is preferably continued as the solvent evaporates.

Preferably, the lasers comprise a laser that emits in the blue-violet wavelength and a laser that emits in the red-orange wavelength band. More preferably, the lasers preferably emit in the range of about 400 to about 470 nm and in the range of about 620 to about 680 nm, respectively. More than two lasers emitting at different wavelengths may be used with the invention. Good results have been obtained with a Strachan Device and diode lasers that emit at 408 nm and 674 nm.

Although the process of the invention has been shown to provide non-crystalline compositions in the presence of normal air, the process may also be performed in an inert atmosphere. The inert atmosphere may be provided using nitrogen, helium, argon, or other inert gas. For cost reasons, nitrogen is preferred. The use of the inert gas will eliminate any tendency of the non-crystalline compositions to oxidize during the process.

EXAMPLES

The following non-limiting examples are merely illustrative of the preferred embodiments of the present invention, and are not to be construed as limiting the invention, the scope of which is defined by the appended claims.

To confirm that the non-crystalline compositions prepared with the laser treatment of the invention were not an artifact of the experimental setup, experimental procedures were repeated with the exception that no laser radiation was applied to the solutions. That is samples of ezetimibe, statins, and aspirin, either individually or in combination, were dissolved in a solvent, placed on a hotplate in a covered Petri dish, and uncovered, allowing the solvent to evaporate, in accordance with the protocols discussed above in the examples. A substantial amount of crystalline material was observed in each of the comparative tests.

Example 1

Preparation of Non-Crystalline Aspirin

Non-crystalline aspirin is far from thermodynamic equilibrium at room temperature, and has always been found previously to be crystalline or to crystallize at temperatures above the glass transitions temperature, which is well below room temperature, up to the melt temperature. However, the repetitive application of laser radiation in accordance with the invention, converts aspirin to a predominant non-crystalline form that has been found to remain stable at room temperature for at least up to about a year.

Example 1a

A single sequence of long wavelength (red), 674 nm, followed by short wavelength 408 nm (violet), amplitude modulated and structured laser light from a Strachan Device was applied to a solution of aspirin in absolute ethanol. The approximately 3 cm expanded beam from each respective laser was slowly rotated over the sample at a distance of 25 cm from the Strachan Device for 2.5 minutes for each of the wavelengths of laser light. An analysis of the treated aspirin with plane polarized light microscopy demonstrated the occasional production of a small fraction of tiny isotropic droplets of aspirin, generally less than one millimeter (1 mm) in size, that were stable at room temperature once the solvent had evaporated. Most of the droplets had a core of birefringent crystalline material and a halo of isotropic aspirin, though a few droplets were purely isotropic. The ability of the isotropic material to resist crystallization when abutting forming fronts of crystallized material demonstrates the stability of the non-crystalline aspirin of the invention produced through this method once the solvent was evaporated.

Example 1b

The frequent, repeated sequenced application of laser radiation to produce stable non-crystalline aspirin resulted in the production of up to about 80 to about 90 percent or more of transparent non-crystalline aspirin. Droplets of pure glassy material of about 2 to 3 mm or more and lakes of non-crystalline aspirin dozens of millimeters wide have been found to be stable for up to about a year at room temperature.

As discussed above, a reference standard crystalline aspirin was analyzed by PXRD. The characteristic pattern of reflection peaks of the reference standard crystalline aspirin is illustrated in FIG. 1. The crystalline aspirin was also analyzed using Fourier transform infrared spectroscopy, as illustrated in FIG. 2. As the PXRD pattern of a compound in the non-crystalline state results in disappearance of characteristic reflection peaks, FTIR spectroscopy confirms compound identification, and provides further evidence of the non-crystalline state by showing a broadening of absorption bands that occurs in the non-crystalline compared to the crystalline state.

The highly non-crystalline state of aspirin was produced by repeated applications of cycles of sequences of long wavelength followed by short wavelength laser light modulated and structured by a Strachan Device. A 10 mg sample of a crystalline aspirin reference standard was dissolved in 450 mg of absolute ethanol by stirring at 9000 revolutions per minute (rpm) with a magnetic stirrer, while heating to 140° C. for 12.5 minutes in a stoppered Erlemneyer flask. The solution was transferred into a 60 mm×15 mm glass Petri dish, covered with a glass lid. The Petri dish was heated to 100° C. on a hotplate.

The aspirin solution was treated with repeated cycles of laser radiation modified with a Strachan Device. The first cycle was the application of amplitude modulated diode laser light from a diode laser having a central wavelength of 674 nm. The second cycle was the application of amplitude modulated diode laser light from a diode laser having a central wavelength of 408 nm. The sample was rotated slowly through each approximately 3 cm expanded beam at a distance of 25 cm from the Strachan Device.

The 674 m laser diode beam had a peak power of 4.80 mW without optics. After passing through a Thorlabs 5× beam expander and the Strachan Device the peak power was reduced by about 50 percent. Using the Strachan Device, the 674 nm beam was adjusted to the 80 percent phase cancellation level to achieve a power of about 0.48 mW over a 3 cm diameter beam.

The 408 nm beam had a peak power of about 4.8 mW without added optical elements. After passing through a Thorlabs 5× beam expander and the Strachan Device the peak power was reduced by about 50 percent. Using the Strachan Device, the 408 nm beam was adjusted to the 80 percent phase cancellation level to obtain a 3 cm diameter beam of about 0.48 mW.

Both beams were electronically amplitude modulated at 6.25 Megahertz (MHz). As discussed above, without being bound by theory, it is believed that the output bandwidth of the lasers is broadened by the short effective pulse length produced by the Strachan Device, which follows from the Uncertainty Principle. This provides interaction of the photons in the laser light with multiple electronic and/or vibrational modes of the aspirin molecules.

The aspirin solution was treated in the covered glass Petri dish while on the hotplate for one minute with the 674 m configuration, then for one minute with the 408 nm configuration as above. This was followed with another cycle of the amplitude modulated and structured 674 nm configuration, followed by the 408 nm laser configurations for one minute for each laser system. The third sequence of the 674 nm laser followed by the 408 nm laser treatment was for 2 minutes with each laser system.

After this cycle the glass cover was removed from the Petri dish to permit evaporation of the ethanol. For the duration of the laser treatments, spanning 5 more cycles, the aspirin in ethanol solution remained on the hotplate. The next cycle of 674 nm followed by 408 nm laser treatments was for 2 minutes with each laser system. The next 4 cycles of 674 nm followed by 408 nm laser treatments applied 2 minutes per cycle with the laser systems applied for one minute each per cycle. Upon completion of the last cycle of laser treatment the sample of laser treated aspirin was removed from the hotplate to continue the process of solvent evaporation at a room temperature of about 18° to 20° C. and a humidity of 35 percent.

At the end of the laser treatment, most of the solvent had already evaporated, resulting in a "lake" of clear transparent non-crystalline aspirin approximately 3 cm wide. A narrow rim of crystallization had formed around the outer margin of the lake in a band representing approximately 30 percent of the circumferential perimeter. Despite the formation of an active crystallization front, there was negligible extension of this front after completion of the cycles of the sequenced laser treatments.

Within an hour of the evaporation, the system stabilized with 80 percent or more of the mass of the sample cured to a clear non-crystalline form rather than a crystalline form. Continued storage at a room temperature of about 18° to 22° C. and about 30 to 40 percent humidity resulted in no change in appearance of the sample during a period of over 6 months duration, with preservation of the wide expanse of transparent non-crystalline aspirin even adjacent to the rim of crystallization. Those observations demonstrate the stability of the non-crystalline form of aspirin produced with the method of the invention.

After the 6 months of storage, the laser treated aspirin was studied by PXRD. This pattern, shown in FIG. 3, demonstrates this material to be highly X-ray non-crystalline, in marked contrast to the highly crystalline pattern shown in FIG. 1 for the control crystalline aspirin. Compared to the high intensity reflection peaks seen for crystalline aspirin, for laser treated aspirin these peaks are essentially completely eliminated, indicating that at most only very short range ordering remains in the non-crystalline glass form produced. No crystallization has been observed in similarly prepared samples following an additional six months of storage. Those observations demonstrate the stability of the non-crystalline form of aspirin produced with the method of the invention.

The X-ray non-crystalline aspirin sample was then scanned using Fourier transform infrared (FTIR) spectroscopy, as shown in FIG. 4. In comparison to the FTIR spectroscopy of aspirin reference crystalline material shown in FIG. 2, relatively broad absorption bands are evident in the X-ray non-crystalline samples of aspirin as compared with the more defined bands of the crystalline aspirin reference sample. Infrared spectra of crystalline materials typically exhibit sharper or better resolved absorption bands than the non-crystalline form because of the reduced freedom of movement of the molecules in a crystalline lattice. Some bands in an infrared spectrum may also be shifted somewhat because of changes in form between crystalline materials and the non-crystalline form of the same compound. Comparing the FTIR spectra of crystalline aspirin and laser treated aspirin, these compounds are clearly the same chemical entity. The broadening of the spectral peaks in laser treated aspirin is an additional feature consistent with the non-crystalline form of aspirin.

Example 1c

Subsequent tests with the protocol of Example 1b were repeated with the order of long and short wavelengths reversed, i.e., short wavelength followed by long wavelength cycled sequenced laser treatment. This protocol also produced up to 90 percent yields of room temperature stable non-crystalline glass aspirin, which remained stable at room temperature for over 23 months. The Petri dish containing such a sample of non-crystalline aspirin was placed on edge for a period of about six weeks. No flowing of the sample was observed.

Comparative Example

Aspirin

Figure 5:
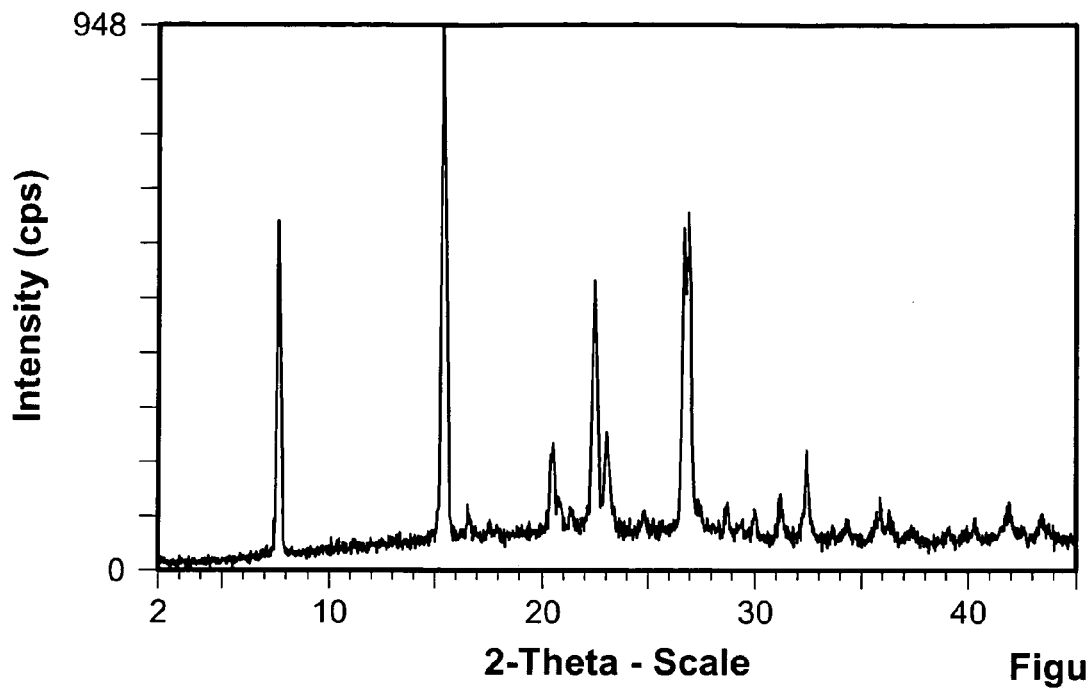
FIG. 5 illustrates the PXRD pattern of a sample of crystalline aspirin formed in the process of the invention, with the exception that laser radiation was not applied.
Figure 6:
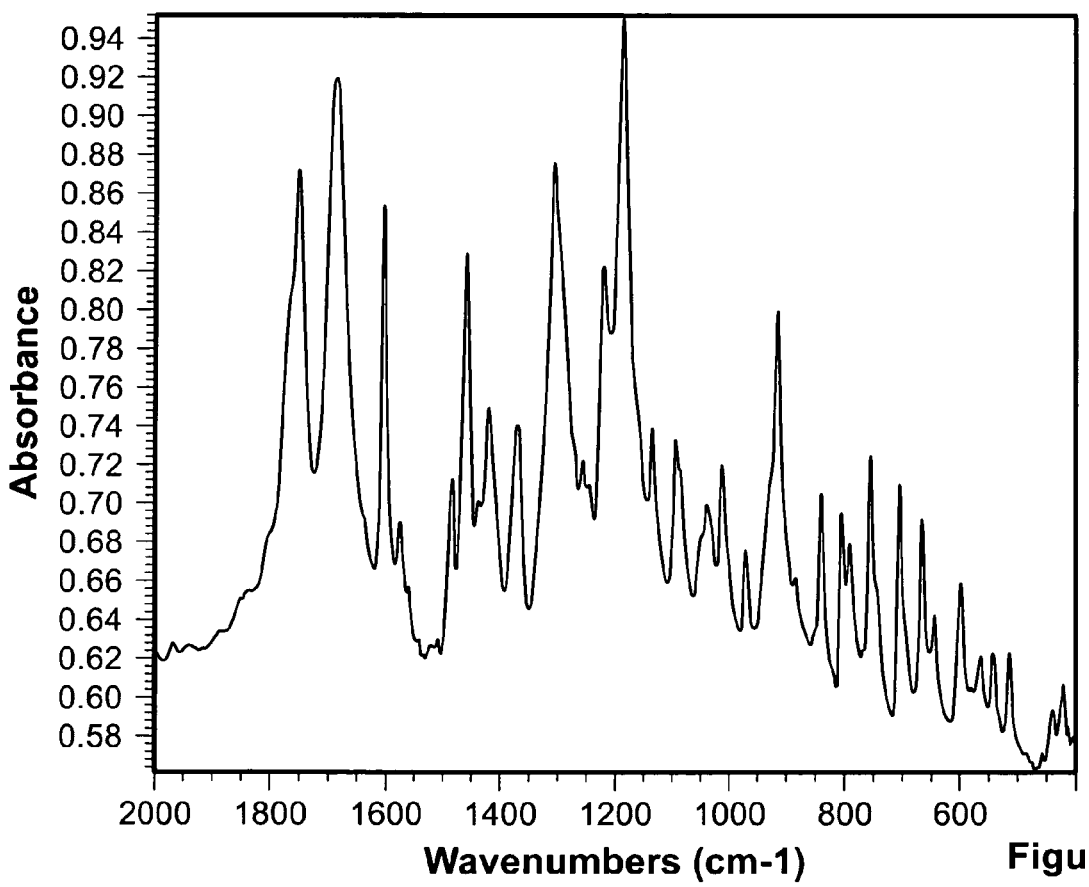
FIG. 6 illustrates an FTIR spectrum of the crystalline aspirin sample of FIG. 5.

The protocols of Examples 1b and 1c were repeated with the exception that there was no application of laser radiation. The resulting material was visibly crystalline, which was confirmed by PXRD analysis, which demonstrated that a substantial amount of crystalline material was present. A PXRD pattern for the aspirin obtained without the application of the laser radiation is illustrated in FIG. 5. The PXRD pattern of FIG. 5 has the same peaks as that of the control sample illustrated in FIG. 1. An FTIR analysis of the resulting aspirin was also performed. The resulting spectrum is illustrated in FIG. 6, and is substantially the same as that illustrated in FIG. 2. Those results clearly demonstrate that the non-crystalline aspirin is not an artifact of the experiment, but, instead, is a direct result of the application of the laser radiation in the process of the invention.

Example 2

Preparation of Non-Crystalline Simvastatin

Figure 7:
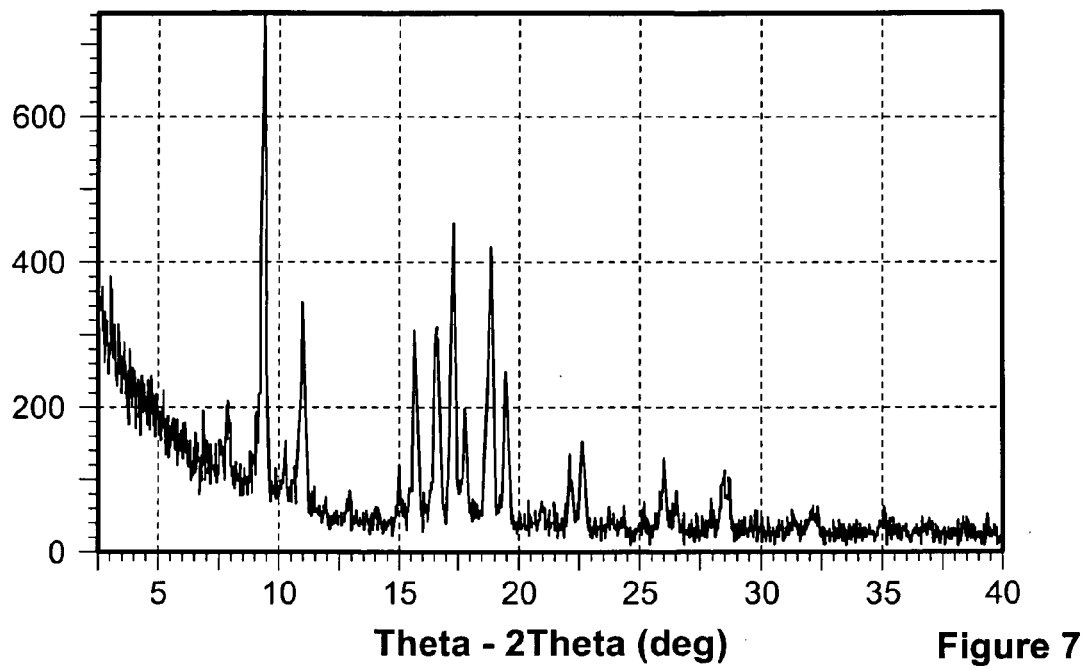
FIG. 7 illustrates the PXRD pattern of a sample of crystalline simvastatin.
Figure 8:
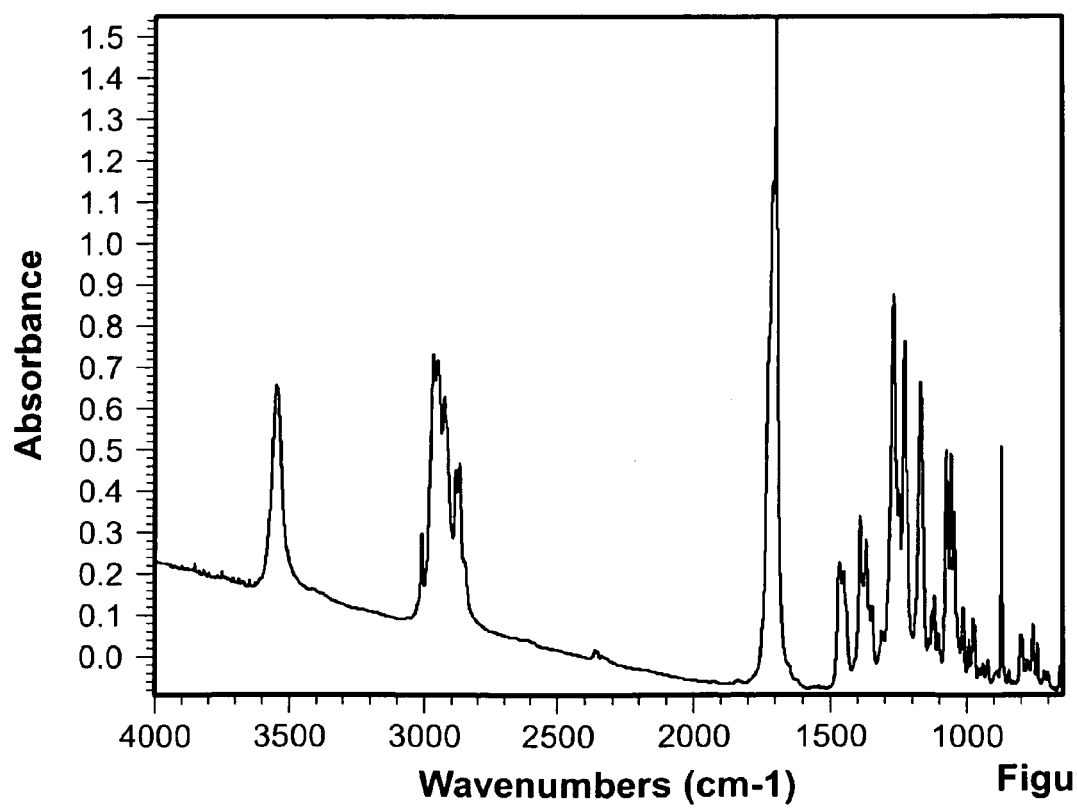
FIG. 8 illustrates the FTIR spectrum of the crystalline simvastatin.

A control sample of crystalline simvastatin was analyzed by PXRD. The characteristic PXRD pattern of crystalline simvastatin obtained from the sample is illustrated in FIG. 7. The crystalline simvastatin was further analyzed using Fourier transform infrared (FTIR) spectroscopy, and the FTIR absorption spectrum of the crystalline simvastatin is illustrated in FIG. 8.

To obtain non-crystalline simvastatin, a 40 mg sample of crystalline simvastatin was dissolved in 674 mg of 100 percent (absolute) ethanol with stirring at 9000 revolutions per minute (rpm) for 8 minutes in a stoppered Erlenmeyer flask, followed by heating to 140° C. for an additional 10 minutes at 9000 rpm. The solution was cooled to approximately 20° C., i.e., room temperature, filtered using a syringe to remove any residual crystals, decanted into a 60 mm×15 mm glass Petri dish, and covered with a glass lid.

The dissolved sample of laser treated simvastatin was first treated with amplitude modulated diode laser light having a central wavelength of 674 nM for 2.5 minutes, and then with amplitude modulated diode laser light having a central wavelength of 408 nm for 2.5 minutes, while rotating the sample slowly through each of the approximately 3 cm expanded beams at a distance of 25 cm from the output of the respective Strachan Devices.

The 674 nm laser diode beam had a peak power of 4.80 mW without optics. After passing through a Thorlabs 5× beam expander and the Strachan Device the peak power was reduced by about 50 percent. Using the Strachan Device, the 674 nm beam was adjusted to the 80 percent phase cancellation level to obtain a 3 cm diameter beam of about 0.48 mW.

The 408 nm beam had a peak power of about 0.32 mW without added optical elements. After passing through a Thorlabs 5× beam expander and the Strachan Device the peak power was reduced by about 50 percent. Using the Strachan Device, the 408 nm beam was adjusted to the 80 percent phase cancellation level to obtain a 3 cm diameter beam of about 0.02 mW. Both beams were electronically amplitude modulated at 6.25 Megahertz (MHz).

Figure 9:
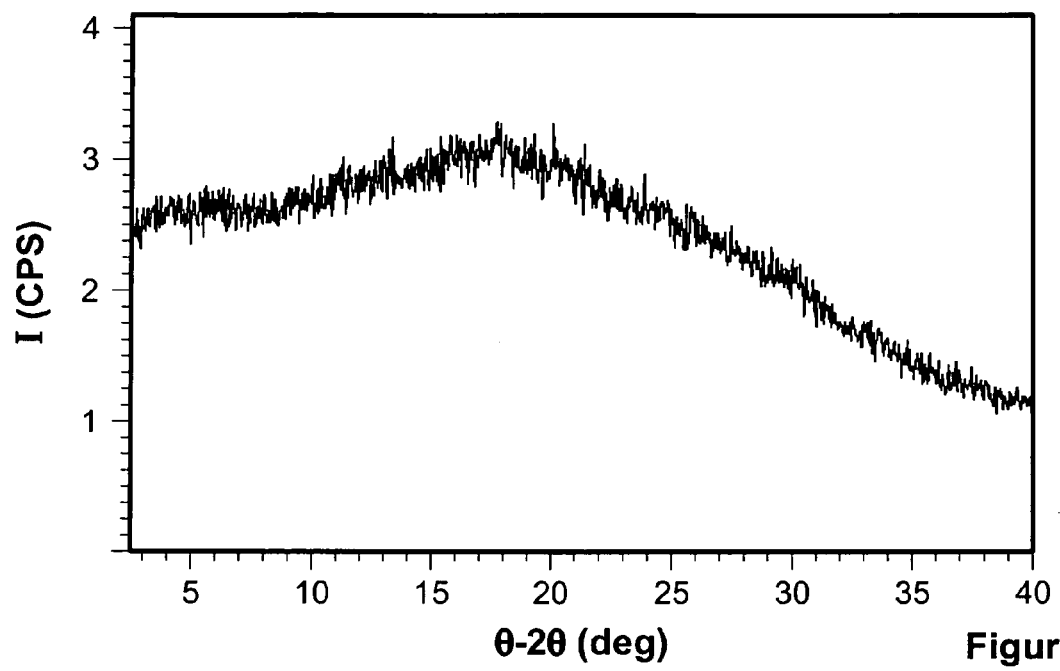
FIG. 9 illustrates the PXRD pattern of a sample of simvastatin treated with the process of the invention.

The lid of the glass Petri dish was removed, and the was solution allowed to dry through slow evaporation at a room temperature of about 19° to 20° C. and 41 percent humidity. The resultant material dried to a pure transparent glass state. The sample of laser treated simvastatin was examined by polarizing light microscopy (PLM), and was found to appear entirely isotropic, indicating the material was purely non-crystalline. The laser treated simvastatin was then studied using PXRD. This pattern is illustrated in FIG. 9, and is substantially free of any of the PXRD peaks of the crystalline simvastatin, demonstrating that the laser treated simvastatin was non-crystalline.

Figure 10:
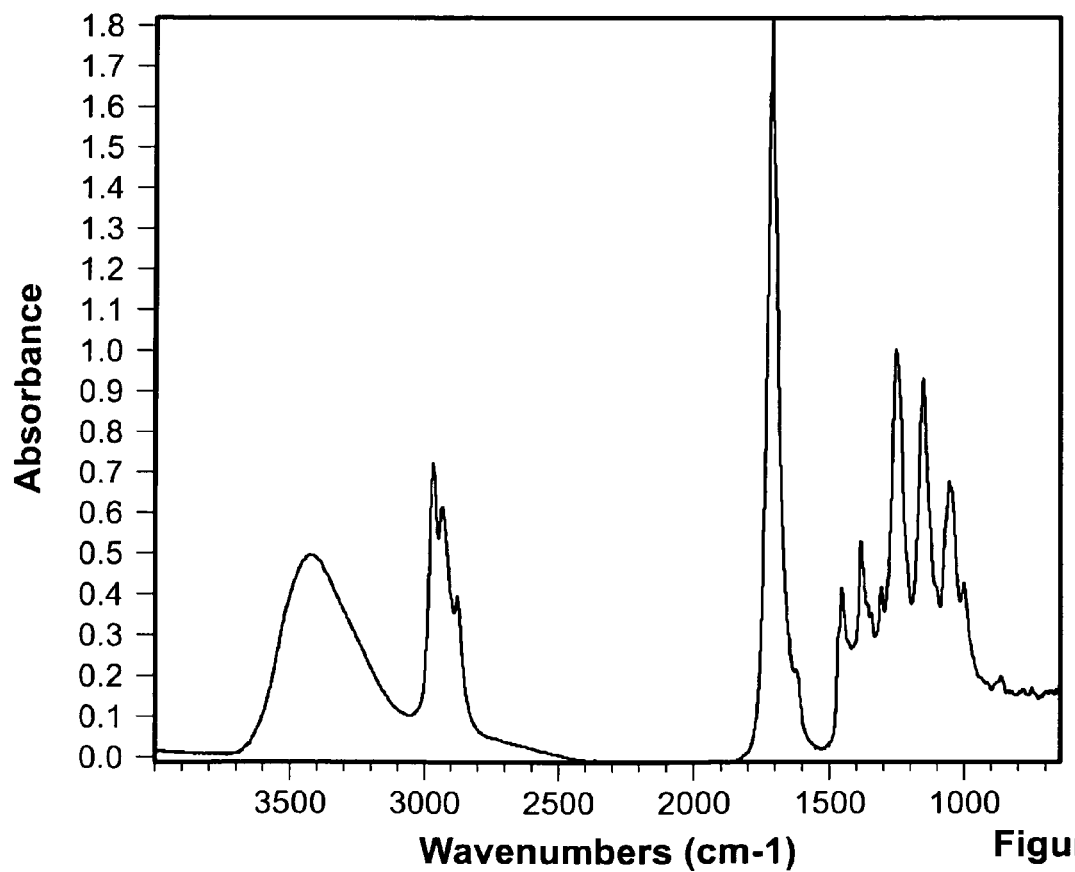
FIG. 10 illustrates the FTIR spectrum of the simvastatin treated with the process of the invention.

The non-crystalline simvastatin produced with the process of the invention was then subjected to an FTIR analysis. The resulting FTIR spectrum is illustrated in FIG. 10. In comparison to the FTIR spectrum obtained from the crystalline simvastatin illustrated in FIG. 8, the absorption bands of the FTIR spectrum of the laser treated simvastatin are relatively broad compared with the much more defined bands of the crystalline simvastatin reference sample.

Comparative Example

Simvastatin

Figure 79:
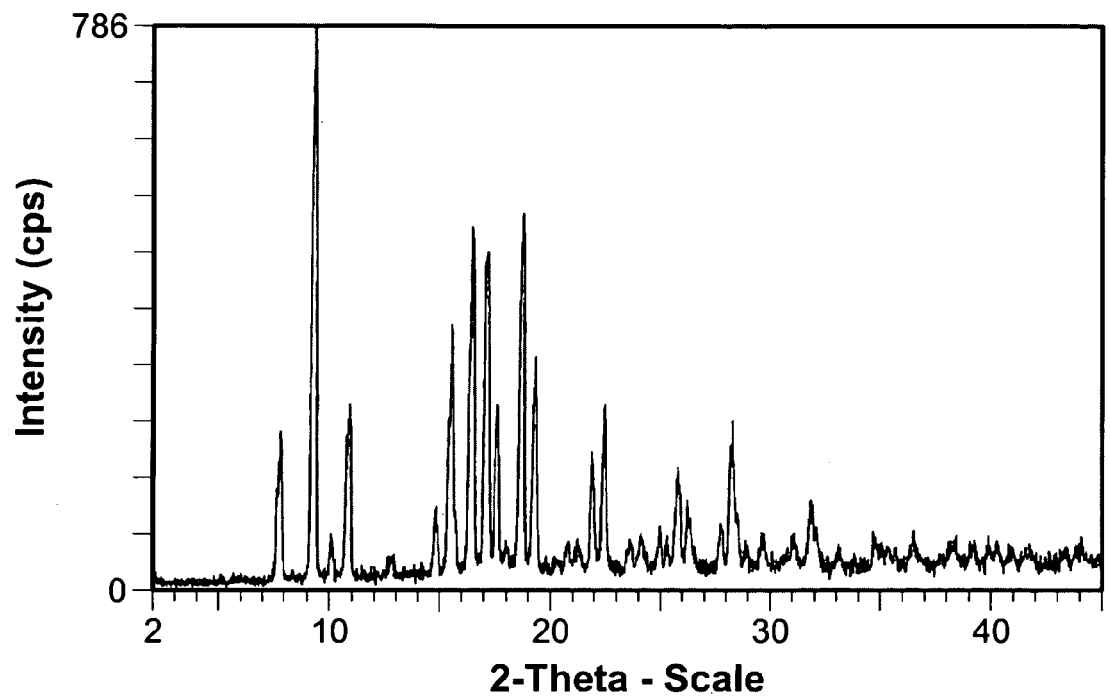
FIG. 79 illustrates the PXRD pattern of a sample of simvastatin formed in the process of the invention, with the exception that laser radiation was not applied.
Figure 80:
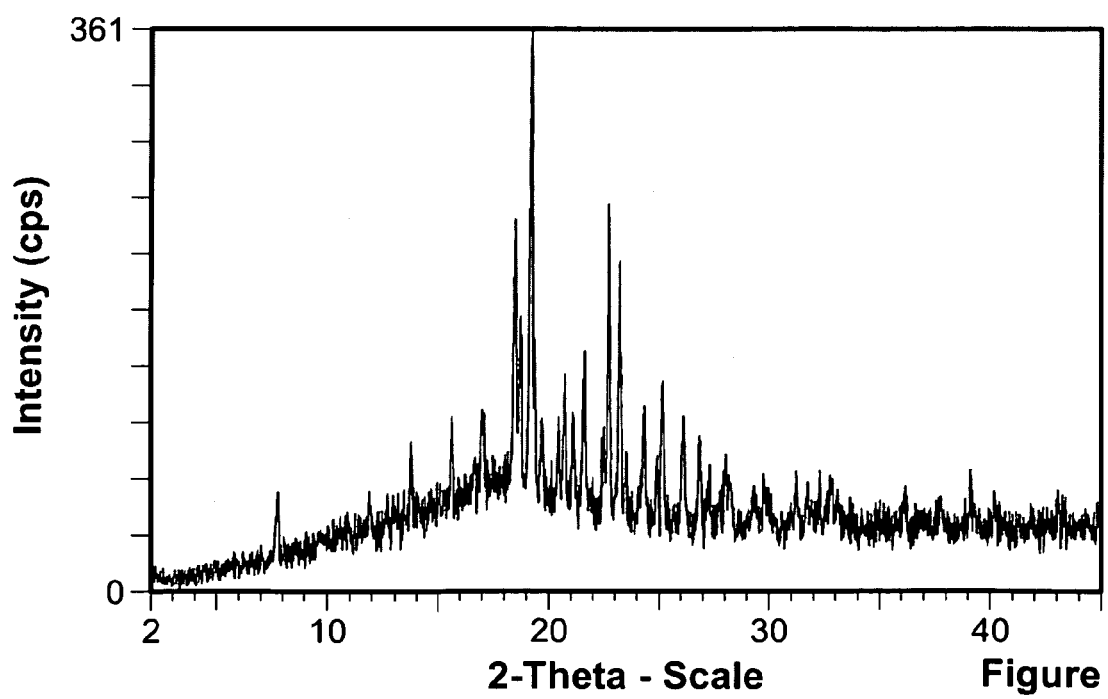
FIG. 80 illustrates the PXRD pattern of a 1:1 weight ratio sample of ezetimibe/simvastatin formed in the process of the invention, with the exception that laser radiation was not applied.
Figure 81:
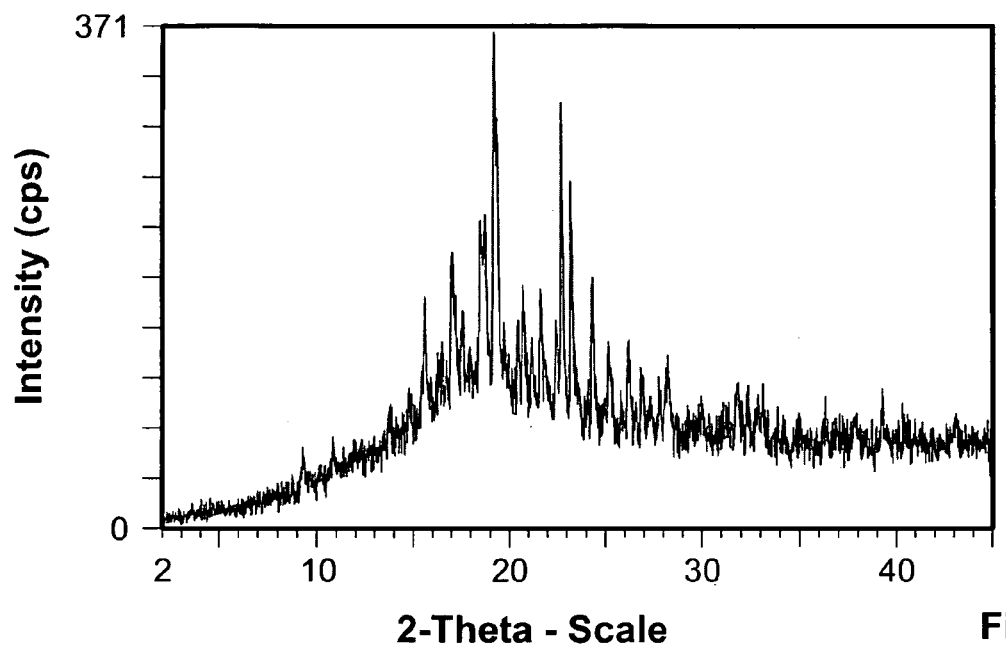
FIG. 81 illustrates the PXRD pattern of a 1:2 weight ratio sample of ezetimibe/simvastatin formed in the process of the invention, with the exception that laser radiation was not applied.
Figure 82:
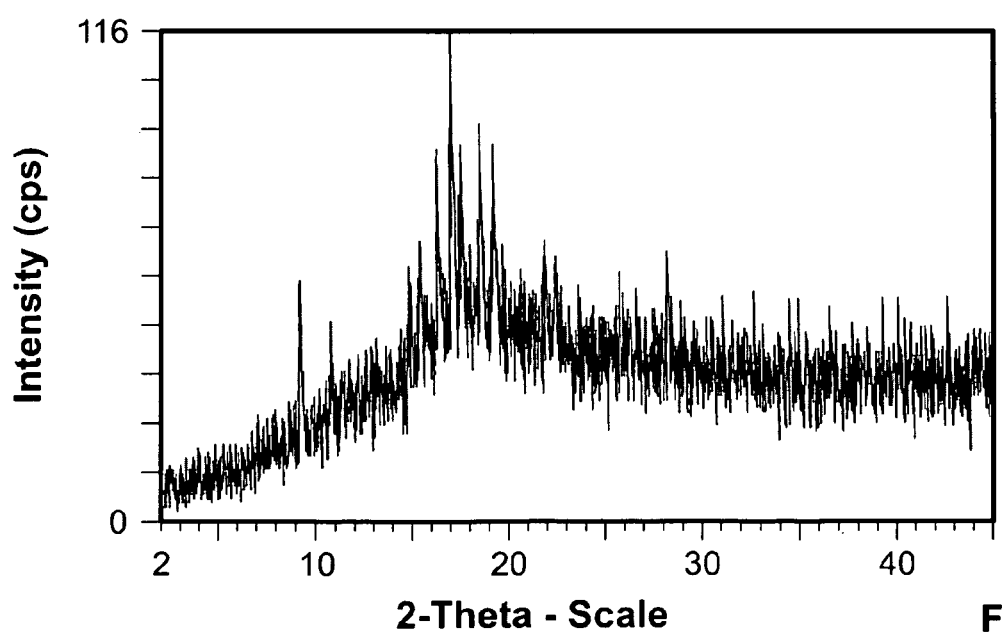
FIG. 82 illustrates the PXRD pattern of a 1:4 weight ratio sample of ezetimibe/simvastatin formed in the process of the invention, with the exception that laser radiation was not applied.
Figure 83:
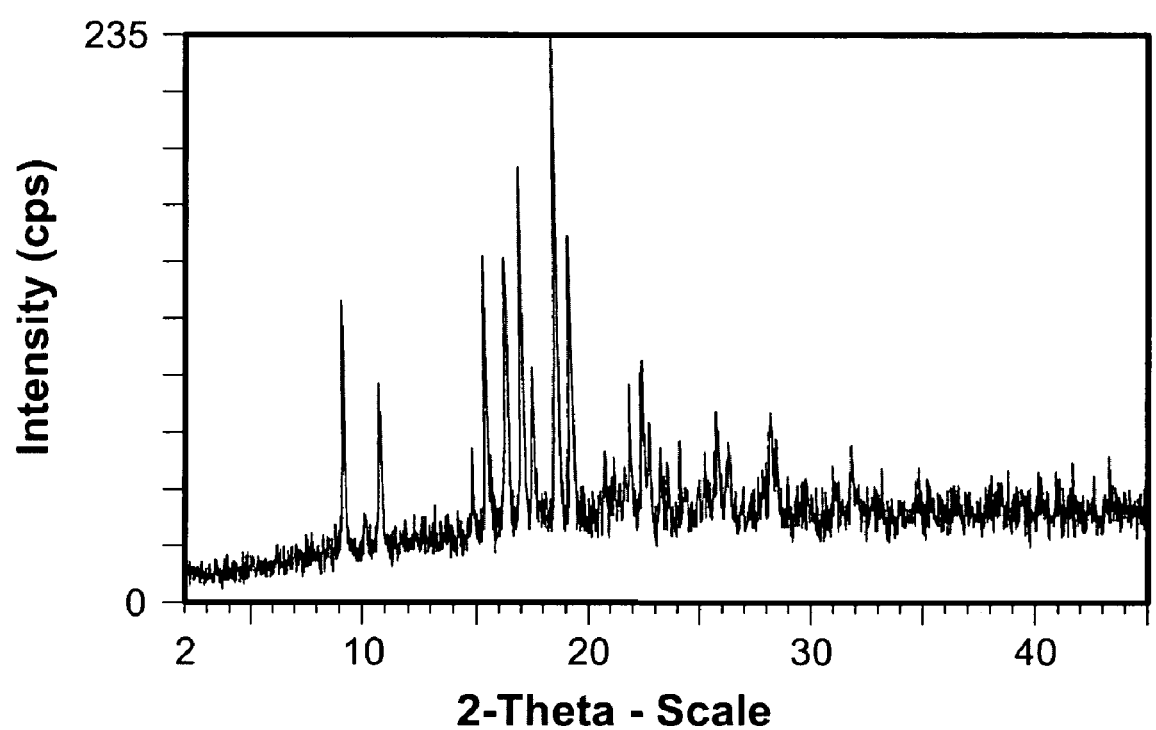
FIG. 83 illustrates the PXRD pattern of a 1:8 weight ratio sample of ezetimibe/simvastatin formed in the process of the invention, with the exception that laser radiation was not applied.

The protocol of Example 2 was repeated with the exception that there was no application of laser radiation. The resulting material was visibly crystalline, which was confirmed by PXRD analysis, which demonstrated that a substantial amount of crystalline material was present. A PXRD pattern for the simvastatin obtained without the application of the laser radiation is illustrated in FIG. 79. An FTIR analysis of the resulting simvastatin was also performed, confirming the material was simvastatin. The results demonstrate that the non-crystalline simvastatin is not an artifact of the experiment, but, instead, is a direct result of the application of the laser radiation in the process of the invention.

Example 3

Preparation of Non-Crystalline Ezetimibe

Crystalline ezetimibe was subjected to analysis by light microscopy, PXRD, and FTIR spectroscopy to serve as a reference sample for comparison to ezetimibe treated with the process of the invention. Optical plane polarized light microscopy confirmed that the ezetimibe reference sample was entirely birefringent, and, thus, highly crystalline. The PXRD spectrum of the crystalline ezetimibe illustrated in FIG. 11 includes the peaks that are characteristic of the crystalline material. The characteristic FTIR pattern of control crystalline ezetimibe is illustrated in the upper portion of FIG. 12.

To obtain non-crystalline ezetimibe, 50 mg of ezetimibe was dissolved in 500 mg of absolute ethanol, and stirred with a stir bar in a stoppered Erlenmeyer flask for 5 minutes. The stopper was removed, and the ezetimibe and absolute ethanol were then stirred while being heated at 165° C. for an additional for 6 minutes. After about 30 percent of the ethanol evaporated, the solution of ezetimibe in ethanol was decanted into a 60 mm×15 mm glass Petri dish. A glass cover was placed over the Petri dish, and amplitude modulated diode laser radiation from the at 408 nm wavelength laser was applied for 2.5 minutes, followed amplitude modulated diode laser radiation from the 674 nm wavelength laser for 2.5 minutes.

The 408 nm beam had a peak power of about 0.48 mW without added optical elements. After passing through a Thorlabs 5× beam expander and the Strachan Device the peak power was reduced by about 50 percent. The 674 nm laser diode beam had a peak power of 4.80 mW without optics. After passing through a Thorlabs 5× beam expander and the Strachan Device the peak power was reduced by about 50 percent. Both beams were electronically amplitude modulated at 6.25 MHz. Using the Strachan Device, both the 408 nm beam and the 674 nm laser were adjusted to the 80 percent phase cancellation level to obtain power levels of 0.05 mW and 0.48 mW over 3 cm diameter beams, respectively.

First, the Strachan Device modified emission of the 408 nm modulated diode laser output was directed straight upward with the beam expanded to about 3 cm and the sample located about 29 cm from the output of the Strachan Device for a period of about 2.5 minutes. Then, the Strachan Device modified emission of the 674 nm modulated laser diode output was directed straight upward with the beam expanded to about 3 cm and the sample located about 29 cm from the Strachan Device for a treatment duration of 2.5 minutes. The ezetimibe in the glass Petri dish was slowly circulated through the beam to cover the entire surface area.

The glass cover was removed and the sample was allowed to desolvate in an open container through slow evaporation at about 20° C. and a relative humidity of 31 percent. Before the solvent had fully evaporated, the sample developed a few small areas of apparent crystallization that were surrounded with marker lines. As the evaporation continued, no significant extension of the crystal fronts was observed. The fronts remained stable for five weeks, and there was no encroachment on the predominantly isotropic glassy material of the sample by the crystalline material, suggesting significant stability of the non-crystalline form, even when exposed to crystallization fronts.

A light microscopy evaluation of the samples was performed using a Leica DM LP microscope equipped with Spot Insight color camera (model 3.2.0). A 5×, 10×, 20×, or 40× objective was used with cross polarizers and a first order red compensator in place to view samples. Sample coatings were carefully scraped from the dishes, placed on a glass slide, and covered with a drop of silicon oil. A cover glass was then placed over the samples. Images were acquired at ambient temperature using Spot software (v.4.5.9 for Windows).

Figure 13:
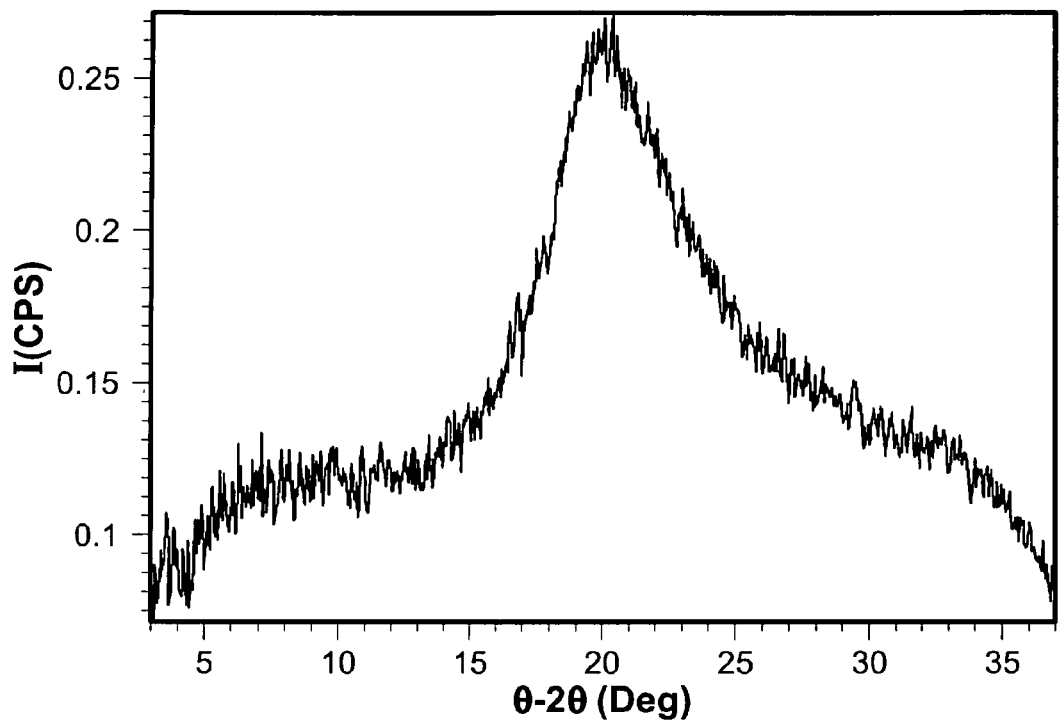
FIG. 13 illustrates the PXRD pattern of the ezetimibe treated with the process of the invention.
Figure 14:
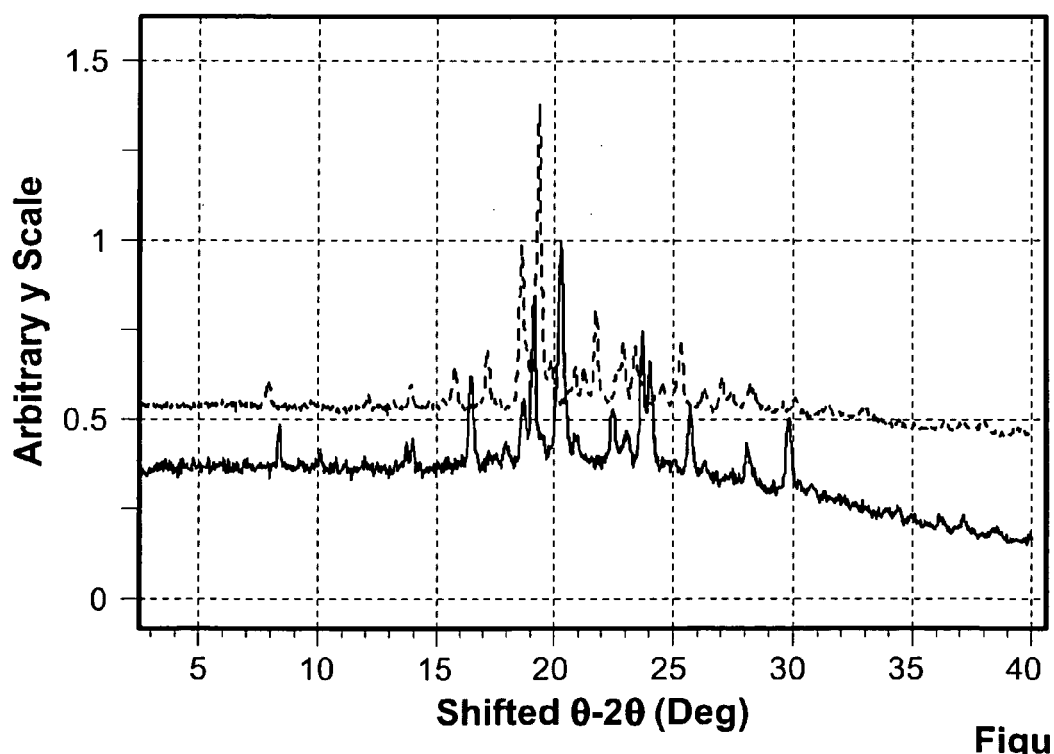
FIG. 14 illustrates a comparison of the PXRD pattern of a reference sample of crystalline ezetimibe and a sample of crystalline ezetimibe produced with the process of the invention, where the PXRD pattern of the crystalline ezetimibe produced with the process of the invention is different from that of the control crystalline ezetimibe.

Analysis of the ezetimibe treated with the process of the invention demonstrated that in excess of 90 percent of the treated ezetimibe was in the form of an isotropic film. A PXRD analysis of the isotropic ezetimibe provided a PXRD pattern having a very broad reflection centered at approximately 20°2θ, confirming that the isotropic film collected is non-crystalline. The PXRD pattern of the non-crystalline ezetimibe, as illustrated in FIG. 13, is free of the characteristic PXRD peaks of crystalline ezetimibe.

Figure 12:
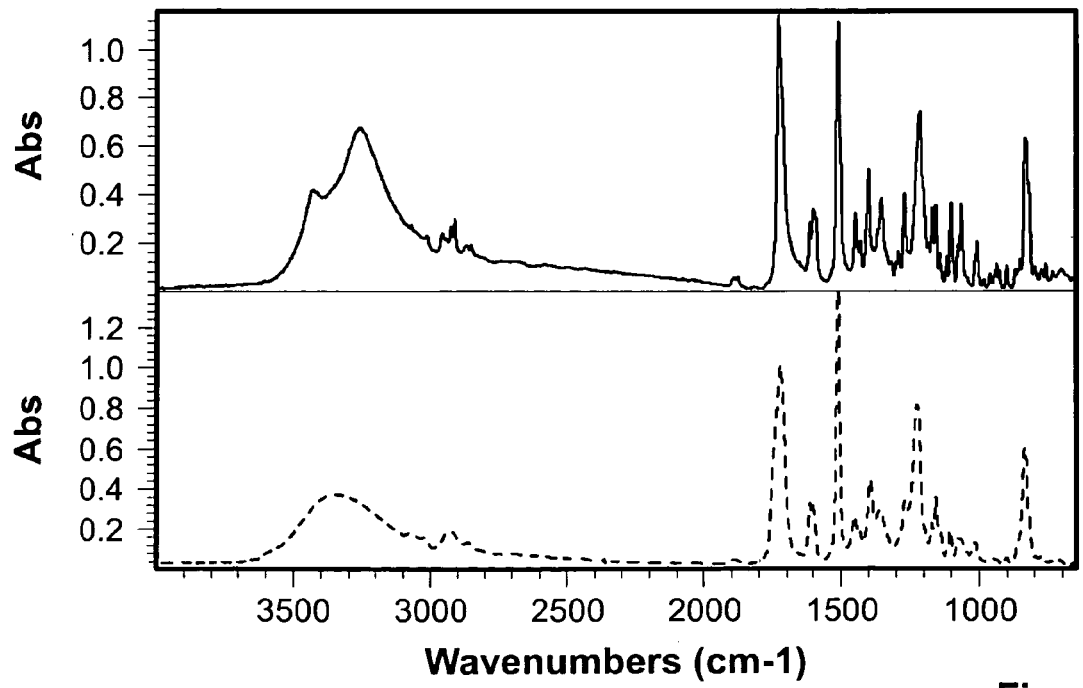
FIG. 12 illustrates the FTIR spectrum of the crystalline ezetimibe, and the FTIR spectrum of a sample of ezetimibe treated with the process of the invention.

The FTIR spectrum of the non-crystalline ezetimibe, as illustrated in the lower portion of FIG. 12, when compared to the FTIR spectrum of the crystalline ezetimibe is illustrated in the lower portion of FIG. 12 confirms that the non-crystalline material is ezetimibe. Although the crystalline ezetimibe has an FTIR spectrum with sharper peaks than the FTIR spectrum of the non-crystalline ezetimibe film the two FTIR spectra confirm that the non-crystalline material is ezetimibe.

The ezetimibe treated with the process of the invention also yielded a small area of microscopically birefringent material that remained stable for several weeks after solvent evaporation, indicating that the isotropic, non-crystalline ezetimibe resisted crystallization even when adjacent to an organizing crystal front, suggesting that non-crystalline ezetimibe produced through this method, once desolvation occurs, achieves significant stability over reversion to a crystal form.

The PXRD pattern of the birefringent ezetimibe produced with the process of the invention proved significantly different from the crystal pattern of the reference crystalline ezetimibe. As illustrated in FIG. 8, the PXRD pattern of the microscopically birefringent material from the laser treated ezetimibe has a PXRD pattern with peaks that are significantly different from that of control crystalline ezetimibe. That indicates the preparation of a different crystal form of ezetimibe.

By producing a stabilized non-crystalline pattern in the desolvating ezetimibe, a unique crystal form different from the initial crystal form of the compound emerged from the system. While this disclosure has focused primarily on the ability to produce the non-crystalline state of compounds that tend to crystallize, it has been found that the process of the invention may also be used to create conditions that favor the generation of new polymorphic crystal forms of such compounds. In this case, a polymorphic crystal form self organized from the conditions favoring producing the compound in the non-crystalline state. It is believed that the process of the invention can be applied to favor a particular solid state organization as a step or sequence of steps before or during desolvation.

The production of small quantities of new crystal forms should be useful as seed crystals to generate substantially larger quantities of the new form. If this new form is less thermodynamically favored and less stable than the original form the application of laser treatment during the process before or during desolvation until complete may permit scaling up production of the new form to the level required for practical use.

The new crystal form for ezetimibe shown in FIG. 8 is similar though possibly not identical to a previously reported form. Minimally this disclosure indicates a new method through which this form can be produced. If further comparison shows they are differentiated, then this crystal form will require testing for solubility and bioavailability to determine if there are potential advantages to the use of this form.

Comparative Example

Ezetimibe

Figure 67:
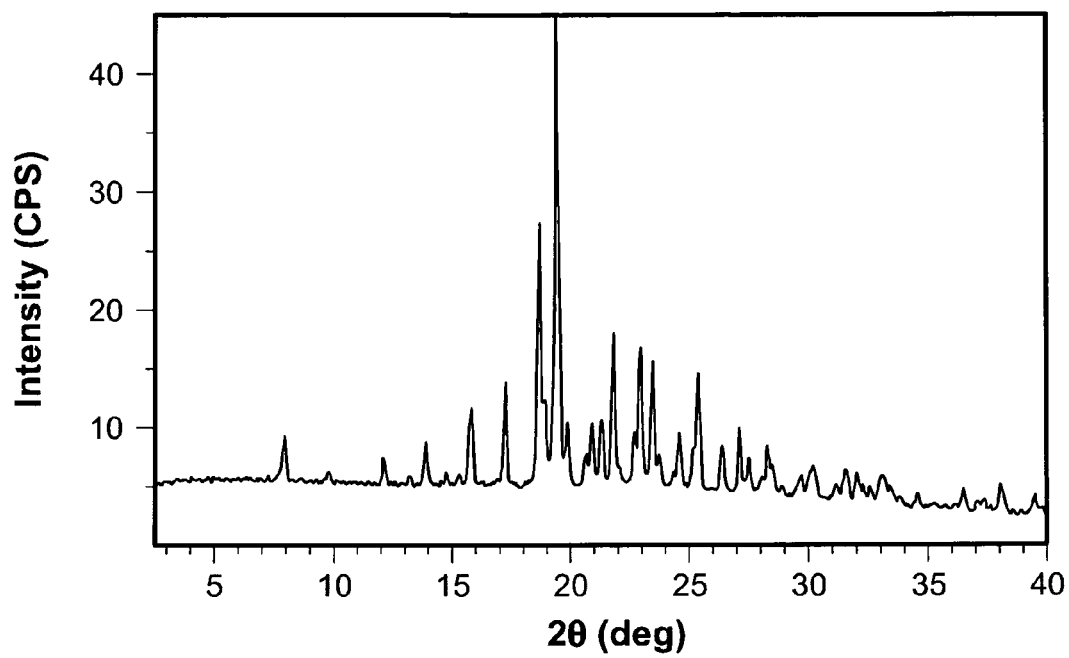
FIG. 67 illustrates the PXRD pattern for a sample of crystalline ezetimibe formed in the process of the invention, with the exception that laser radiation was not applied.

The protocol of Example 3 was repeated with the exception that there was no application of laser radiation. The resulting material was visibly crystalline, which was confirmed by PXRD analysis, which demonstrated that a substantial amount of crystalline material was present. A PXRD pattern for the ezetimibe obtained without the application of the laser radiation is illustrated in FIG. 67. The PXRD pattern of FIG. 67 has the same peaks as that of the control sample illustrated in FIG. 11. An FTIR analysis of the resulting ezetimibe was also performed, confirming the material was ezetimibe. The results demonstrate that the non-crystalline ezetimibe is not an artifact of the experiment, but, instead, is a direct result of the application of the laser radiation in the process of the invention.

Example 4

Preparation of Non-Crystalline Atorvastatin Free Acid

Figure 15:
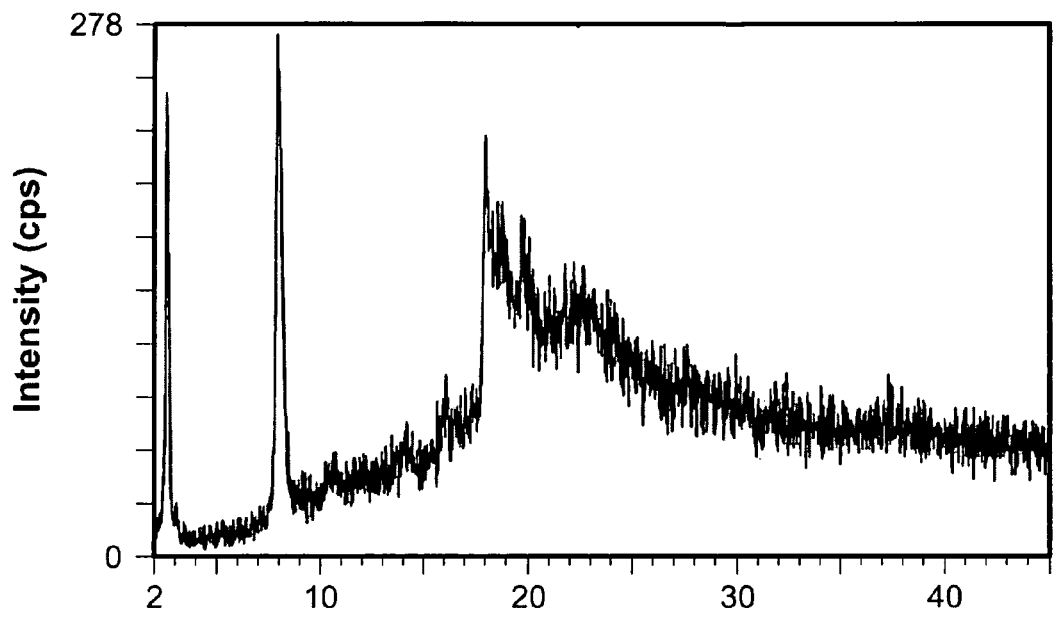
FIG. 15 illustrates the PXRD pattern of a sample of crystalline atorvastatin free acid.
Figure 17:
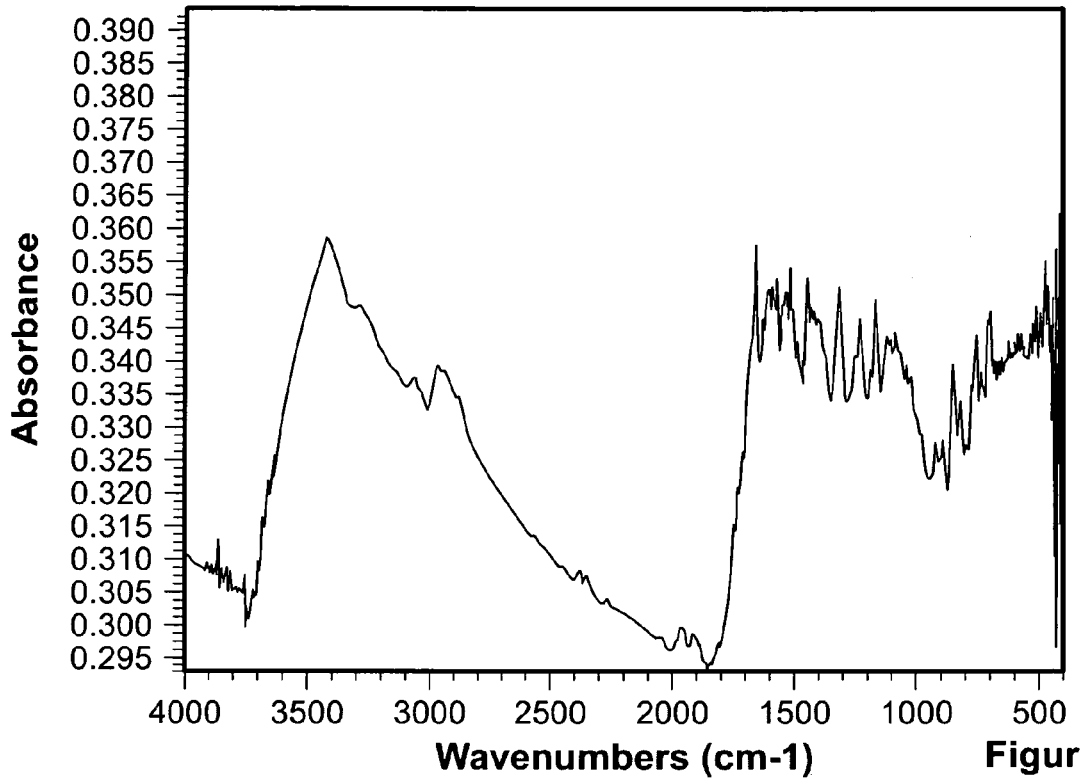
FIG. 17 illustrates the FTIR spectrum of a sample of crystalline atorvastatin free acid.

A reference sample of crystalline atorvastatin free acid was analyzed with PXRD and FTIR spectroscopy. As illustrated in FIG. 15, the PXRD spectrum of crystalline atorvastatin free acid is characterized by a PXRD having a number of specific peaks. The FTIR spectrum of the crystalline atorvastatin free acid is illustrated in FIG. 17.

A 10 mg sample of crystalline atorvastatin free acid was dissolved in 400 mg of absolute ethanol with heating to 160° C. and stirring at 9000 rpm for 11 minutes. The resulting solution was transferred into a 60 mm×15 mm glass Petri dish, covered with a glass lid, and placed on a hotplate at 100° C.

Figure 16:
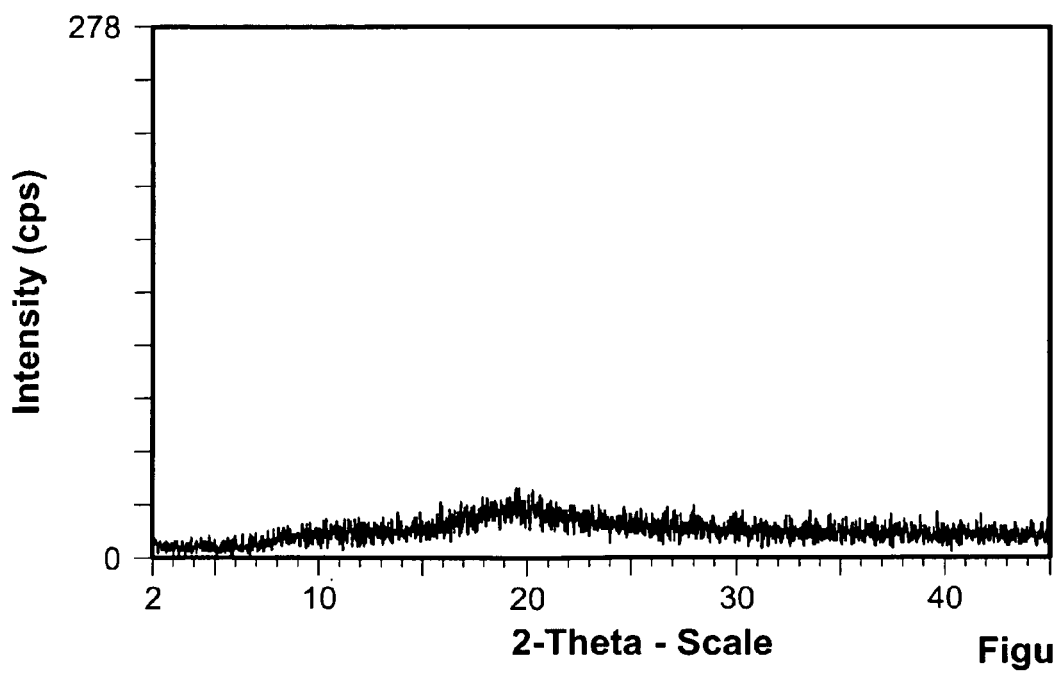
FIG. 16 illustrates the PXRD pattern of a sample of atorvastatin free acid treated with the process of the invention.

First, the amplitude modulated emission of a 674 nm diode laser was applied to the solution of atorvastatin free acid for 2.5 minutes. Then, the amplitude modulated emission of a 408 nm diode laser was applied for 2.5 minutes, rotating the sample slowly through the approximately 3 cm expanded beam at a distance of 25 cm from the Strachan Device. The 674 nm laser diode beam was passed through a Thorlabs 5× beam expander and a Strachan Device. Using the Strachan Device, the 674 μm beam was adjusted to the 80 percent phase cancellation level to achieve a power of approximately 0.48 mW over the 3 cm diameter beam. The 408 μm beam had a peak power of 2.18 mW after passing through a Thorlabs 5× beam expander and the Strachan Device. The output of the 408 μm beam was also optically phase cancelled using the Strachan Device to achieve a measured 80 percent reduction of transmitted power to 0.44 mW over the 3 cm diameter beam. Both beams were electronically amplitude modulated at 6.25 MHz The lid of the glass Petri dish was removed, and the solution was allowed to dry through slow evaporation at a room temperature of about 19° to about 20° C. and about 36 percent humidity. The resultant material dried to a pure transparent glass state. The laser treated atorvastatin free acid was then studied using PXRD. The PXRD pattern was free of the peaks characteristic of crystalline atorvastatin free acid, as illustrated in FIG. 16, and was thus, non-crystalline.

Figure 18:
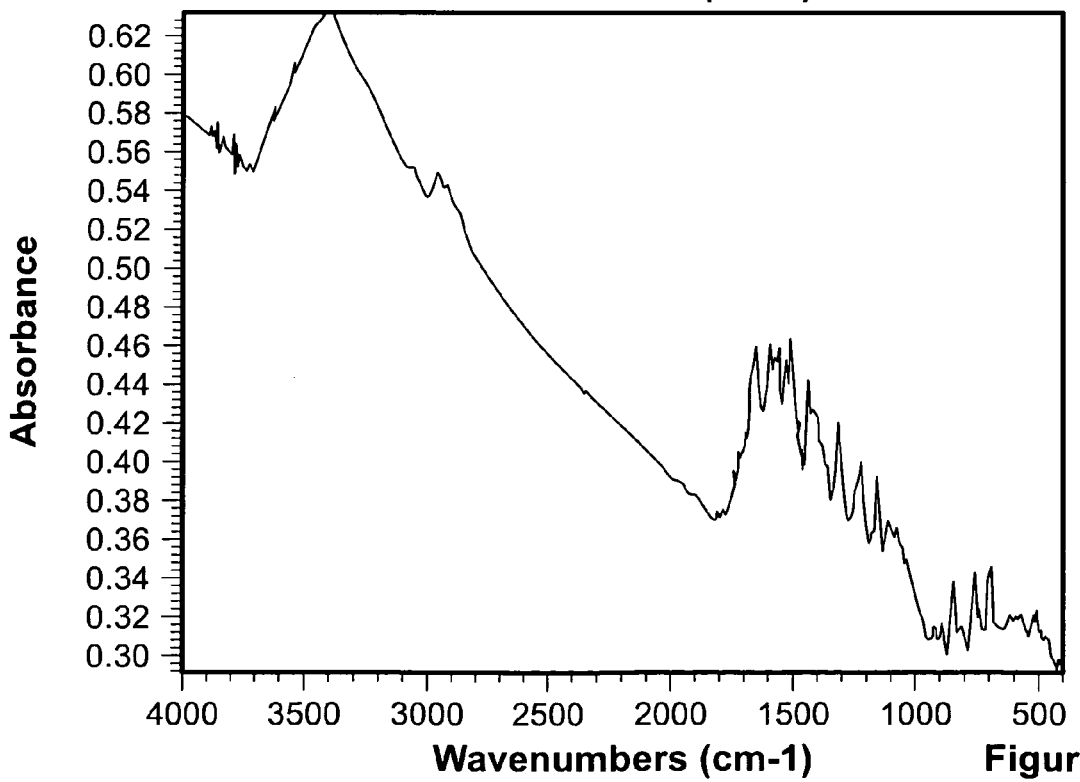
FIG. 18 illustrates the FTIR spectrum a sample of atorvastatin free acid treated with the process of the invention.

The non-crystalline atorvastatin free acid prepared with the process of the invention was then analyzed with FTIR spectroscopy. The resulting FTIR spectrum is illustrated in FIG. 18. A comparison of the FTIR spectrum illustrated in FIG. 18 with that of the crystalline atorvastatin free acid illustrated in FIG. 17, confirms that the treated atorvastatin free acid is the same chemical entity as the crystalline atorvastatin free acid. The FTIR spectrum of atorvastatin free acid reference exhibits somewhat sharper peaks than the spectrum of the non-crystalline laser treated atorvastatin free acid. However, as discussed above, broadening of the FTIR spectroscopic absorption bands is typical of the non-crystalline compared to the crystalline form of a material because of increased freedom of movement of molecules not confined to a crystal lattice.

Comparative Example

Atorvastatin Free Acid

Figure 59:
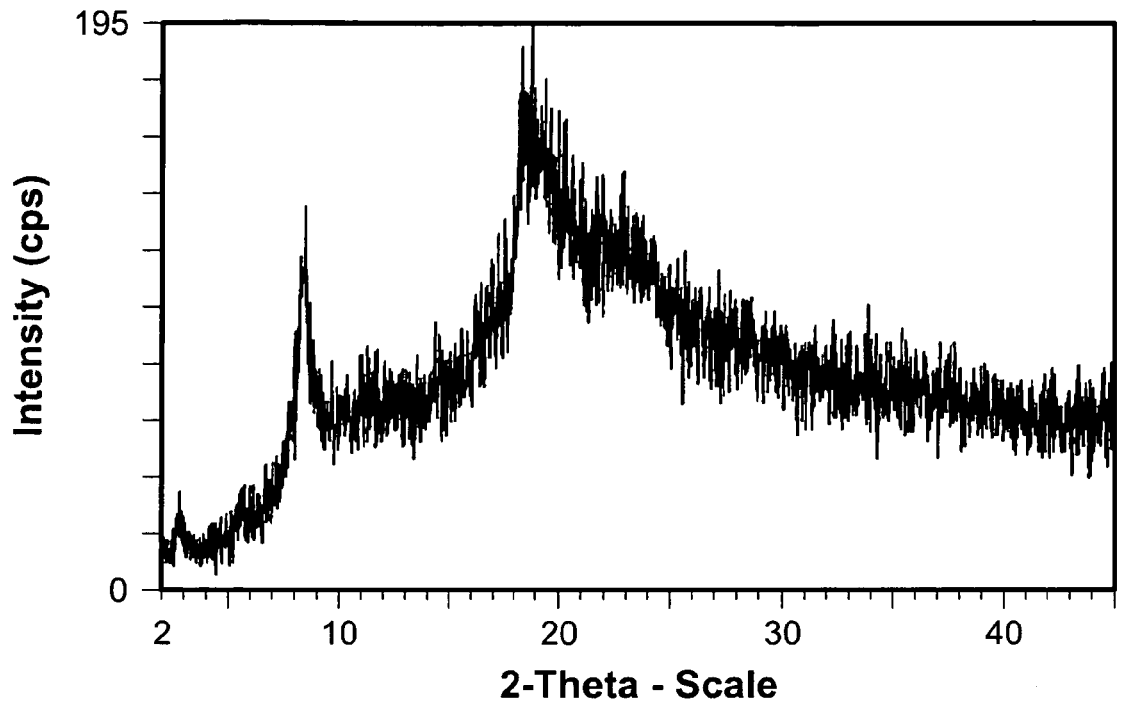
FIG. 59 illustrates the PXRD pattern for a sample of crystalline atorvastatin free acid formed in the process of the invention, with the exception that laser radiation was not applied.

The protocol of Example 4 was repeated with the exception that there was no application of laser radiation. The resulting material was visibly crystalline, which was confirmed by PXRD analysis, which demonstrated that a substantial amount of crystalline material was present. A PXRD pattern for the atorvastatin free acid obtained without the application of the laser radiation is illustrated in FIG. 59. The PXRD pattern of FIG. 59 has the same peaks as that of the control sample illustrated in FIG. 15. An FTIR analysis of the resulting atorvastatin free acid was also performed, confirming the material was atorvastatin free acid. The results demonstrate that the non-crystalline atorvastatin free acid is not an artifact of the experiment, but, instead, is a direct result of the application of the laser radiation in the process of the invention.

Example 5

Preparation of Non-Crystalline Atorvastatin Calcium

The initial development of atorvastatin for its cholesterol lowering benefits was performed for atorvastatin as an amorphous solid state, designated as Form 23 or amorphous B. When the crystalline form of atorvastatin calcium was developed, clinical trials had already been completed for Form 23 with very favorable results. Although bioequivalence testing showed a difference in absorption for tablets prepared with Form 23 compared to those made with the crystalline compound, the extent of the absorption proved sufficiently equivalent for regulatory approval of the clinical use of the crystalline form. While atorvastatin calcium has been produced in non-crystalline forms, the present method offers advantages both in production methods and the non-crystalline state generated compared to the prior methods, reopening the potential for use of this more soluble and rapidly absorbable form.

Figure 19:
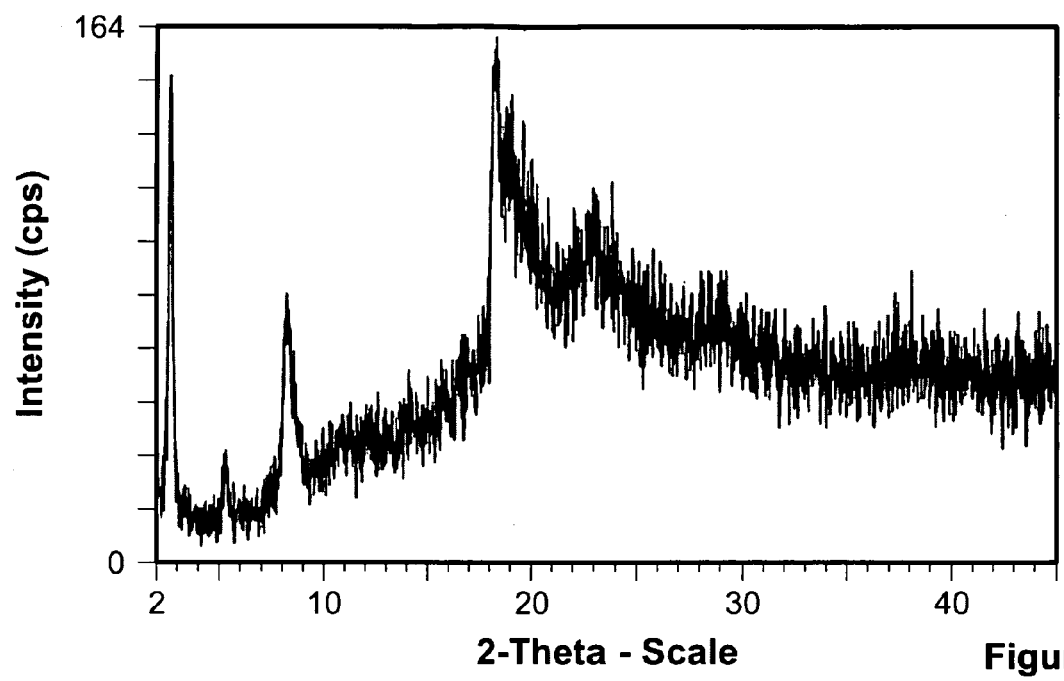
FIG. 19 illustrates the PXRD pattern of a sample of crystalline atorvastatin calcium.
Figure 21:
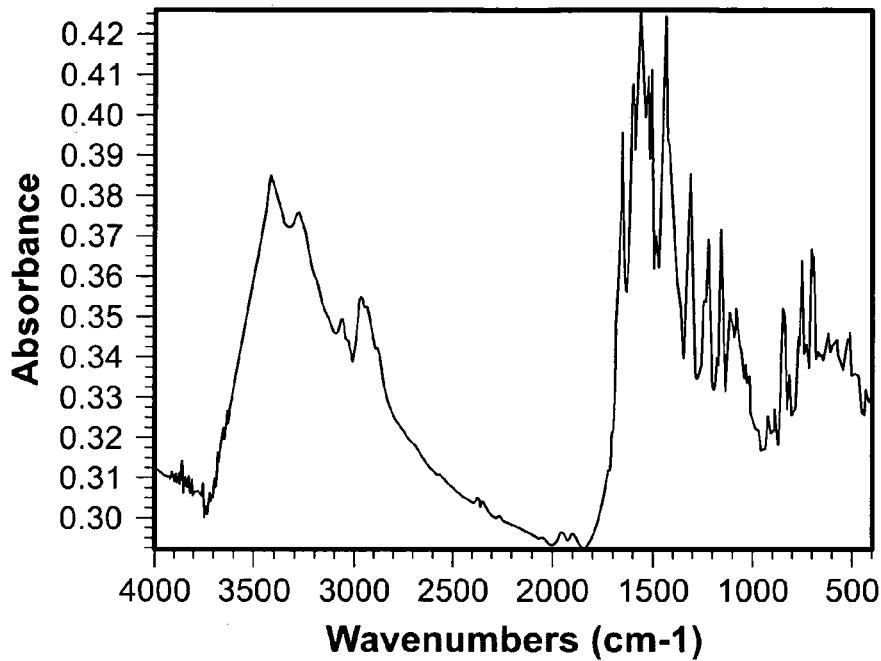
FIG. 21 illustrates the FTIR spectrum of a sample of crystalline atorvastatin calcium.

A control sample of the reference crystalline atorvastatin calcium was analyzed with PXRD and FTIR spectroscopy. The PXRD spectrum of the crystalline atorvastatin calcium was characterized by the PXRD peaks typical of the crystalline form, and is illustrated in FIG. 19. The FTIR spectrum of crystalline atorvastatin calcium is illustrated in FIG. 21.

A 10 mg sample of crystalline atorvastatin calcium was dissolved in 444 mg of absolute ethanol by heating to 160° C. while stirring at 9000 rpm for 11 minutes. The solution was transferred into a 60 mm×15 mm glass Petri dish, covered with a glass lid, and placed on a hotplate at 100° C.

Figure 20:
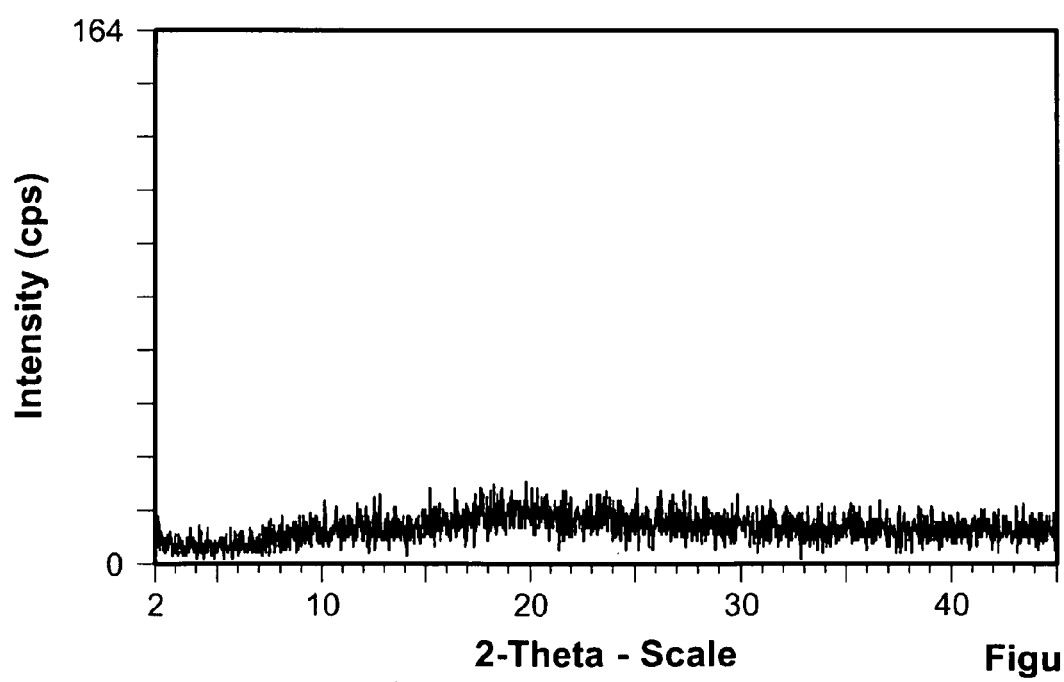
FIG. 20 illustrates the PXRD pattern of a sample of atorvastatin calcium treated with the process of the invention.

The amplitude modulated emission of a diode laser having a central wavelength of 408 μm wavelength was applied to the solution for 1 minute. Then, The amplitude modulated emission of a diode laser having a central wavelength of 674 nm was applied for 1 minute, followed by another cycle of amplitude modulated laser light at 408 nm wavelength for 1 minute, then with 674 μm wavelength for 1 minute, followed by a final cycle of amplitude modulated laser light at 408 nm wavelength for 30 seconds, then with 674 nm wavelength for 30 seconds. During these cycles, the sample was rotated slowly through each of the approximately 3 cm diameter expanded beams at a distance of 25 cm from the respective Strachan Devices. The 408 nm beam had a peak power of 2.44 mW after passing through a Thorlabs 5× beam expander and the Strachan Device. The output of the 408 nm beam was optically phase cancelled using the Strachan Device to achieve a measured 80 percent reduction of transmitted power to 0.48 mW over a 3 cm diameter beam. The 674 nm laser diode beam was passed through a Thorlabs 5× beam expander and the Strachan Device. Using the Strachan Device, the 674 nm beam was adjusted to the 80 percent phase cancellation level to achieve a power of approximately 0.48 mW over the 3 cm diameter beam. Both beams were electronically amplitude modulated at 6.25 MHz After the sequenced laser treatment, the lid of the glass Petri dish was removed, and the solution allowed to dry through slow evaporation at a room temperature of about 19 to 20° C. and 32 percent humidity. The resultant material dried to a transparent glass state. The laser treated atorvastatin calcium was then studied using PXRD, and found to be non-crystalline. The PXRD pattern is illustrated in FIG. 20.

Figure 22:
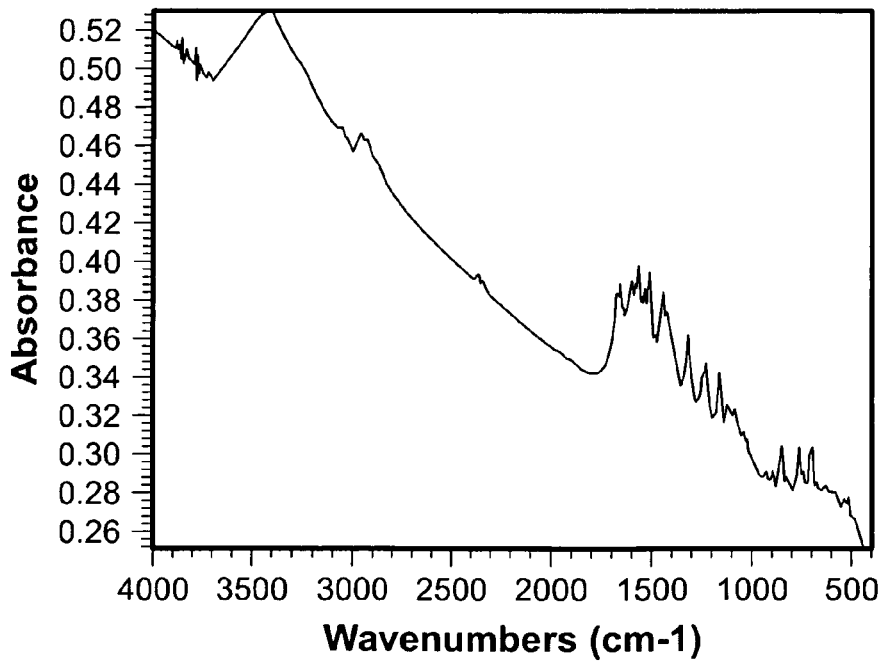
FIG. 22 illustrates the FTIR spectrum of a sample of atorvastatin calcium treated with the process of the invention.

The non-crystalline laser treated atorvastatin calcium was then analyzed with FTIR spectroscopy. The FTIR spectrum obtained is illustrated in FIG. 22. A comparison of the FTIR spectrum of the non-crystalline atorvastatin calcium with the FTIR spectrum of crystalline atorvastatin calcium, illustrated in FIG. 21, demonstrates that the laser treated material is atorvastatin calcium. The FTIR spectrum of the non-crystalline laser treated atorvastatin calcium exhibits some broadening of the peaks compared to the spectrum of the crystalline atorvastatin calcium, as expected for the non-crystalline versus crystalline form of a compound.

Figure 23:
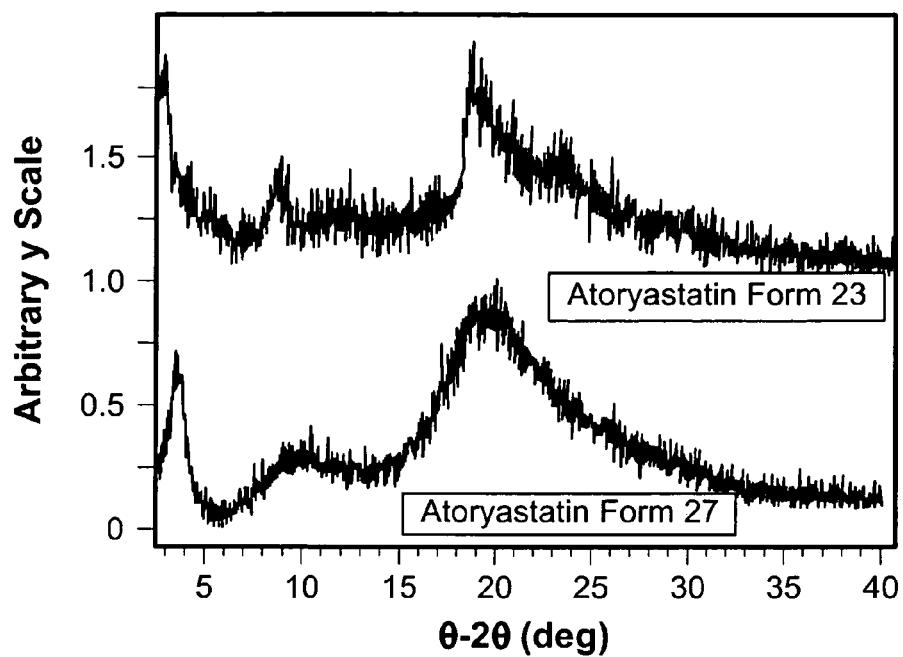
FIG. 23 illustrates the PXRD patterns comparing amorphous atorvastatin calcium Form 23 to Form 27.
Figure 24:
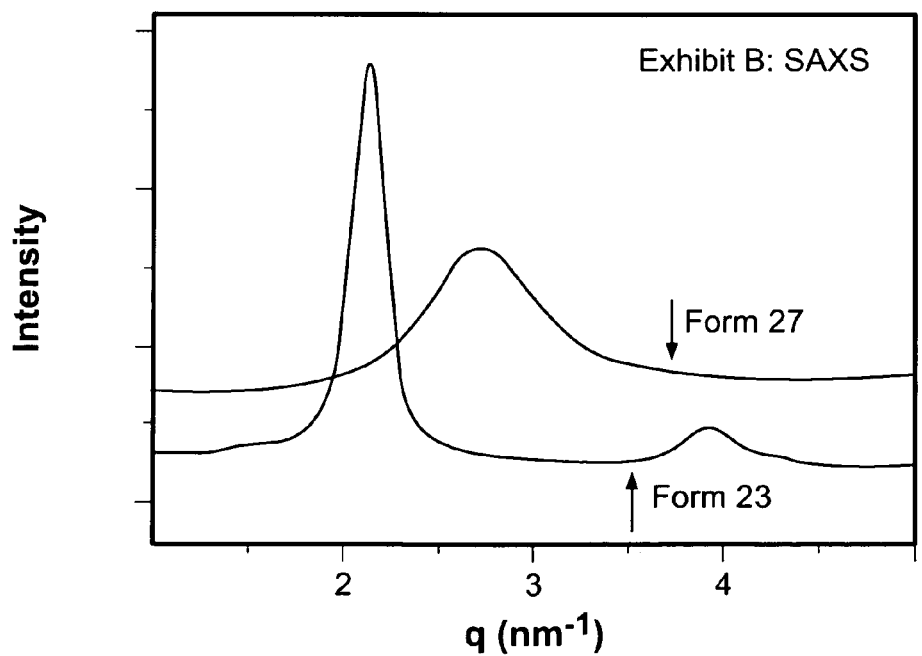
FIG. 24 illustrates the small angle X-ray scattering (SAXS) patterns comparing amorphous atorvastatin calcium Form 23 to Form 27.

Prior studies with atorvastatin calcium have made distinctions between the non-crystalline states of this compound produced through different methods. While Form 23 was the form originally tested by the original innovator, the most common non-crystalline form produced in other labs is known as Form 27. FIG. 23 compares the PXRD patterns of Form 23 and Form 27, and shows that their broad bands of reflection are somewhat different with Form 23 appearing more crystalline. This impression is further confirmed with small angle X-ray scattering (SAXS) shown in FIG. 24, demonstrating that Form 23 is more ordered. The PXRD of the sequenced laser treated atorvastatin calcium shown in FIG. 20 has a pattern that differs from the patterns obtained from Forms 23 and 27, suggesting it has the lowest level of residual crystallinity of any of the forms examined.

Solubility studies with Forms 23 and 27 showed that during the first hour of dissolution, the aqueous solubility of Form 23 was 3.2 times and that of Form 27 was 4.3 times that of commercial crystalline atorvastatin calcium. By virtue of further reductions in short range ordering, the highly non-crystalline glass form laser treated atorvastatin calcium is predicted to show a further increment in solubility and bioavailability over these two forms. This increment offers the advantage of potential dose reduction with maintenance or augmentation of desired clinical effects and reduction or elimination of adverse effects.

Further advantages of this method of producing highly non-crystalline glass atorvastatin calcium over other methods includes applying only very low energies in acoustic resonance with the system to reduce the tendency to thermal degradation or instability of the compound and not requiring the use of environmentally toxic, harsh, or expensive solvents. Residual solvent in the solid state would pose essentially no health risk compared to other solvents in commercial use. Once desolvation occurs, the transparent glass state appears to be very stable with negligible observed tendency to recrystallization, increasing the practicality of large scale production and distribution.

Comparative Example

Atorvastatin Calcium

Figure 60:
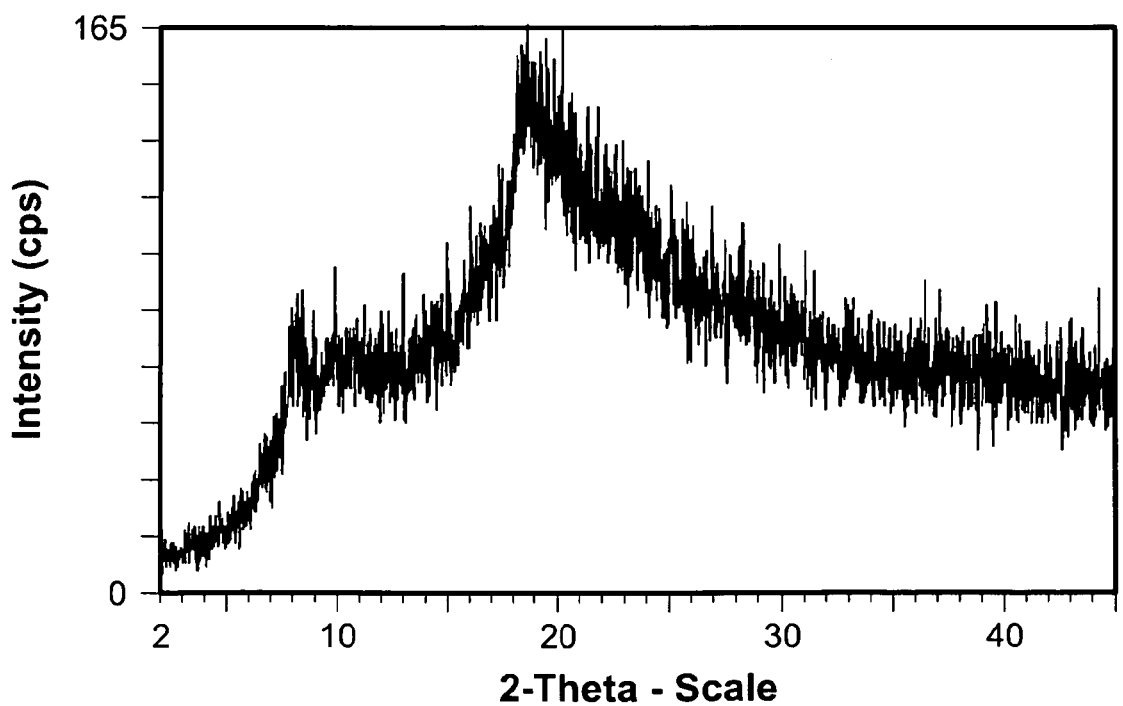
FIG. 60 illustrates the PXRD pattern for a sample of crystalline atorvastatin calcium formed in the process of the invention, with the exception that laser radiation was not applied.

The protocol of Example 5 was repeated with the exception that there was no application of laser radiation. The resulting material was visibly crystalline, which was confirmed by PXRD analysis, which demonstrated that a substantial amount of crystalline material was present. A PXRD pattern for the atorvastatin calcium obtained without the application of the laser radiation is illustrated in FIG. 60. The PXRD pattern of FIG. 60 has the same peaks as that of the control sample illustrated in FIG. 19. An FTIR analysis of the resulting atorvastatin calcium was also performed, confirming the material was atorvastatin calcium. The results demonstrate that the non-crystalline atorvastatin calcium is not an artifact of the experiment, but, instead, is a direct result of the application of the laser radiation in the process of the invention.

Example 6

Preparation of Non-Crystalline Rosuvastatin Calcium

Figure 25:
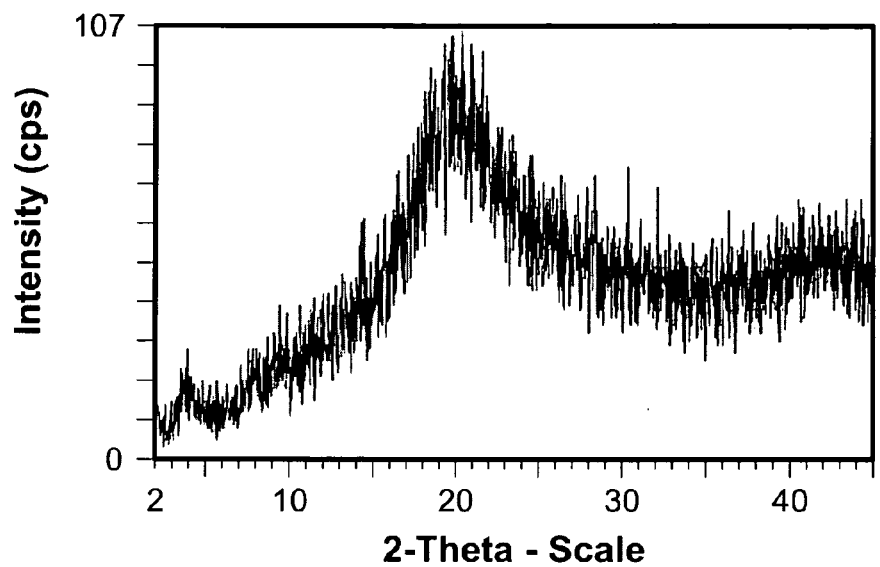
FIG. 25 illustrates the PXRD pattern of a reference sample of rosuvastatin calcium.
Figure 27:
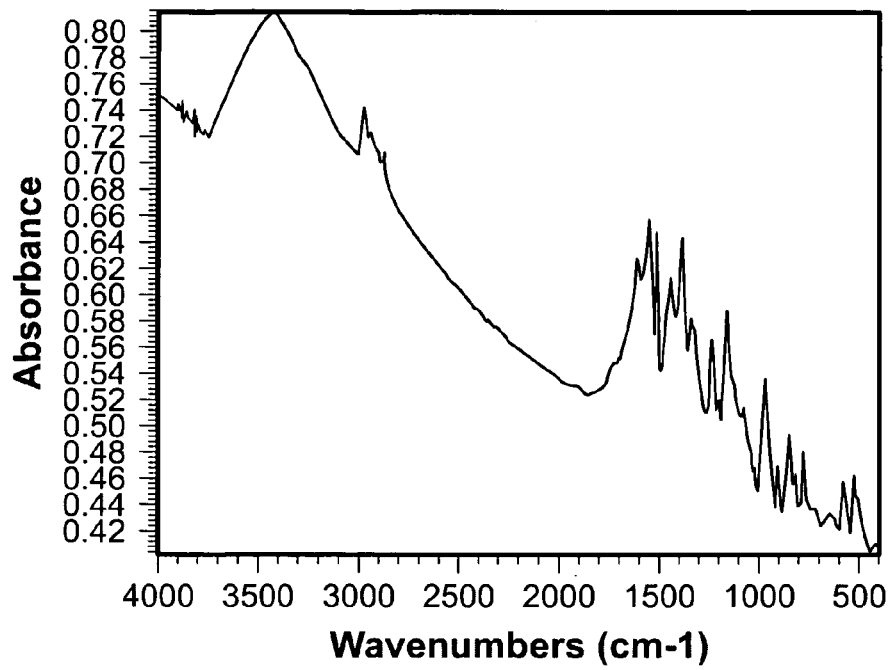
FIG. 27 illustrates the FTIR spectrum of the reference sample of rosuvastatin calcium.

A control sample of reference standard rosuvastatin calcium was analyzed with PXRD and FTIR spectroscopy. The PXRD spectrum obtained from the sample had the broad bands of reflection characteristic of currently produced amorphous rosuvastatin calcium, and is illustrated in FIG. 25. The FTIR spectrum obtained from the sample of rosuvastatin calcium is illustrated in FIG. 27.

A 10 mg sample of rosuvastatin calcium reference compound was dissolved in 530 mg of absolute ethanol by heating to 160° C. while stirring at 9000 rpm for 12.5 minutes. The solution was transferred into a 60 mm×15 mm glass Petri dish, covered with a glass lid, and placed on a hotplate at 95° C.

Figure 26:
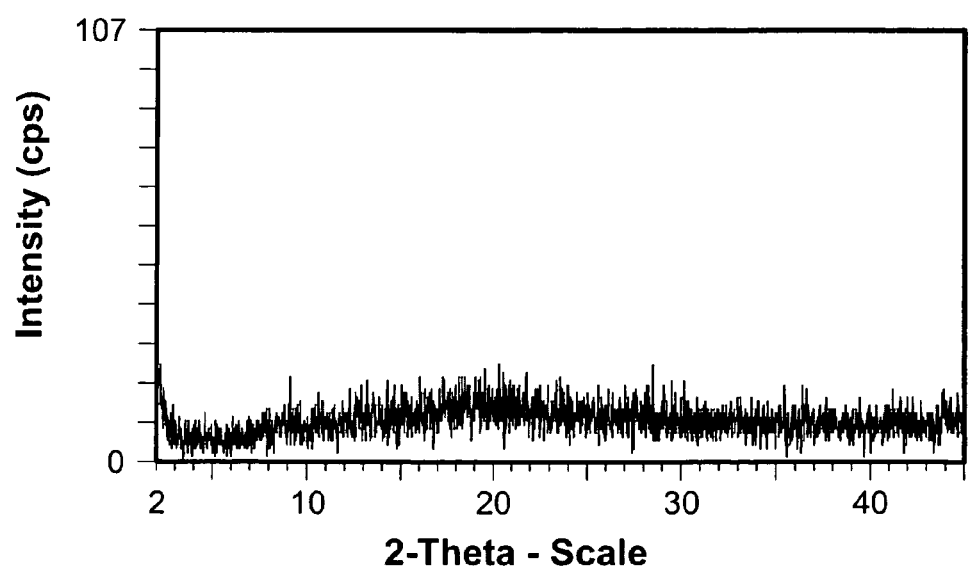
FIG. 26 illustrates the PXRD pattern of rosuvastatin calcium treated with the process of the invention.

First, amplitude modulated diode laser light having a central wavelength of about 408 nm was applied to the solution of rosuvastatin calcium for 1 minute. Then amplitude modulated diode laser light having a central wavelength of about 674 nm was applied to the solution of rosuvastatin calcium for 1 minute. Those cycles were then followed by another cycle of amplitude modulated laser light at 408 μm wavelength for 1 minute, then another cycle of amplitude modulated laser light with 674 nm wavelength for 1 minute, followed by a final cycle of amplitude modulated laser light at 408 nm wavelength for 30 seconds, then with another cycle of amplitude modulated laser light at 674 μm wavelength for 30 seconds. During these cycles, the sample was rotated slowly through each of the approximately 3 cm diameter expanded beams at a distance of 25 cm from the respective Strachan Devices. The emission from the 408 μm diode laser had a peak power of 2.17 mW after passing through a Thorlabs 5× beam expander and the Strachan Device. The output of the 408 μm beam was optically phase cancelled using the Strachan Device to achieve a measured 80 percent reduction of transmitted power to 0.42 mW over a 3 cm beam. The emission from the 674 nm diode laser was passed through a Thorlabs 5× beam expander and the Strachan Device. Using the Strachan Device, the 674 μm beam was adjusted to the 80 percent phase cancellation level to achieve a power of approximately 0.48 mW over a 3 cm beam. Both beams were electronically amplitude modulated at 6.25 MHz After the sequenced laser treatment the lid of the glass Petri dish was removed, and the solution allowed to dry through slow evaporation at a room temperature of about 20° to 21° C. and about 35 percent humidity. The resultant material dried to a transparent glass state. A PXRD analysis of the laser treated rosuvastatin illustrated in FIG. 26 is free of PXRD peaks characteristic of a crystalline compound, confirming that that the laser treated rosuvastatin calcium is non-crystalline.

Figure 28:
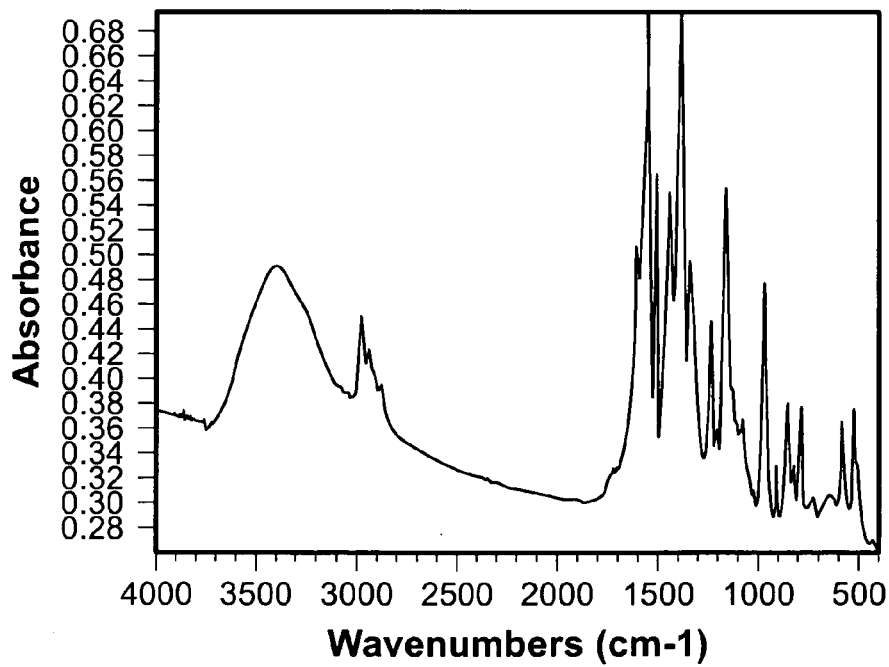
FIG. 28 illustrates the FTIR spectrum of rosuvastatin treated with the process of the invention.

An FTIR spectrum of the laser treated rosuvastatin calcium spectroscopy is illustrated in FIG. 28. A comparison of the FTIR spectrum of the laser treated rosuvastatin calcium with that of the reference solid state rosuvastatin calcium shown in FIG. 27 confirms that the laser treated material is rosuvastatin calcium.

Comparing the PXRD patterns of solid state rosuvastatin calcium to laser treated rosuvastatin, the broad reflection bands observed in solid state rosuvastatin calcium are blunted or absent in laser treated rosuvastatin, suggesting an even greater reduction of short range ordering in laser treated rosuvastatin As in the discussion for laser treated atorvastatin calcium, the reduced residual crystallinity of laser treated rosuvastatin calcium compared to untreated rosuvastatin calcium predicts that laser treated rosuvastatin calcium will be more soluble and bioavailable than currently produced solid state rosuvastatin calcium, though further testing is required to determine whether this is sufficient to be clinically significant with respect to compound performance.

Example 7

Preparation of Co-Amorphous Ezetimibe/Simvastatin

Figure 11:
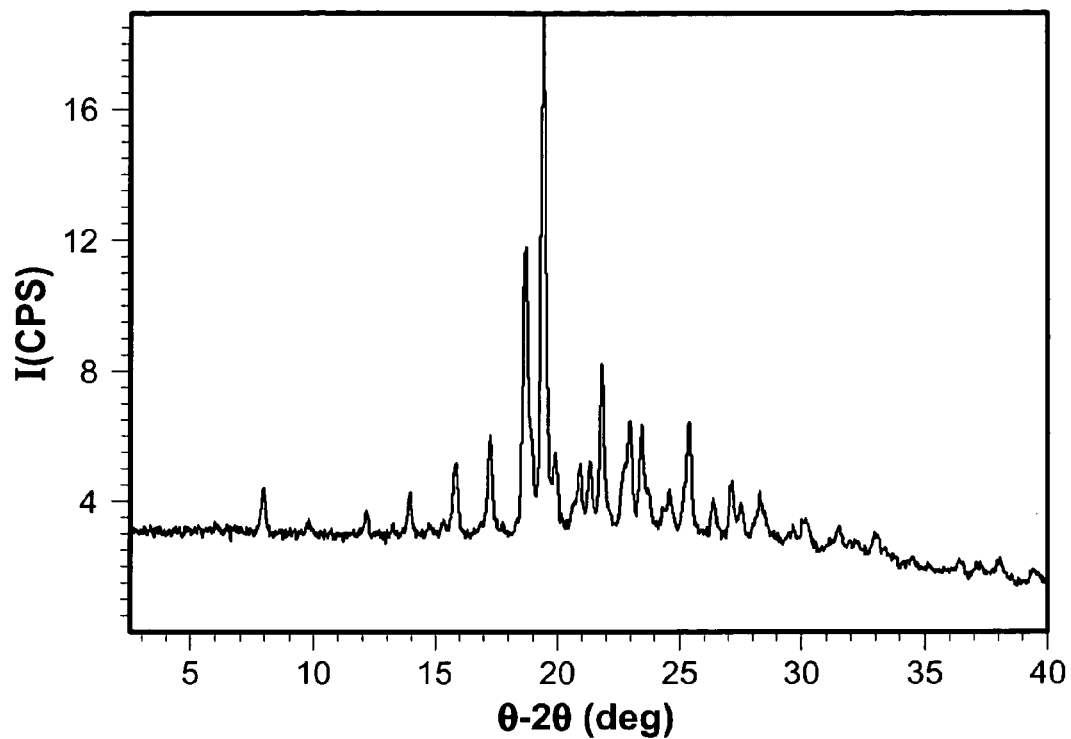
FIG. 11 illustrates the PXRD pattern of a sample of crystalline ezetimibe.

Highly intermixed non-crystalline blends of two of more compounds into a co-amorphous glass state have been produced with the laser treatment of the present invention. Comparative data for interpretation of results for the co-amorphous combinations was obtained from the PXRD and FTIR analysis of separate untreated reference samples of each of the ezetimibe and simvastatin and separate samples of ezetimibe and simvastatin treated with the process of the invention. The PXRD pattern of the reference sample of crystalline ezetimibe, having the characteristic PXRD peaks of a crystalline compound, is illustrated in FIG. 11, and the PXRD pattern of non-crystalline, laser treated ezetimibe is illustrated in FIG. 13. The PXRD pattern of the reference sample of crystalline simvastatin is illustrated in FIG. 7, and the PXRD pattern of laser treated non-crystalline simvastatin is illustrated in FIG. 9.

The FTIR spectrum of the reference sample of crystalline ezetimibe is illustrated in FIG. 12 with the FTIR spectrum of the non-crystalline laser treated ezetimibe. The FTIR spectrum of the reference sample of crystalline simvastatin is illustrated in FIG. 8, and the FTIR spectrum of the non-crystalline laser treated simvastatin is illustrated in FIG. 10. As the PXRD pattern of a compound in the non-crystalline state results in disappearance of characteristic deflection peaks, FTIR spectroscopy allows compound identification and provides further evidence of the non-crystalline state by showing a broadening of absorption bands that occurs in the non-crystalline compared to the crystalline state.

Co-amorphous samples of ezetimibe and simvastatin were prepared with the process of the invention with ezetimibe: simvastatin weight ratios of 1:1, 1:2, 1:4, and 1:8.

For an ezetimibe:simvastatin weight ratio of 1:1, 20 mg of crystalline ezetimibe and 20 mg sample of crystalline simvastatin were dissolved in 753 mg of absolute ethanol by stirring at 9000 rpm with a magnetic stirrer for 7.5 minutes, followed by stirring at 9000 rpm for an additional 11 minutes on a heated plate at 140° C. The solution was cooled to 20° C., and then filtered using a syringe to remove any residual crystals. Half of the solution was then decanted into a 60 mm×15 mm glass Petri dish covered with a glass lid to provide approximately 10 mg of ezetimibe and 10 mg of simvastatin in this sample.

For an ezetimibe:simvastatin weight ratio of 1:2, 10 mg of control crystalline ezetimibe and 20 mg of crystalline simvastatin were dissolved in 698 mg of absolute ethanol, and stirred at 9000 rpm with a magnetic stirrer for 8 minutes, followed by stirring at 9000 rpm for an additional 10 minutes on a heated plate at 140° C. The solution was cooled to approximately 20° C., and then filtered using a syringe to remove any residual crystals. Half of the solution was then decanted into a 60 mm×15 mm glass Petri dish covered with a glass lid.

For an ezetinibe:simvastatin weight ratio of 1:4, 5 mg of crystalline ezetimibe and 20 mg crystalline simvastatin were dissolved in 663 mg of absolute ethanol, and stirred at 9000 rpm for 8 minutes, followed by stirring at 9000 rpm for an additional 10 minutes on a heated plate at 140° C. The solution was cooled to approximately 20° C., and then filtered using a syringe to remove any residual crystals. Half of the solution was then decanted into a 60 mm×15 mm glass Petri dish covered with a glass lid For an ezetinibe:simvastatin weight ratio of 1:8, 2.5 mg of crystalline ezetimibe and 20 mg crystalline simvastatin were dissolved in 502 mg of absolute ethanol, and stirred at 9000 rpm for 3 minutes, followed by stirring at 9000 rpm for an additional 11 minutes on a heated plate at 140° C. The solution was cooled to approximately 20° C., and then filtered using a syringe to remove any residual crystals. Half of the solution was then decanted into a 60 mm×15 mm glass Petri dish covered with a glass lid Those ezetimibe/simvastatin samples, having ezetimibe/simvastatin rations of 1:1, 1:2, 1:4, and 1:8, were first treated with amplitude modulated laser radiation from a diode laser having a central wavelength of about 674 nm wavelength for 2.5 minutes, and then with amplitude modulated laser radiation from a diode laser having a central wavelength of about 408 nm for 2.5 minutes, rotating the sample slowly through each of the approximately 3 cm diameter expanded beams at a distance of 25 cm from the respective Strachan Devices. The 674 nm laser diode beam was passed through a Thorlabs 5× beam expander and a Strachan Device. Using the Strachan Device, the 674 nm beam was adjusted to the 80 percent phase cancellation level to achieve a power of 0.48 mW over a 3 cm expanded beam. The 408 nm beam had a peak power of 0.10 mW after passing through a Thorlabs 5× beam expander and the Strachan Device. The output of the 408 nm beam was optically phase cancelled using the Strachan Device to achieve a measured 80 percent reduction of transmitted power to 0.02 mW over a 3 cm expanded beam. Both beams were electronically amplitude modulated at 6.25 Megahertz (MHz).

After the sequenced laser treatments of the solutions, the lids of the glass Petri dishes were removed and the solutions were allowed to dry through slow evaporation at a room temperature about of 20 to 21° C. and about 40 to 43 percent humidity. The resultant material for all four ezetimibe/simvastatin samples dried to a pure transparent glass state. The ezetimibe/simvastatin samples, having ezetimibe/simvastatin ratios of 1:1, 1:2, 1:4, and 1:8, were examined by polarizing light microscopy (PLM), and all were found to appear entirely isotropic, indicating that all the treated samples tested were non-crystalline, and, thus, co-amorphous.

Figure 29:
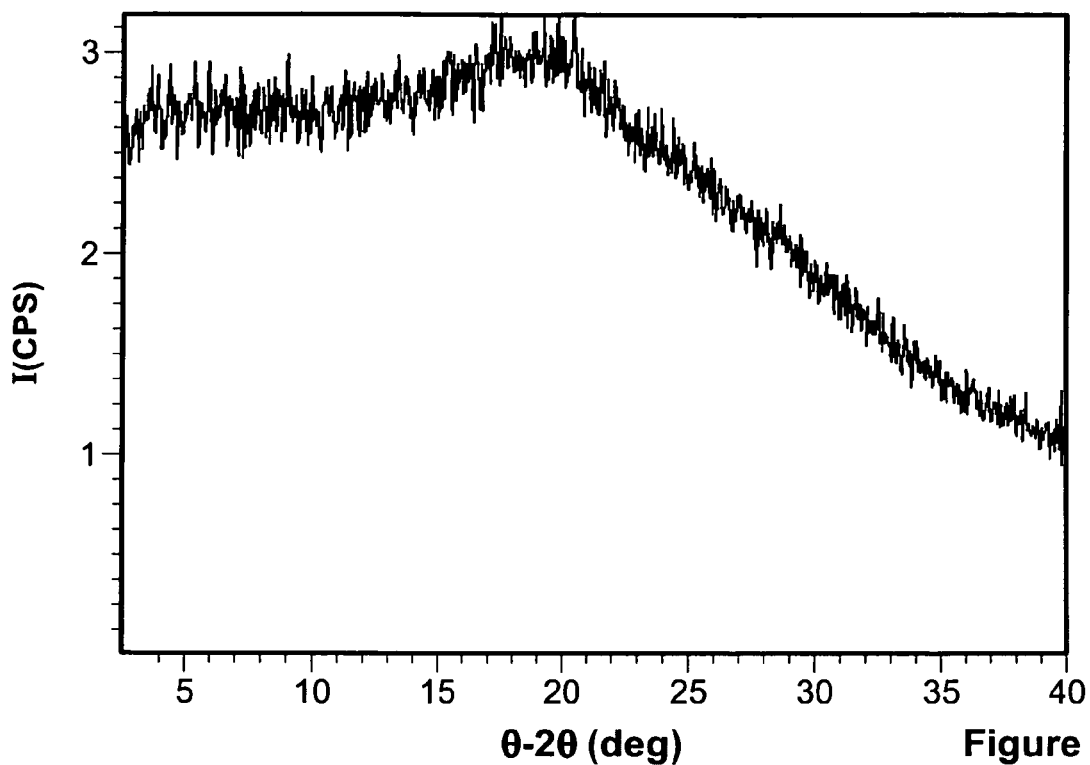
FIG. 29 illustrates the PXRD pattern of a laser treated sample of ezetimibe and simvastatin in a 1:1 ratio by weight.
Figure 30:
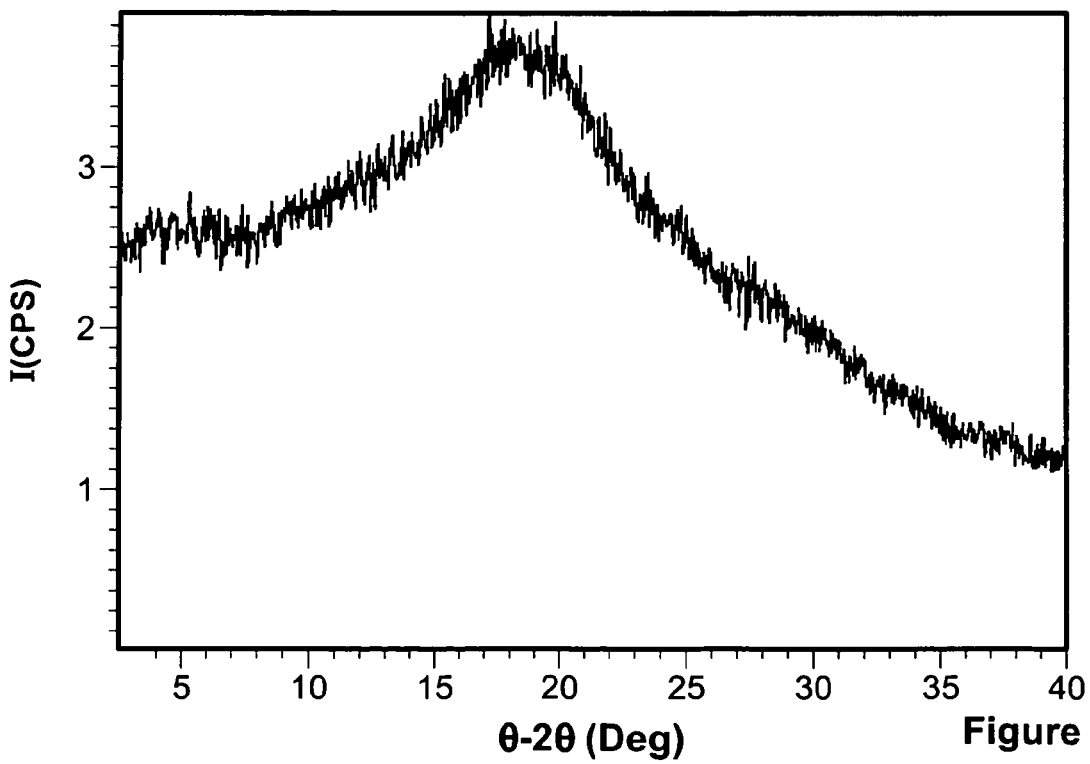
FIG. 30 illustrates the PXRD pattern of a laser treated sample of ezetimibe and simvastatin in a 10:20 ratio by weight.
Figure 31:
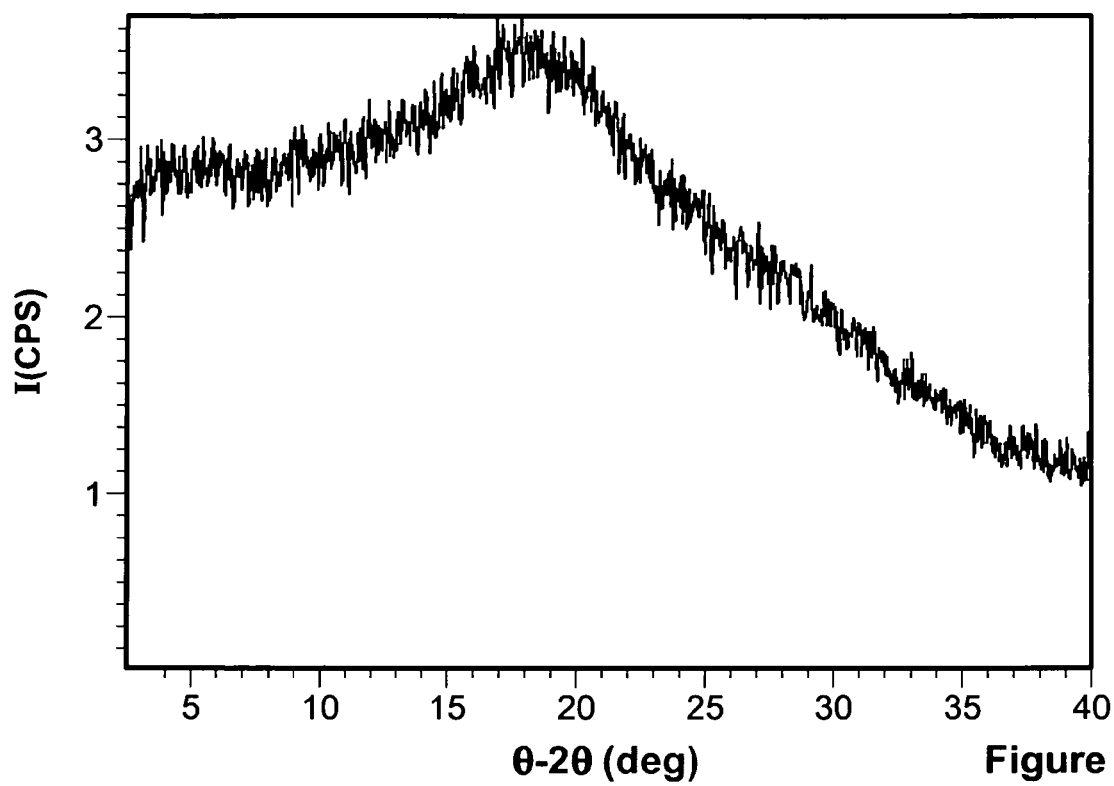
FIG. 31 illustrates the PXRD pattern of a laser treated sample of ezetimibe and simvastatin in a 10:40 ratio by weight.
Figure 32:
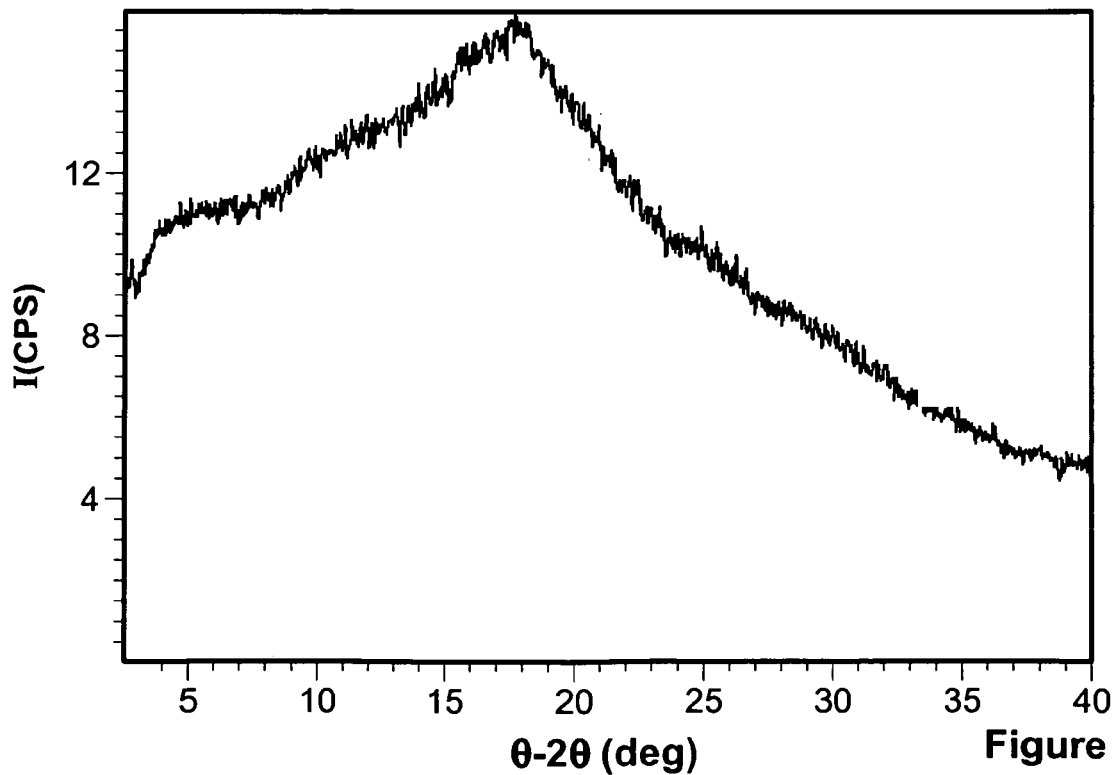
FIG. 32 illustrates the PXRD pattern of a laser treated sample of ezetimibe and simvastatin in a 10:80 ratio by weight.

FIG. 29 illustrates the PXRD pattern of the sample of laser treated ezetimibe/simvastatin in a 1:1 ratio by weight, demonstrating that the combination of ezetimibe and simvastatin is non-crystalline. FIG. 30 illustrates the PXRD pattern of the sample of laser treated ezetimibe/simvastatin in a 1:2 ratio by weight, demonstrating that the combination of ezetimibe and simvastatin is non-crystalline. FIG. 31 illustrates the PXRD pattern of the sample of laser treated ezetimibe/simvastatin in a 1:4 ratio by weight, demonstrating that the combination of ezetimibe and simvastatin is non-crystalline. FIG. 32 illustrates the PXRD pattern of the sample of laser treated ezetimibe/simvastatin in a 1:8 ratio by weight, demonstrating that the combination of ezetimibe and simvastatin is non-crystalline.

Thus, the process of the invention produced highly co-amorphous combinations of ezetimibe/simvastatin in all four of the currently clinically used weight ratios of 1:1, 1:2, 1:4, and 1:8.

The process was them repeated first treating the solutions of ezetimibe and simvastatin with the modified laser radiation from the 408 nm diode laser, followed by the modified laser radiation from the 674 nm diode laser. During these tests, the second half of the 1:1, 1:2, 1:4, and 1:8 weight ratio solutions described above were repeated with the reverse laser application protocol. The sequenced laser treatments were identical to those described above, except that the 2.5 minute application of the 408 nm diode laser was applied prior to the 2.5 minute application of the modified emission of the 674 nm laser diode.

Following the sequenced laser treatment, the lids of the glass Petri dishes were removed, and the solutions were allowed to dry through slow evaporation at a temperature of about 20° to about 22° C. and about 40 to 47 percent humidity. The resultant material for all four ezetimibe/simvastatin samples dried to a pure transparent glass state. The ezetimibe/simvastatin samples, in ratios of 1:1, 1:2, 1:4, and 1:8 were examined by polarizing light microscopy, and all were found to appear entirely isotropic, indicating that all the treated samples were co-amorphous.

Figure 33:
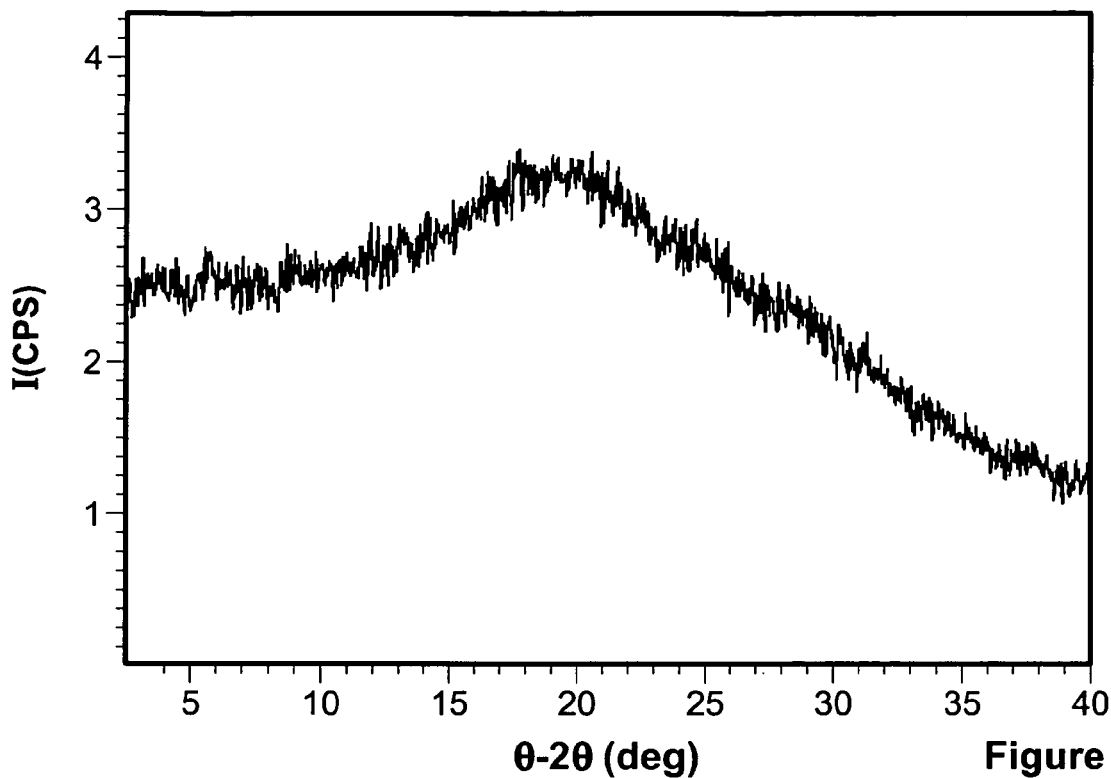
FIG. 33 illustrates the PXRD pattern of a laser treated sample of ezetimibe and simvastatin in a 1:1 ratio by weight with the order of the sequence of laser treatments reversed.
Figure 34:
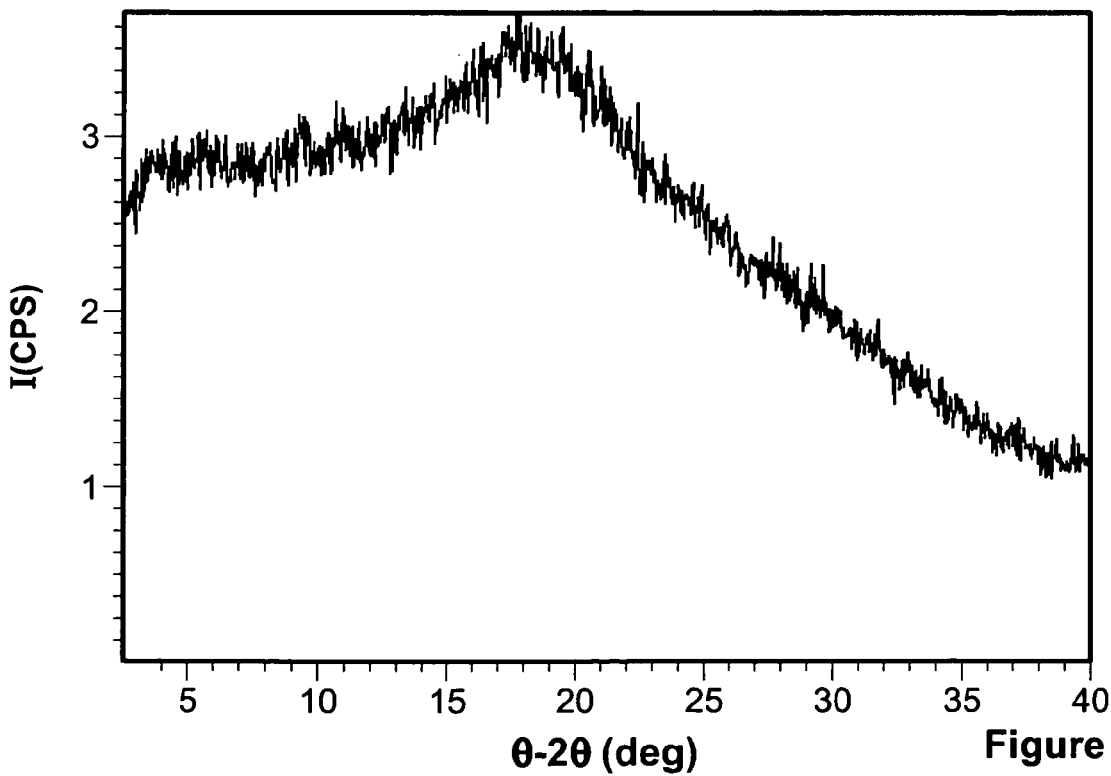
FIG. 34 illustrates the PXRD pattern of a laser treated sample of ezetimibe and simvastatin in a 10:20 ratio by weight with the order of the sequence of laser treatments reversed.
Figure 35:
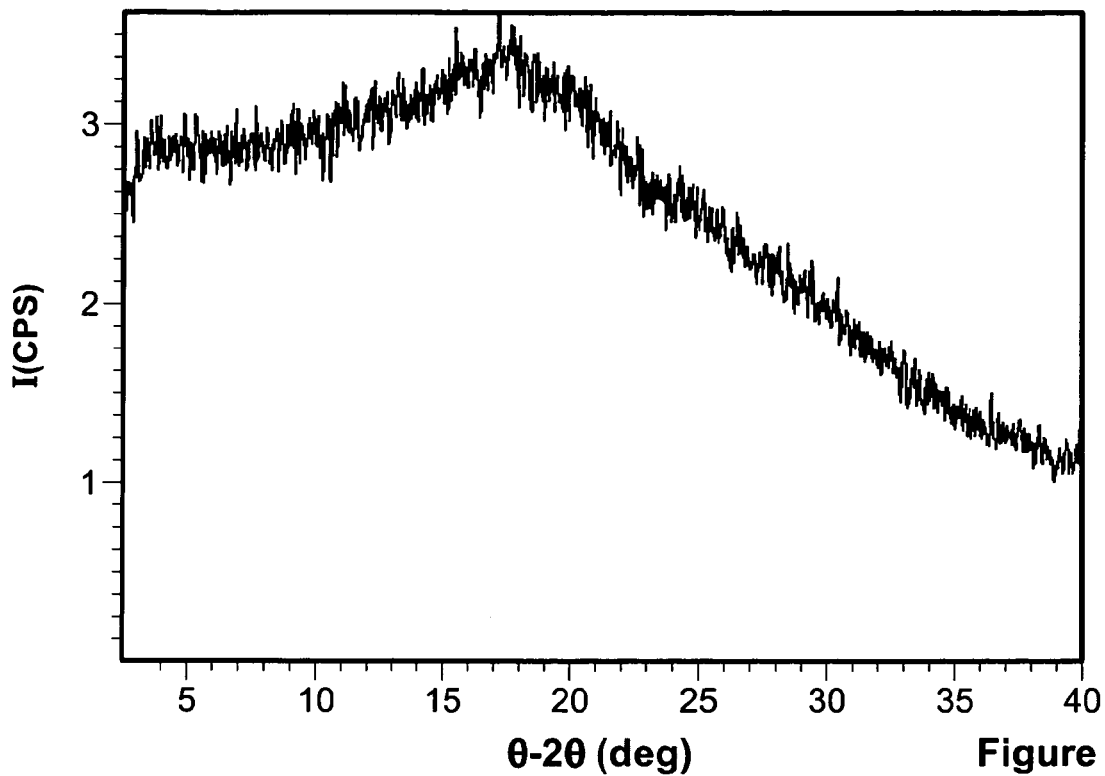
FIG. 35 illustrates the PXRD pattern of a laser treated sample of ezetimibe and simvastatin in a 10:40 ratio by weight with the order of the sequence of laser treatments reversed.
Figure 36:
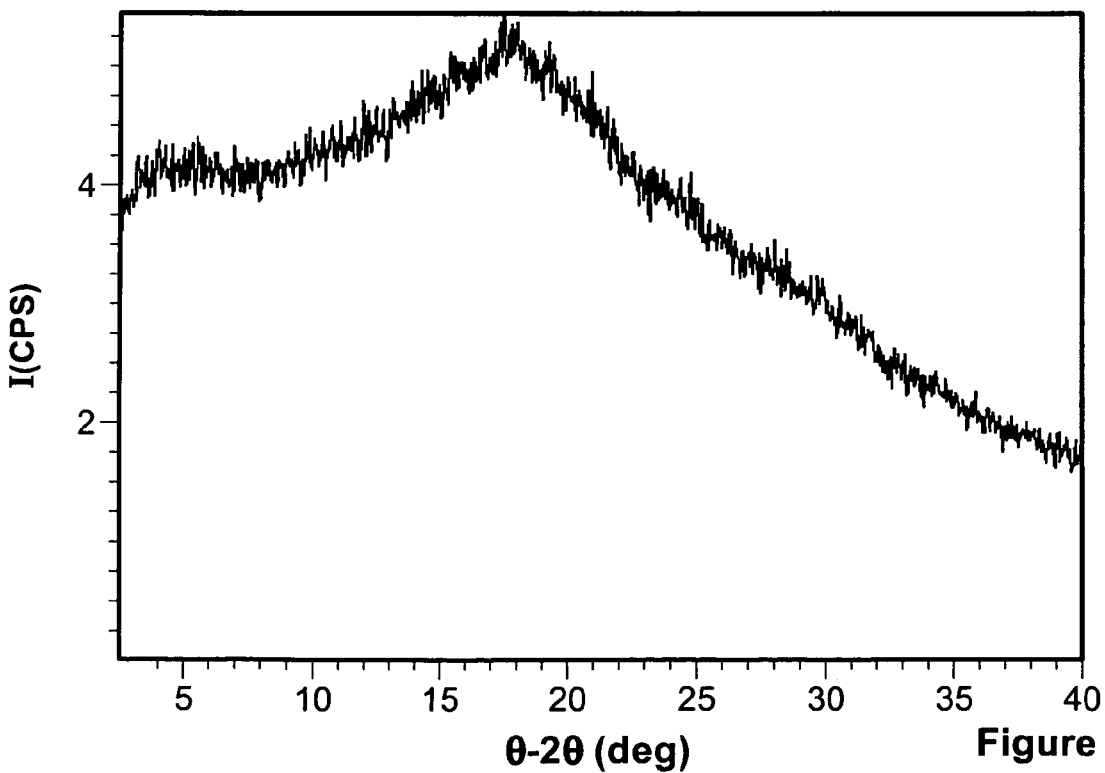
FIG. 36 illustrates the PXRD pattern of a laser treated sample of ezetimibe and simvastatin in a 10:80 ratio by weight with the order of the sequence of laser treatments reversed.
Figure 37:
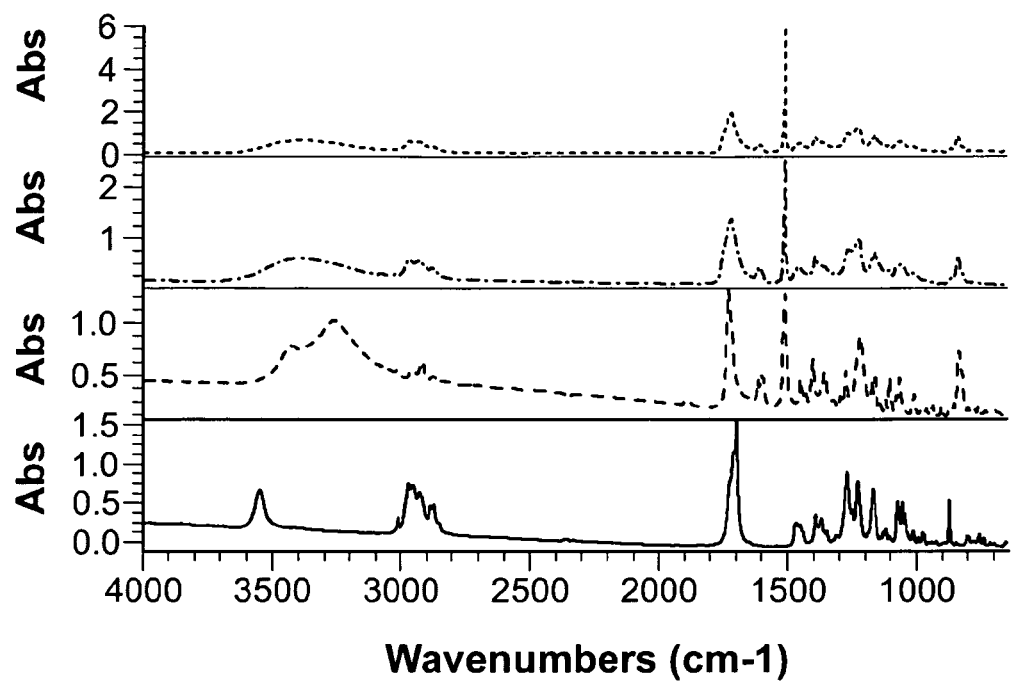
FIG. 37 illustrates a comparison of the FTIR spectrum of a laser treated sample of ezetimibe and simvastatin in a 1:1 ratio by weight to the FTIR spectrum of the reference sample.
Figure 38:
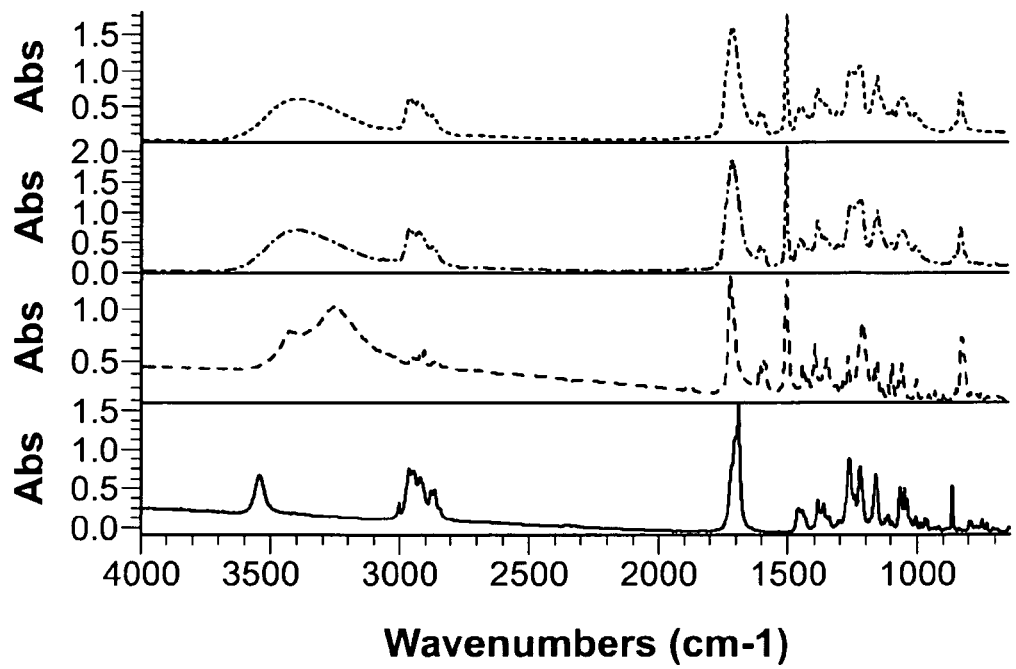
FIG. 38 illustrates a comparison of the FTIR spectrum of a laser treated sample of ezetimibe and simvastatin in a 10:20 ratio by weight to the FTIR spectrum of the reference sample.
Figure 39:
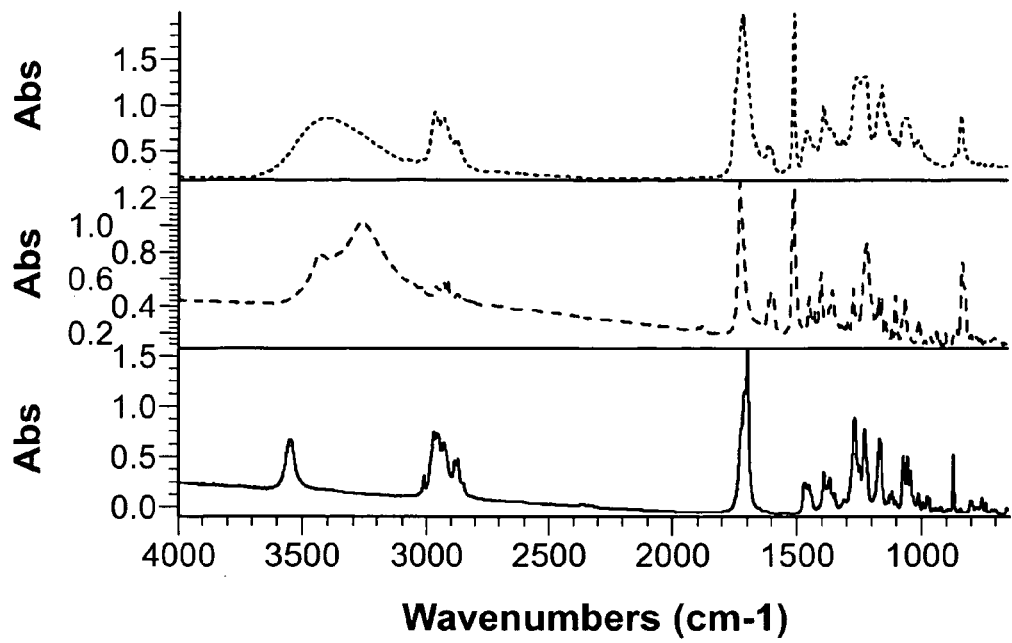
FIG. 39 illustrates a comparison of the FTIR spectrum of a laser treated sample of ezetimibe and simvastatin in a 10:40 ratio by weight to the FTIR spectrum of the reference sample.
Figure 40:
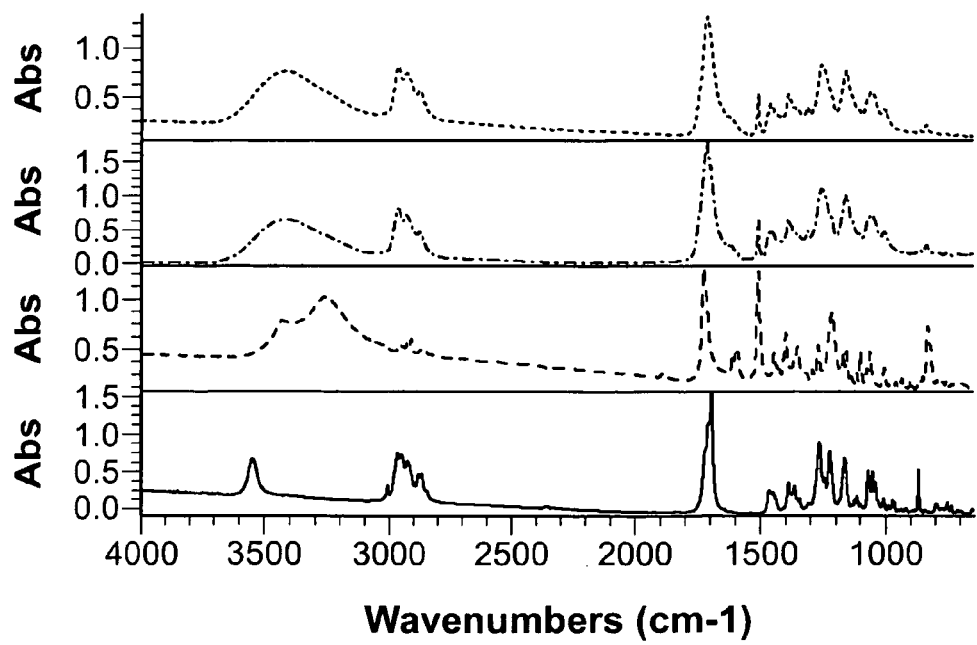
FIG. 40 illustrates a comparison of the FTIR spectrum of a laser treated sample of ezetimibe and simvastatin in a 10:80 ratio by weight to the FTIR spectrum of the reference sample.
Figure 41:
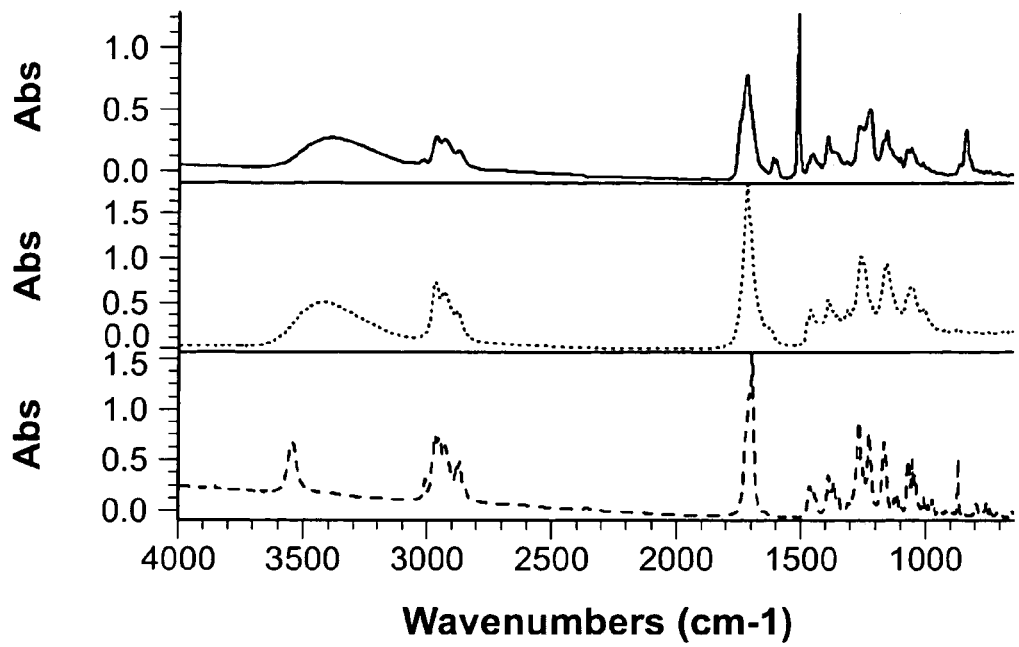
FIG. 41 illustrates a comparison of the FTIR spectrum of laser a treated sample of ezetimibe and simvastatin in a 1:1 ratio by weight with the sequence of laser treatment reversed to the FTIR spectrum of the reference sample.
Figure 42:
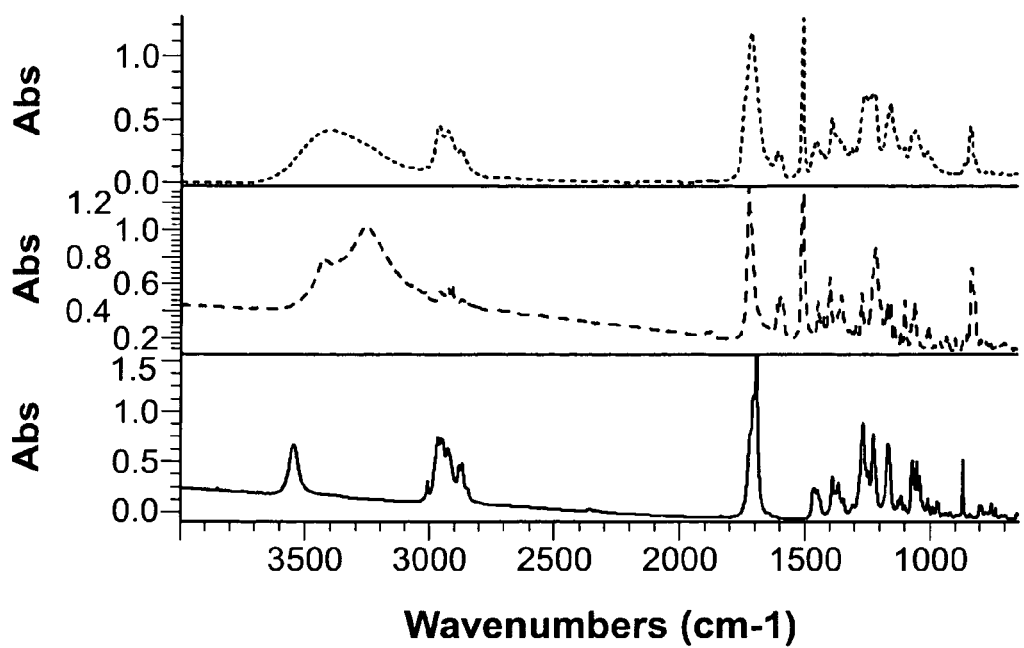
FIG. 42 illustrates a comparison of the FTIR spectrum of a laser treated sample of ezetimibe and simvastatin in a 10:20 ratio by weight with the sequence of laser treatment reversed to the FTIR spectrum of the reference sample.
Figure 43:
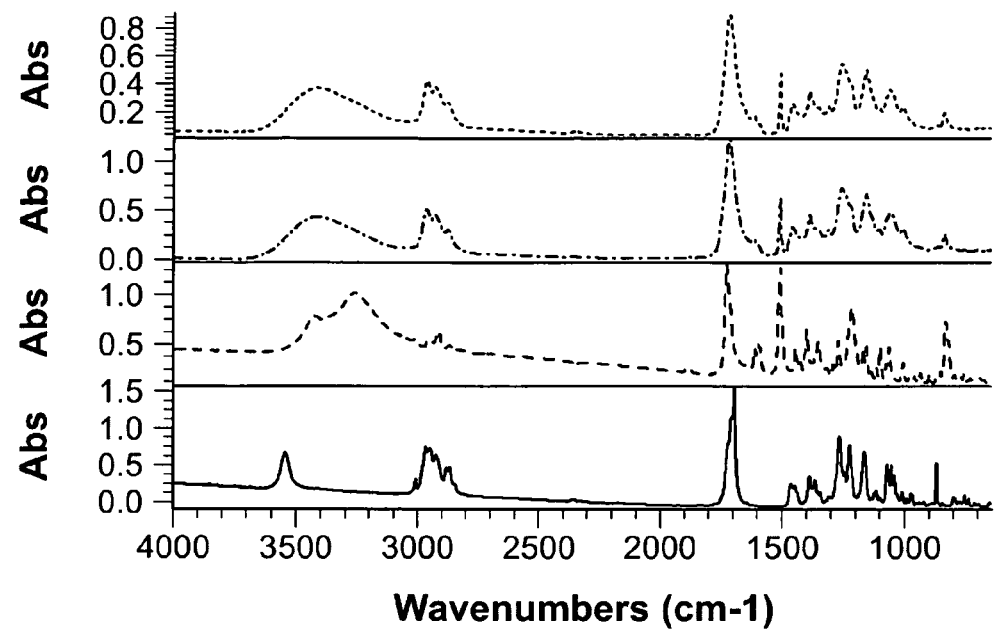
FIG. 43 illustrates a comparison of the FTIR spectrum of a laser treated sample of ezetimibe and simvastatin in a 10:40 ratio by weight with the sequence of laser treatment reversed to the FTIR spectrum of the reference sample.
Figure 44:
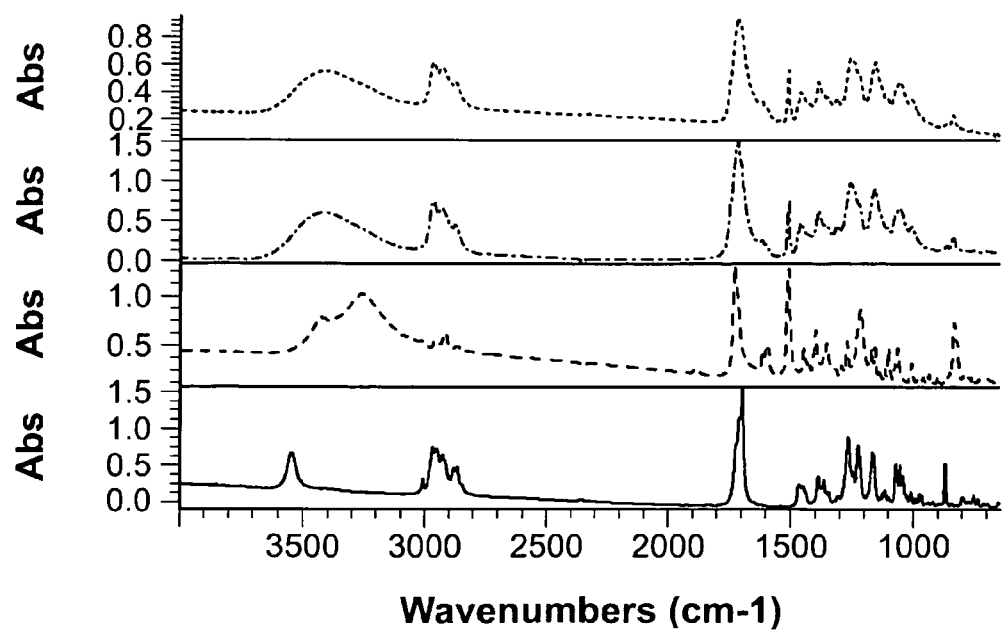
FIG. 44 illustrates a comparison of the FTIR spectrum of a laser treated sample of ezetimibe and simvastatin in a 10:80 ratio by weight with the sequence of laser treatment reversed to the FTIR spectrum of the reference sample.

FIG. 33 illustrates the PXRD pattern of sample laser treated ezetimibe/simvastatin in a 1:1 weight ratio, demonstrating that the combination ezetimibe and simvastatin is co-amorphous. FIG. 34 illustrates the PXRD pattern of laser treated ezetimibe/simvastatin in a 1:2 weight ratio, demonstrating that the combination of ezetimibe and simvastatin co-amorphous. FIG. 35 illustrates the PXRD pattern of laser treated ezetimibe/simvastatin in a 1:4 weight ratio, demonstrating that the combination of ezetimibe and simvastatin is co-amorphous. FIG. 36 illustrates the PXRD pattern of laser treated ezetimibe/simvastatin in a 1:8 ratio by weight, demonstrating that the combination of ezetimibe and simvastatin is co-amorphous.

The co-amorphous combinations of ezetimibe/simvastatin were then analyzed using Fourier transform infrared (FTIR) spectroscopy. FIG. 37, FIG. 38, FIG. 39, and FIG. 40 illustrate the FTIR spectra of the laser treated co-amorphous ezetimibe/simvastatin samples having ratios of 1:1, 1:2, 1:4, and 1:8, respectively. FIG. 41, FIG. 42, FIG. 43, and FIG. 44 illustrate the FTIR spectra of the laser treated co-amorphous ezetimibe/simvastatin samples having ratios of 1:1, 1:2, 1:4, and 1:8, respectively. The progression of compound ratios in each of these sequences is 1:1, 1:2, 1:4, and 1:8. The FTIR spectra of all of these ezetimibe/simvastatin combinations demonstrate that both ezetimibe and simvastatin are present in the co-amorphous samples, and are thoroughly mixed. There is some broadening of a few of the absorbance lines consistent with a non-crystalline form for each of these samples. As the progression of compound ratios becomes more predominant in simvastatin, the spectral bands of simvastatin become relatively stronger than those of the ezetimibe, as would be anticipated for the change in weight ratios in the compositions.

Once the co-amorphous glass combinations were produced through this method, they appeared to be very stable at room temperature storage conditions with no observed tendency to recrystallization. Given the ease of producing the highly non-crystalline co-amorphous form of the different ratios used in this example, it is likely that a wide range of additional ratios could be readily produced. With the observed ease of producing and stabilizing the co-amorphous compositions of ezetimibe and simvastatin, increasing production to the level of large scale manufacturing is expected to be relatively straightforward.

Comparative Example

Ezetimibe/Simvastatin

The protocol of Example 7 was repeated for each of the 1:1, 1:2, 1:4, and 1:8 weight ratio ezetimibe/simvastatin samples with the exception that there was no application of laser radiation. The resulting materials were visibly crystalline, which was confirmed by PXRD analysis, which demonstrated that a substantial amount of crystalline material was present. A PXRD pattern for each of the 1:1, 1:2, 1:4, and 1:8 weight ratio ezetimibe/simvastatin samples obtained without the application of the laser radiation are illustrated in FIGS. 80, 81, 82, and 83, respectively. An FTIR analysis of each of the resulting ezetimibe/simvastatin samples was also performed, confirming that each sample was composed of ezetimibe and simvastatin. The results demonstrate that the co-amorphous ezetimibe/simvastatin is not an artifact of the experiment, but, instead, is a direct result of the application of the laser radiation in the process of the invention.

Example 8

Preparation of Co-Amorphous Glass Ezetimibe/Atorvastatin Calcium

Comparative data for interpretation of results for the co-amorphous combinations was obtained from the PXRD and FTIR analysis of separate untreated reference samples of each of the ezetimibe and atorvastatin calcium and separate samples of ezetimibe and atorvastatin calcium treated with the process of the invention. The PXRD pattern of the reference crystalline ezetimibe is illustrated in FIG. 11. The PXRD pattern of laser treated non-crystalline ezetimibe is shown in FIG. 13. The PXRD pattern of crystalline atorvastatin calcium is illustrated in FIG. 19. The PXRD pattern of laser treated non-crystalline atorvastatin calcium is illustrated in FIG. 20.

The FTIR spectrum of the reference crystalline ezetimibe is illustrated in FIG. 12 with the FTIR spectrum of the non-crystalline laser treated ezetimibe. The FTIR spectrum of the reference crystalline atorvastatin calcium is illustrated in FIG. 21, and the FTIR spectrum of the non-crystalline laser treated atorvastatin calcium is illustrated in FIG. 22.

A 50 mg sample of crystalline ezetimibe and a 50 mg sample of crystalline atorvastatin calcium were dissolved in 2008 mg of absolute ethanol by stirring at 9000 rpm with a magnetic stirrer for 12.5 minutes on a heated plate at 140° C. The solution was then cooled to room temperature, and filtered using a syringe to remove any residual crystals. About 20 percent of the solution was then decanted into a 60 mm×15 mm glass Petri dish on a heated plate at 100° C., and covered with a glass lid to provide approximately 10 mg of ezetimibe and 10 mg of atorvastatin calcium in the treated sample, i.e., a 1:1 weight ratio.

The sample was first treated with amplitude modulated laser radiation from a diode laser having a central wavelength of about 408 nm for 2.5 minutes, and then the sample was treated with amplitude modulated laser radiation from a diode laser having a central wavelength of about 674 nm for 2.5 minutes, rotating the sample slowly through each of the approximately 3 cm diameter expanded beams at a distance of 25 cm from the respective Strachan Devices. The 408 nm laser diode beam had a peak power of 0.88 mW after passing through a Thorlabs 5× beam expander and the Strachan Device. Using the Strachan Device, the 408 nm beam was adjusted to the 80 percent phase cancellation level to achieve a measured power of 0.17 mW over the 3 cm beam. The 674 nm beam was passed through a Thorlabs 5× beam expander and a Strachan Device. The output of the 674 nm beam was optically phase cancelled using the Strachan Device to achieve a measured 80 percent reduction of transmitted power to approximately 0.48 mW over the 3 cm beam. Both beams were electronically amplitude modulated at 6.25 MHz.

Figure 45:
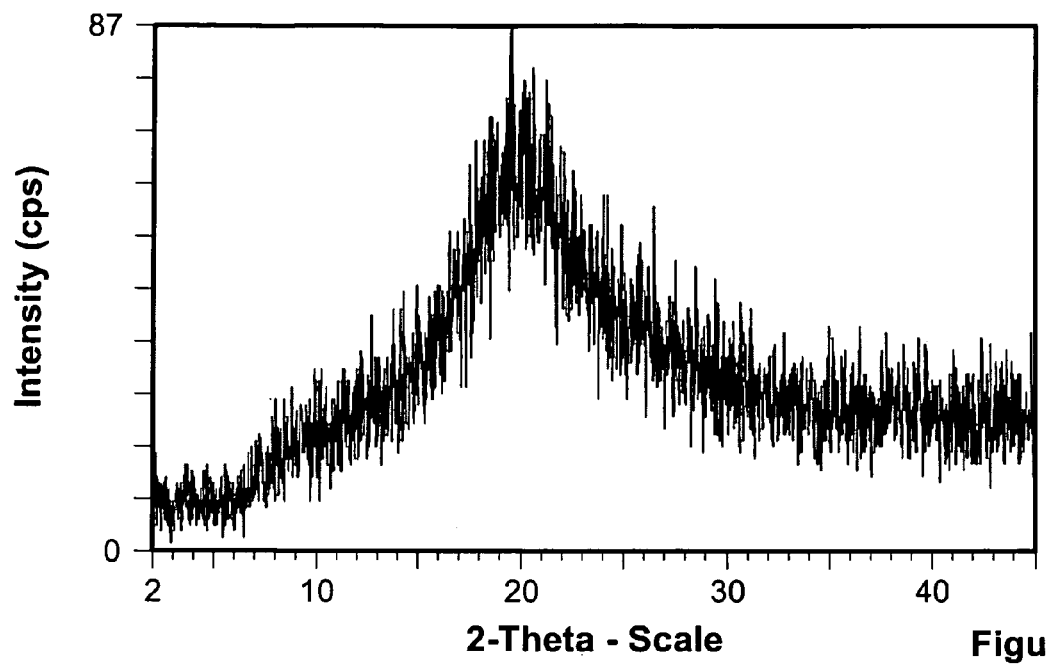
FIG. 45 illustrates the PXRD pattern of a laser treated sample of ezetimibe and atorvastatin calcium in a 1:1 ratio by weight.

After the sequenced laser treatment, the lid of the glass Petri dish was removed, and the solution was allowed to dry through slow evaporation at a temperature of about 22° C. and 24 percent humidity. The resultant ezetimibe/atorvastatin sample dried to a pure transparent glass state. FIG. 45 illustrates the PXRD pattern of the laser treated ezetimibe/atorvastatin calcium in a 1:1 weight ratio, demonstrating that the combination of ezetimibe and atorvastatin calcium is non-crystalline.

Figure 46:
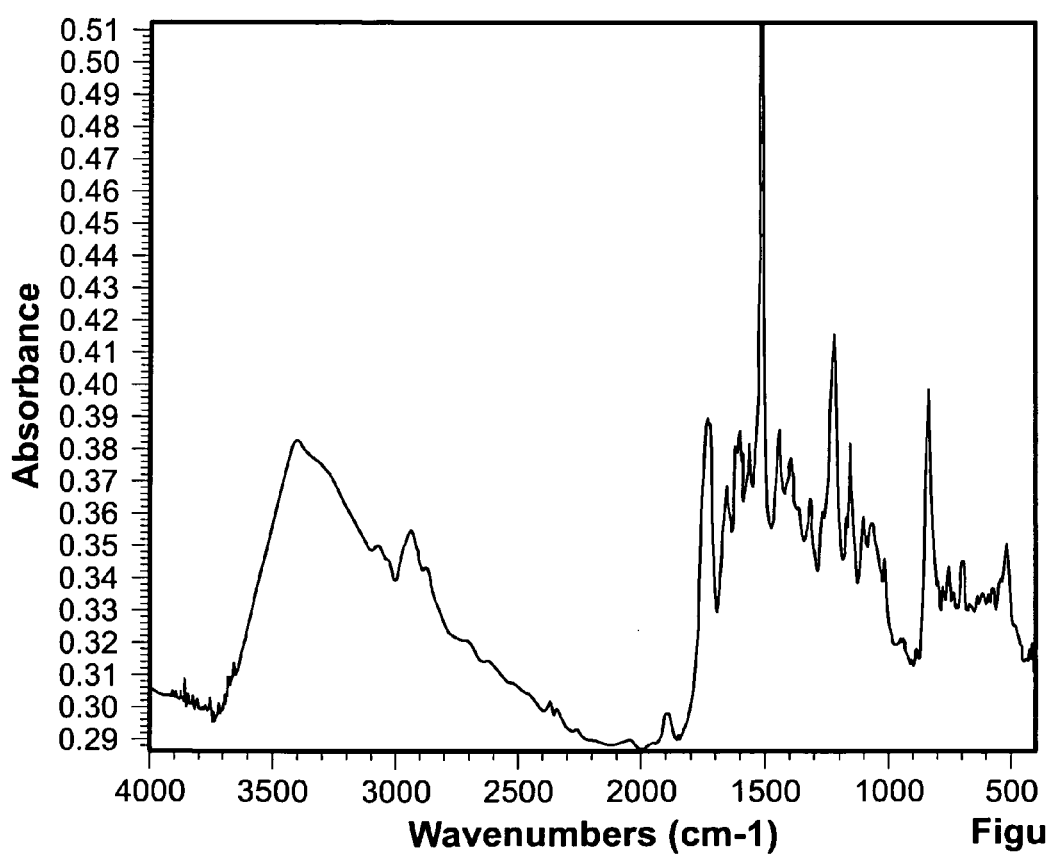
FIG. 46 illustrates the FTIR spectrum of a laser treated sample of ezetimibe and atorvastatin calcium in a 1:1 ratio by weight.

The co-amorphous ezetimibe/atorvastatin calcium composition was then subjected to an FTIR analysis. FIG. 46 illustrates the FTIR spectrum of the laser treated ezetimibe/atorvastatin calcium in a 1:1 ratio, demonstrating that both ezetimibe and atorvastatin calcium are present and thoroughly mixed. There is some broadening of a few of the absorbance lines consistent with the non-crystalline form of each of the compounds.

The co-amorphous combination of ezetimibe/atorvastatin in the 1:1 ratio was found to be very stable at room temperature storage conditions with no observed tendency to recrystallization. Given the ease of producing the highly non-crystalline co-amorphous glass form of this combination of compounds and the non-crystalline glass form of each compound individually, it is likely that a wide range of additional ratios could readily be produced. With the observed ease of producing and stabilizing of the co-amorphous form of this combination of compounds, incrementally increasing production up to the level of large scale manufacturing is expected to be readily accomplished through replication of application modules of this method.

Comparative Example

Ezetimibe/Atorvastatin Calcium

Figure 61:
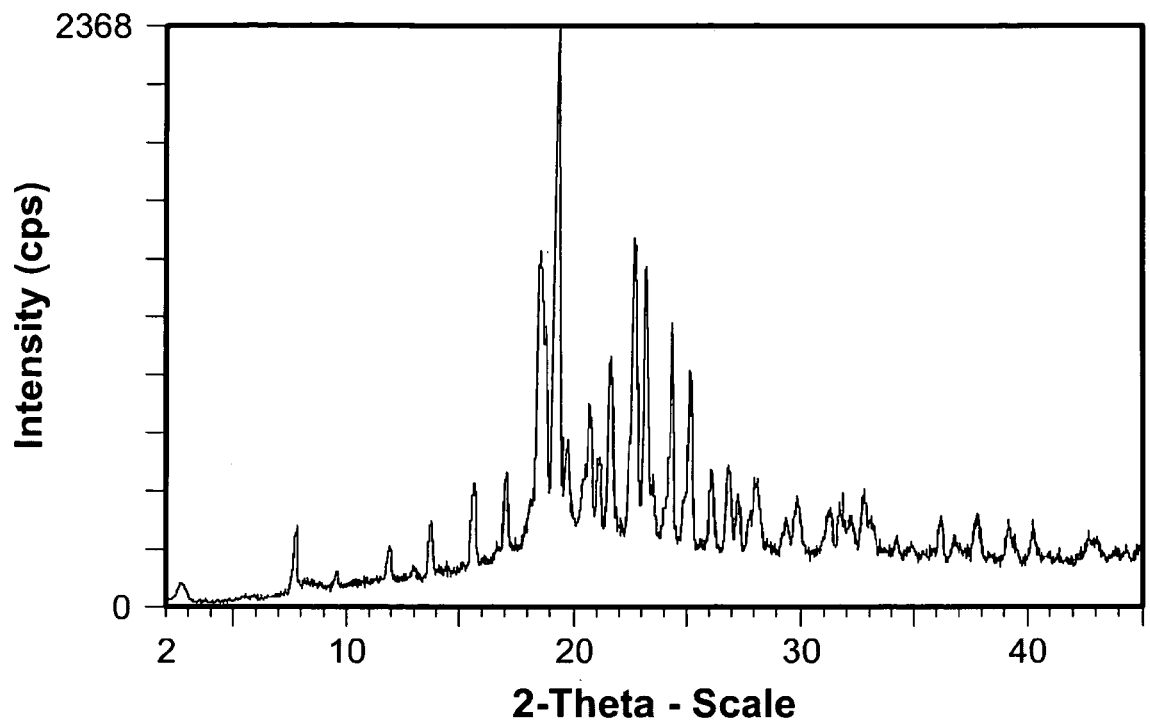
FIG. 61 illustrates the PXRD pattern for a sample of crystalline ezetimibe/atorvastatin calcium formed in the process of the invention, with the exception that laser radiation was not applied.

The protocol of Example 8 was repeated with the exception that there was no application of laser radiation. The resulting material was visibly crystalline, which was confirmed by PXRD analysis, which demonstrated that a substantial amount of crystalline material was present. A PXRD pattern for the ezetimibe/atorvastatin calcium obtained without the application of the laser radiation is illustrated in FIG. 61. The PXRD pattern of FIG. 61 has peaks that correspond to PXRD peaks for ezetimibe and atorvastatin calcium illustrated in FIGS. 11 and 19. An FTIR analysis of the resulting ezetimibe/atorvastatin calcium was also performed, confirming that the material was ezetimibe and atorvastatin calcium. The results demonstrate that the co-amorphous ezetimibe/atorvastatin calcium is not an artifact of the experiment, but, instead, is a direct result of the application of the laser radiation in the process of the invention.

Example 9

Preparation of Co-Amorphous
Ezetimibe/Atorvastatin Free Acid

Comparative data for interpretation of results for the co-amorphous combinations was obtained from the PXRD and FTIR analysis of separate untreated reference samples of each of the ezetimibe and atorvastatin free acid and separate samples of ezetimibe and atorvastatin free acid treated with the process of the invention. The PXRD pattern of the reference crystalline ezetimibe is illustrated in FIG. 11. The PXRD pattern of laser treated non-crystalline ezetimibe is shown in FIG. 13. The PXRD pattern of crystalline atorvastatin free acid is illustrated in FIG. 15. The PXRD pattern of laser treated non-crystalline atorvastatin free acid is shown in FIG. 16.

The spectrum obtained from the FTIR analysis of the reference sample of crystalline ezetimibe is illustrated in FIG. 12 with the FTIR spectrum of the laser treated non-crystalline ezetimibe. The FTIR spectrum of crystalline atorvastatin free acid is illustrated in FIG. 17, and the FTIR spectrum of non-crystalline laser treated atorvastatin free acid is illustrated in FIG. 18.

A 50 mg sample of crystalline ezetimibe and a 50 mg sample of crystalline atorvastatin free acid were dissolved in 1999 mg of absolute ethanol by stirring at 9000 rpm with a magnetic stirrer for 12.5 minutes on a heated plate at 140° C. The solution was then cooled to room temperature, and filtered using a syringe to remove any residual crystals. About 20 percent of the solution was then decanted into a 60 mm×15 mm glass Petri dish on a heated plate at 100° C., and covered with a glass lid to provide a solution of approximately 10 mg of ezetimibe and 10 mg of atorvastatin free acid, i.e., a 1:1 weight ratio of ezetimibe and atorvastatin free acid.

The sample of ezetimibe/atorvastatin free acid was first treated with amplitude modulated laser radiation from a diode laser having a central wavelength of about 674 nm for 2.5 minutes, and then with amplitude modulated laser radiation from a diode laser having a central wavelength of about 408 m for 2.5 minutes, rotating the sample slowly through each of the approximately 3 cm diameter expanded beams at a distance of 25 cm from the respective Strachan Devices. The 674 m laser diode beam was passed through a Thorlabs 5× beam expander and a Strachan Device. Using the Strachan Device, the 674 nm beam was adjusted to the 80 percent phase cancellation level to achieve a power of approximately 0.48 mW over a 3 cm beam. The 408 nm beam had a peak power of 0.88 mW after passing through a Thorlabs 5× beam expander and the Strachan Device. The output of the 408 m beam was optically phase cancelled using the Strachan Device to achieve a measured 80 percent reduction of transmitted power to 0.17 mW over a 3 cm beam. Both beams were electronically amplitude modulated at 6.25 MHz.

Figure 47:
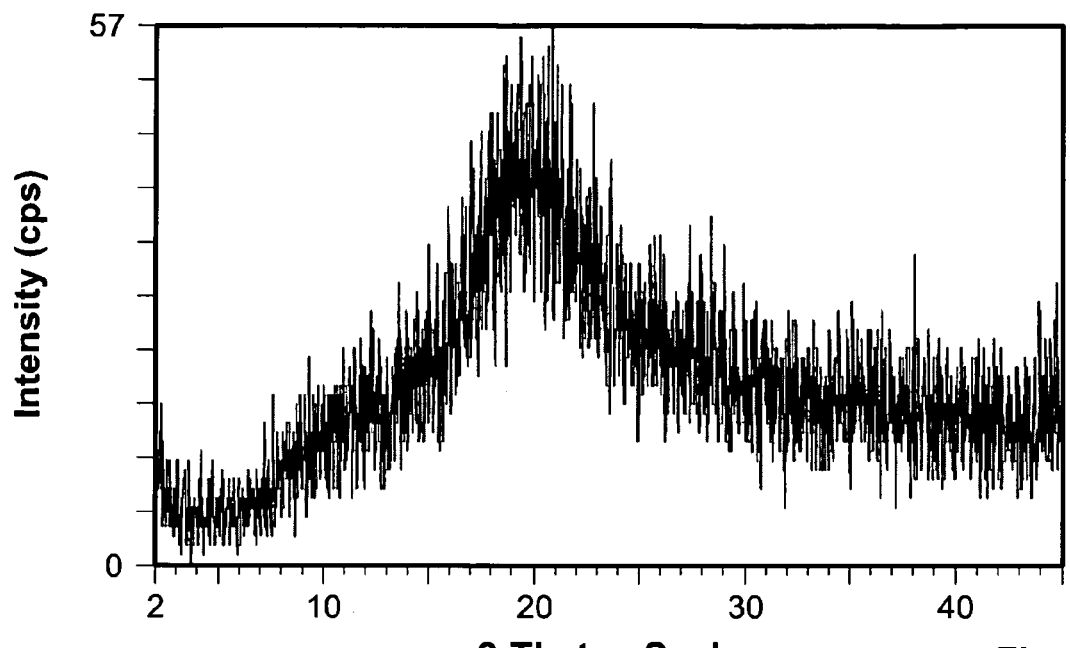
FIG. 47 illustrates the PXRD pattern of a laser treated sample of ezetimibe and atorvastatin free acid in a 1:1 ratio by weight.

After the sequenced laser treatment the lid of the glass Petri dish was removed, and the solution was allowed to dry through slow evaporation at a temperature of about 22° to 23° C. and about 20 percent humidity. The resultant sample of ezetimibe and atorvastatin free acid dried to a pure transparent glass state. FIG. 47 illustrates the PXRD pattern of laser treated ezetimibe/atorvastatin free acid in a 1:1 weight ratio, demonstrating that combination of ezetimibe and atorvastatin free acid is non-crystalline.

Figure 48:
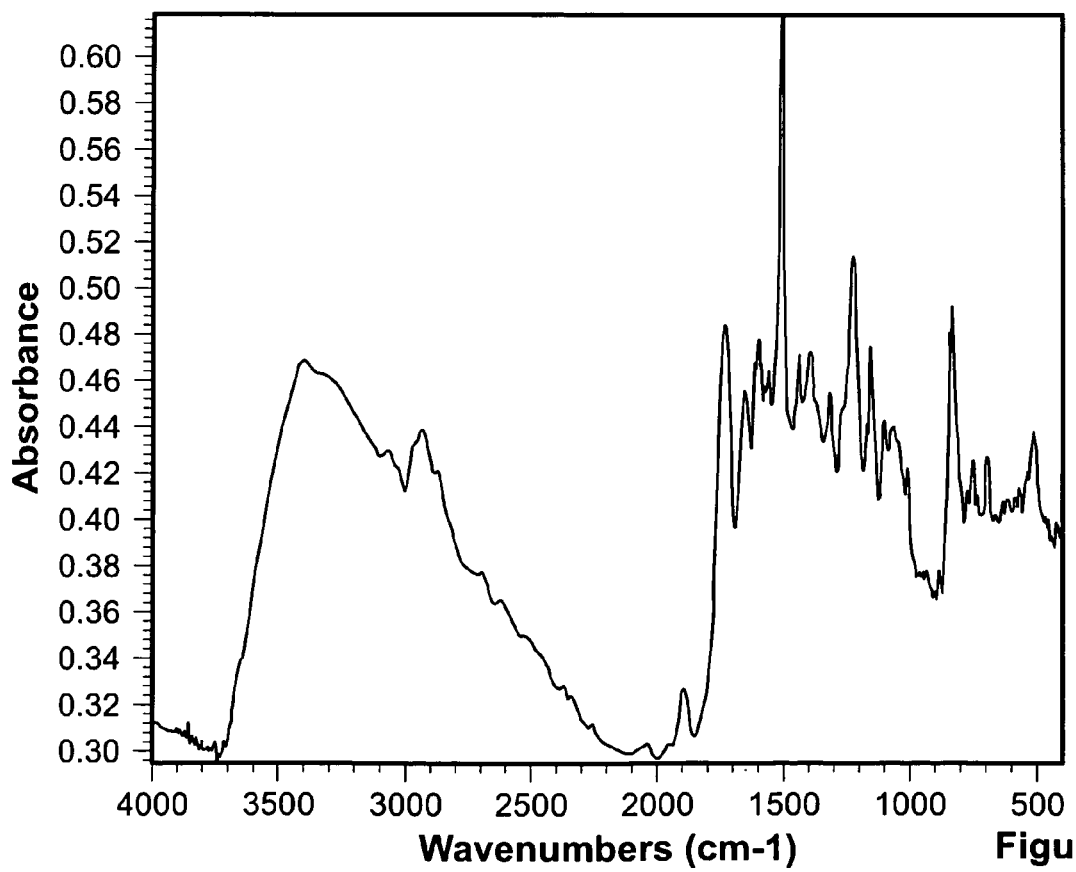
FIG. 48 illustrates the FTIR spectrum of a laser treated sample of ezetimibe and atorvastatin free acid in a 1:1 ratio by weight.

The co-amorphous composition of ezetimibe and atorvastatin free acid was analyzed with FTIR spectroscopy. FIG. 48 illustrates the FTIR spectrum of the laser treated ezetimibe/atorvastatin free acid, indicating that that both compounds are present and are thoroughly mixed in the co-amorphous composition. There is some broadening of a few of the absorbance lines consistent with a non-crystalline form of each compound in the co-amorphous composition.

The co-amorphous ezetimibe/atorvastatin free acid composition, having a 1:1 weight ratio was found to be very stable at room temperature storage conditions with no observed tendency to recrystallize. Given the ease of producing the co-amorphous composition of ezetimibe and atorvastatin free acid, it is likely that a wide range of additional ratios could be produced readily. With the observed ease of producing and stabilizing of the co-amorphous form of this combination of compounds, incrementally increasing production up to the level of large scale manufacturing is expected to be readily accomplished through replication of application modules of this method.

Comparative Example

Ezetimibe/Atorvastatin Free Acid

Figure 62:
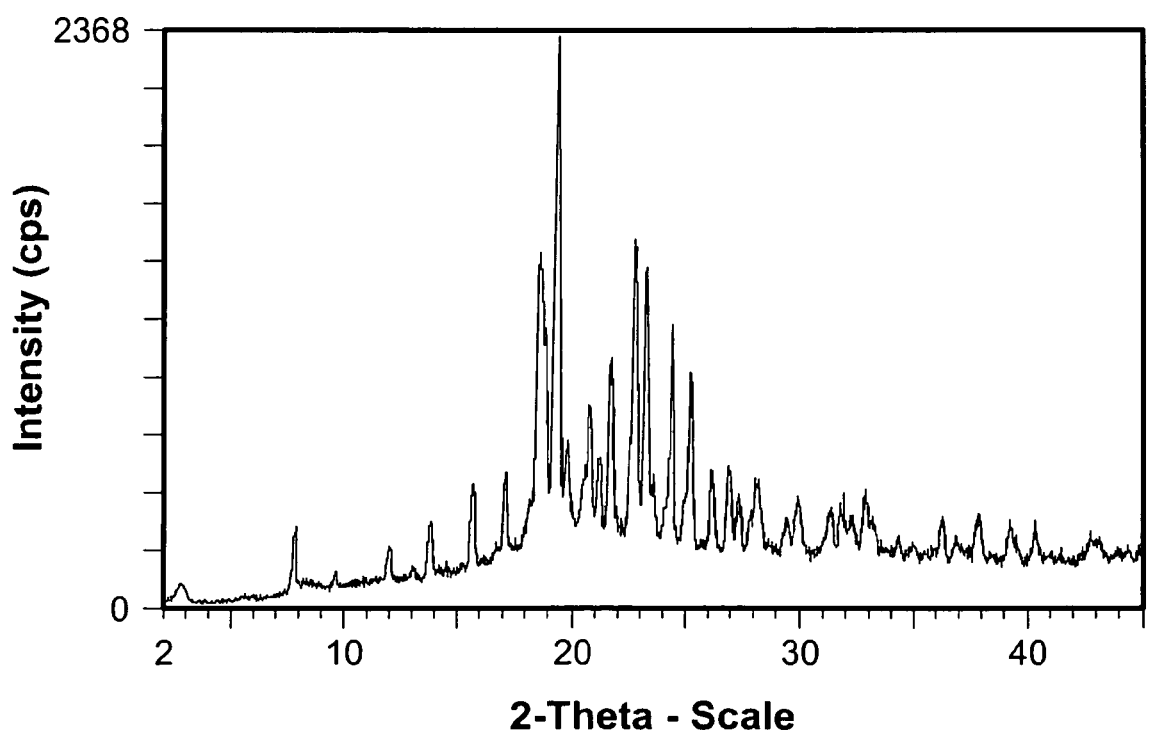
FIG. 62 illustrates the PXRD pattern for a sample of crystalline ezetimibe/atorvastatin free acid formed in the process of the invention, with the exception that laser radiation was not applied.

The protocol of Example 8 was repeated with the exception that there was no application of laser radiation. The resulting material was visibly crystalline, which was confirmed by PXRD analysis, which demonstrated that a substantial amount of crystalline material was present. A PXRD pattern for the ezetimibe/atorvastatin calcium obtained without the application of the laser radiation is illustrated in FIG. 62. The PXRD pattern of FIG. 62 has the peaks that correspond to PXRD peaks for ezetimibe and atorvastatin free acid illustrated in FIGS. 11 and 15. An FTIR analysis of the resulting ezetimibe/atorvastatin free acid was also performed, confirming the material was ezetimibe and atorvastatin free acid. The results demonstrate that the co-amorphous ezetimibe/atorvastatin free acid is not an artifact of the experiment, but, instead, is a direct result of the application of the laser radiation in the process of the invention.

Example 10

Preparation of Co-Amorphous Ezetimibe/Rosuvastatin Calcium

Comparative data for interpretation of results for the co-amorphous combinations was obtained from the PXRD and FTIR analysis of untreated reference samples of each of the ezetimibe and rosuvastatin calcium and samples of ezetimibe and rosuvastatin calcium treated with the process of the invention. The PXRD pattern of the reference crystalline ezetimibe is illustrated in FIG. 11. The PXRD pattern of laser treated non-crystalline ezetimibe is shown in FIG. 13. The PXRD pattern of the reference sample of amorphous rosuvastatin calcium is illustrated in FIG. 25, and the PXRD pattern of the laser treated non-crystalline rosuvastatin calcium is illustrated in FIG. 26.

The FTIR spectrum of the reference crystalline ezetimibe is illustrated in FIG. 12 with the FTIR spectrum of the laser treated non-crystalline ezetimibe. The FTIR spectrum of the reference sample of rosuvastatin calcium is illustrated in FIG. 27, and the FTIR spectrum of the non-crystalline laser treated rosuvastatin calcium is illustrated FIG. 28.

A 10 mg sample of crystalline ezetimibe and a 10 mg sample of rosuvastatin calcium were dissolved in 408 mg of absolute ethanol by stirring at 9000 rpm with a magnetic stirrer for 8 minutes, followed by stirring at 9000 rpm with a magnetic stirrer for an additional 10 minutes on a heated plate at 140° C. The solution was decanted into a 60 mm×15 mm glass Petri dish on a heated plate at 100° C., and covered with a glass lid to provide approximately 10 mg of ezetimibe and 10 mg of atorvastatin free acid in the solution, i.e., a 1:1 weight ratio.

The ezetimibe/rosuvastatin sample was treated first with amplitude modulated laser radiation from a diode laser having a central wavelength of about 674 nm wavelength for 2.5 minutes, then with amplitude modulated laser radiation from a diode laser having a central wavelength of about 408 nm for 2.5 minutes, rotating the sample slowly through each of the approximately 3 cm diameter expanded beams at a distance of 25 cm from the respective Strachan Devices. The 674 nm laser diode beam was passed through a Thorlabs 5× beam expander and a Strachan Device. Using the Strachan Device, the 674 μm beam was adjusted to the 80 percent phase cancellation level to achieve a power of approximately 0.048 mW over a 3 cm diameter beam. The 408 nm beam had a peak power of 2.15 mW after passing through a Thorlabs 5× beam expander and the Strachan Device. The output of the 408 nm beam was optically phase cancelled using the Strachan Device to achieve a measured 80 percent reduction of transmitted power to 0.43 mW over a 3 cm diameter beam. Both beams were electronically amplitude modulated at 6.25 MHz.

Figure 49:
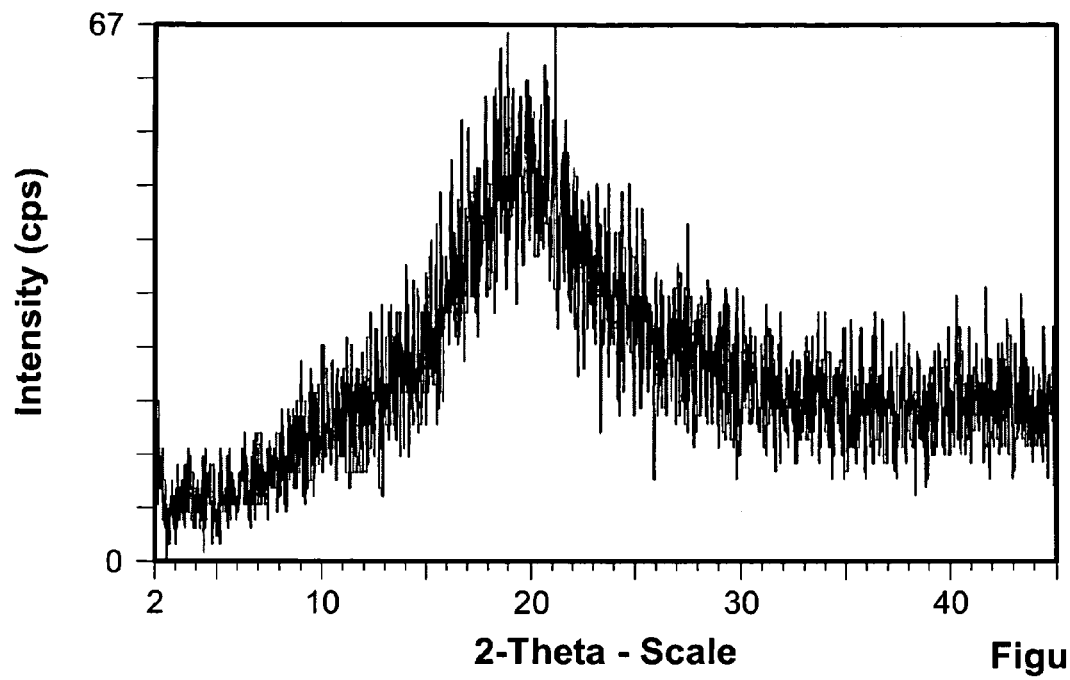
FIG. 49 illustrates the PXRD pattern of a laser treated sample of ezetimibe and rosuvastatin calcium in a 1:1 ratio by weight.

After the sequenced laser treatment of the ezetimibe and rosuvastatin calcium, the lid of the glass Petri dish was removed, and the solution was allowed to dry through slow evaporation at a temperature of 19° C. and 45 percent humidity. The resultant material for the sample of ezetimibe/rosuvastatin dried to a pure transparent glass state. FIG. 49 illustrates the PXRD pattern of the laser treated ezetimibe/rosuvastatin in a 1:1 weight ratio, demonstrating that the combination of ezetimibe and rosuvastatin calcium is non-crystalline.

Figure 50:
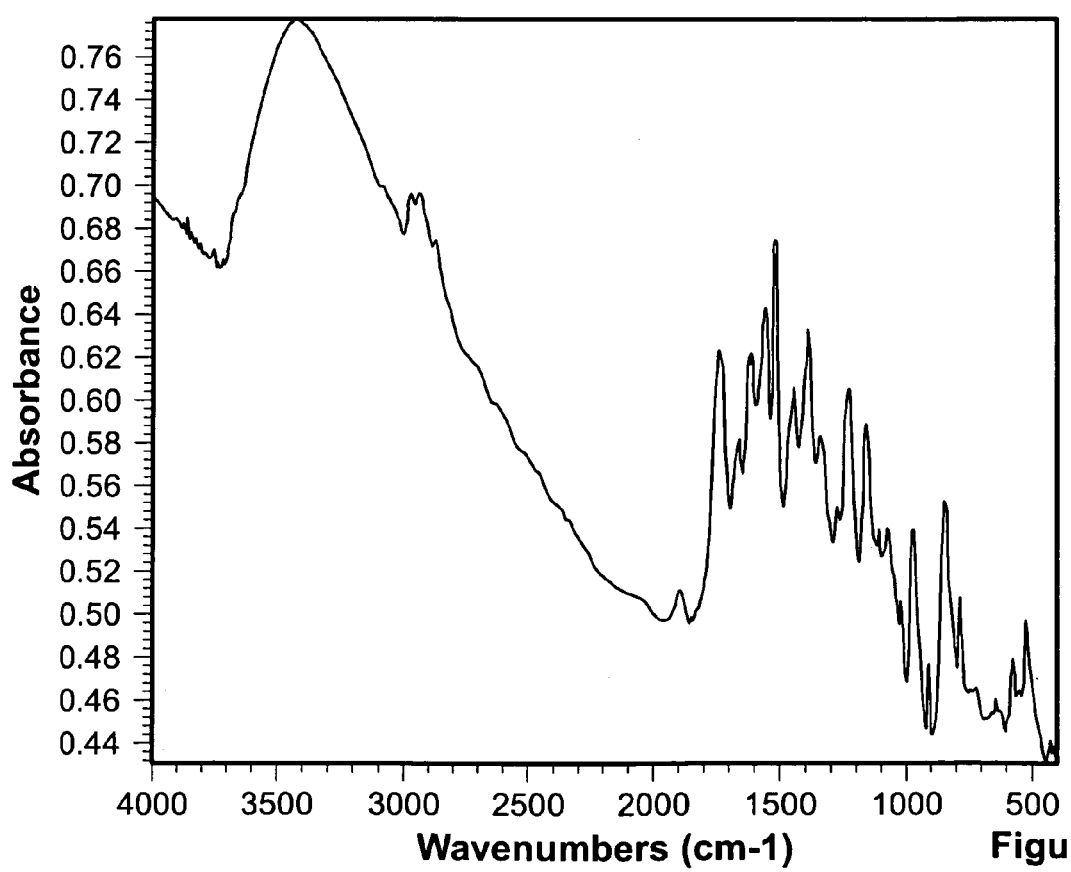
FIG. 50 illustrates the FTIR spectrum of a laser treated sample of ezetimibe and rosuvastatin calcium in a 1:1 ratio by weight.

The co-amorphous composition of ezetimibe and rosuvastatin calcium was then analyzed with FTIR spectroscopy. FIG. 50 illustrates the FTIR spectrum of the laser treated ezetimibe/rosuvastatin, demonstrating that both ezetimibe and rosuvastatin calcium compounds are present in the composition and thoroughly mixed. There is also some broadening of a few of the absorbance lines consistent with a non-crystalline form for each of the compounds.

The ezetimibe/rosuvastatin calcium composition in a 1:1 weight ratio was found to be very stable at room temperature storage conditions with no observed tendency to recrystallize. Given the ease of producing the co-amorphous form of the ezetimibe/rosuvastatin calcium composition and the non-crystalline glass form of each compound individually, it is likely that a wide range of additional ratios could readily be produced. With the observed ease of producing and stabilizing of the co-amorphous ezetimibe and rosuvastatin calcium, scaling production up to the level of large scale manufacturing is expected to be readily accomplished through replication of application modules of this method.

Comparative Example

Ezetimibe/Rosuvastatin Calcium

Figure 63:
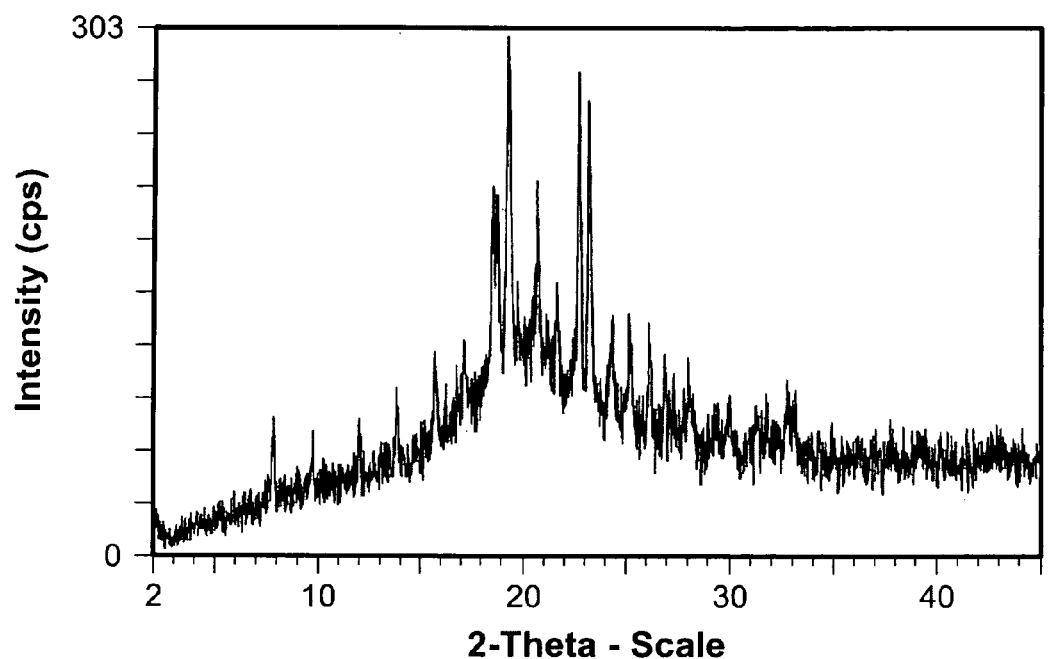
FIG. 63 illustrates the PXRD pattern for a sample of crystalline ezetimibe/rosuvastatin calcium formed in the process of the invention, with the exception that laser radiation was not applied.

The protocol of Example 10 was repeated with the exception that there was no application of laser radiation. The resulting material was visibly crystalline, which was confirmed by PXRD analysis, which demonstrated that a substantial amount of crystalline material was present. A PXRD pattern for the ezetimibe/rosuvastatin calcium obtained without the application of the laser radiation is illustrated in FIG. 63. The PXRD pattern of FIG. 63 has the peaks that correspond to PXRD peaks for ezetimibe and rosuvastatin calcium illustrated in FIGS. 11 and 25. An FTIR analysis of the resulting ezetimibe/rosuvastatin calcium was also performed, confirming the material was ezetimibe and rosuvastatin calcium. The results demonstrate that the co-amorphous ezetimibe/rosuvastatin calcium is not an artifact of the experiment, but, instead, is a direct result of the application of the laser radiation in the process of the invention.

Example 11

Preparation of Co-Amorphous Ezetimibe/Simvastatin/Aspirin

Comparative data for interpretation of results for the co-amorphous combinations was obtained from the PXRD and FTIR analysis of untreated reference samples of each of the ezetimibe, simvastatin, and aspirin and samples of ezetimibe, simvastatin, and aspirin treated with the process of the invention. The PXRD pattern of the reference crystalline ezetimibe is illustrated in FIG. 11. The PXRD pattern of laser treated non-crystalline ezetimibe is shown in FIG. 13. The PXRD pattern of crystalline simvastatin is illustrated in FIG. 7. The PXRD pattern of laser treated non-crystalline simvastatin is illustrated in FIG. 9. The PXRD pattern of crystalline aspirin is illustrated in FIG. 1. The PXRD pattern of laser treated non-crystalline aspirin is illustrated in FIG. 3.

The FTIR spectrum of crystalline ezetimibe is illustrated in FIG. 12 with the FTIR spectrum of non-crystalline laser treated ezetimibe. The FTIR spectrum of the reference sample of crystalline simvastatin is illustrated in FIG. 8. The FTIR spectrum of the laser treated non-crystalline simvastatin is illustrated in FIG. 10. The FTIR spectrum of crystalline aspirin is illustrated in FIG. 2. The FTIR spectrum of non-crystalline laser treated aspirin is illustrated in FIG. 4.

A 10 mg sample of crystalline ezetimibe, a 10 mg sample of crystalline simvastatin, and a 5 mg sample of crystalline aspirin were dissolved in 1000 mg of absolute ethanol by stirring at 9000 rpm with a magnetic stirrer for 12 minutes on a heated plate at 140° C. The solution was then cooled to room temperature, and filtered using a syringe to remove any residual crystals. The solution was then decanted into a 60 mm×15 mm glass Petri dish, and covered with a glass lid to provide 10 mg of ezetimibe, 10 mg of simvastatin, and 5 mg of aspirin in the sample of ezetimibe/simvastatin/aspirin; i.e., a 2:2:1 weight ratio.

The sample of ezetimibe/simvastatin/aspirin was first treated with amplitude modulated laser radiation from a diode laser having a central wavelength of about 408 nm for 2.5 minutes, and then with amplitude modulated laser radiation from a diode laser having a central wavelength of about 674 nm for 2.5 minutes, rotating the sample slowly through each of the approximately 3 cm diameter expanded beams at a distance of 25 cm from the respective Strachan Devices. The 408 nm laser diode beam had a peak power of 2.61 mW after passing through a Thorlabs 5× beam expander and the Strachan Device. Using the Strachan Device, the 408 nm beam was adjusted to the 80 percent phase cancellation level to achieve a power of approximately 0.52 mW over a 3 cm diameter beam. The 674 nm beam was passed through a Thorlabs 5× beam expander and a Strachan Device. The output of the 674 nm beam was optically phase cancelled using the Strachan Device to achieve a measured 80 percent reduction of transmitted power to approximately 0.48 mW over a 3 cm diameter beam. Both beams were electronically amplitude modulated at 6.25 MHz.

Figure 51:
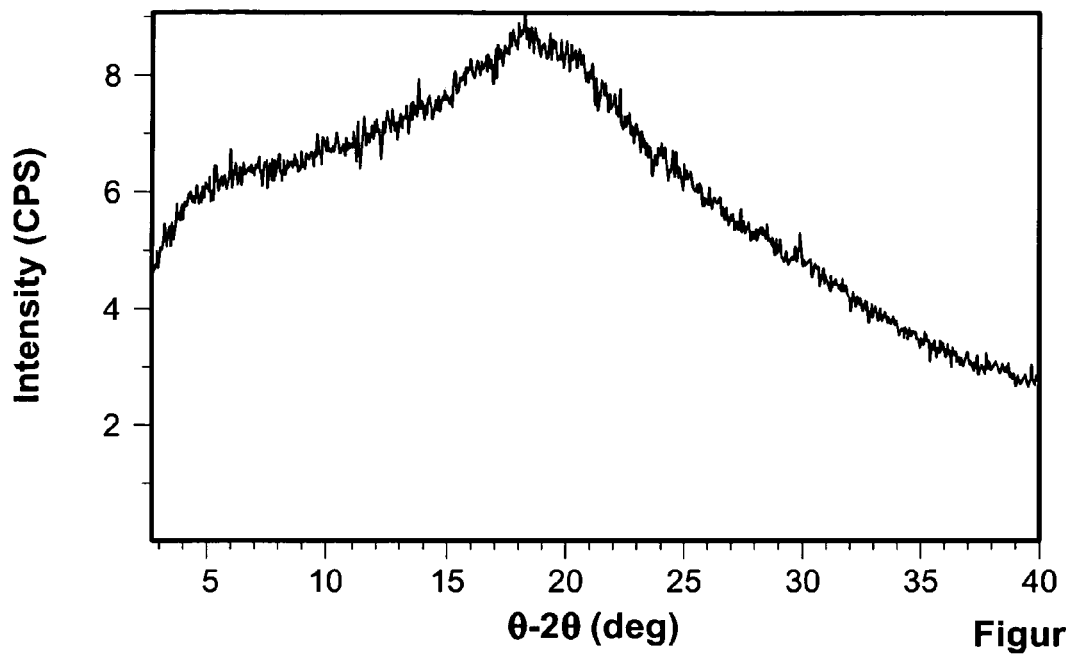
FIG. 51 illustrates the PXRD pattern of a laser treated sample of ezetimibe, simvastatin, and aspirin in a 2:2:1 ratio by weight.

After the sequenced laser treatment, the lid of the glass Petri dish was removed, and the solution was allowed to dry through slow evaporation at a temperature of 21° C. and 26 percent humidity. The resultant material for the ezetimibe/simvastatin/aspirin sample dried to a pure transparent glass state. FIG. 51 illustrates the PXRD pattern of the laser treated ezetimibe/simvastatin/aspirin in a 2:2:1 weight ratio, demonstrating the composition of ezetimibe, simvastatin, and aspirin is non-crystalline.

Figure 52:
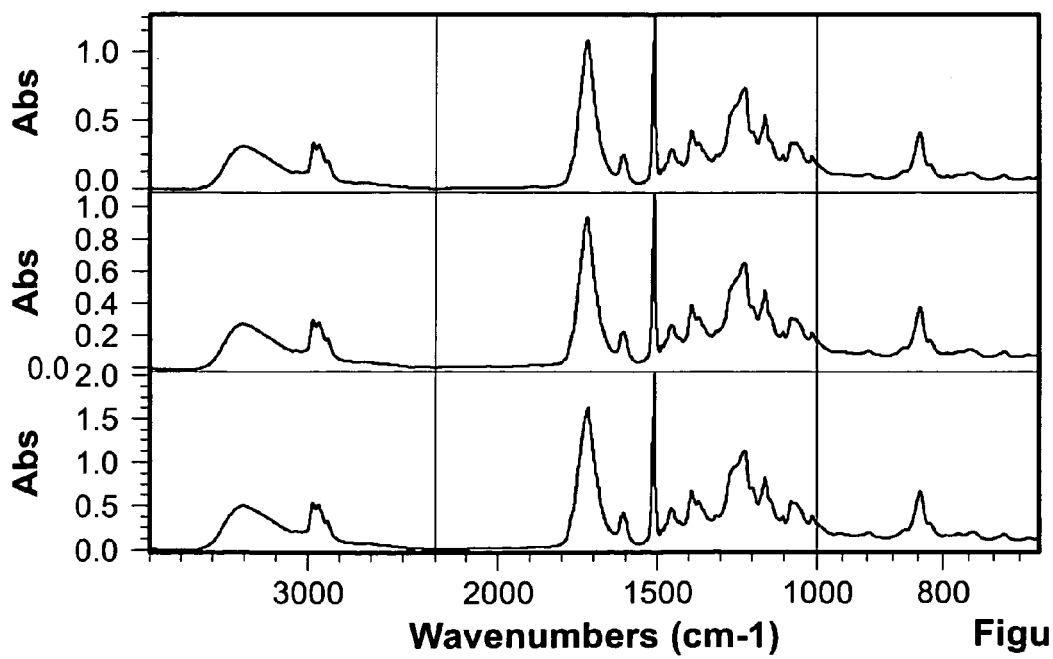
FIG. 52 illustrates FTIR spectra of a laser treated sample of ezetimibe, simvastatin, and aspirin in a 2:2:1 ratio by weight.

The co-amorphous composition of ezetimibe, simvastatin, and aspirin was then analyzed using FTIR spectroscopy. FIG. 52 illustrates the FTIR spectrum of the co-amorphous laser treated ezetimibe/simvastatin/aspirin composition, demonstrating that indicate that all three compounds are present and thoroughly mixed. There is also some broadening of a few of the absorbance lines consistent with a non-crystalline form.

The co-amorphous glass composition of ezetimibe/simvastatin/aspirin in a 2:2:1 weight ratio was found to be very stable at room temperature storage conditions with no observed tendency to recrystallize. With the observed ease of producing and stabilizing of the co-amorphous form of this combination of compounds, scale up of manufacturing is expected to be readily accomplished.

Comparative Example

Ezetimibe/Simvastatin/Aspirin

Figure 68:
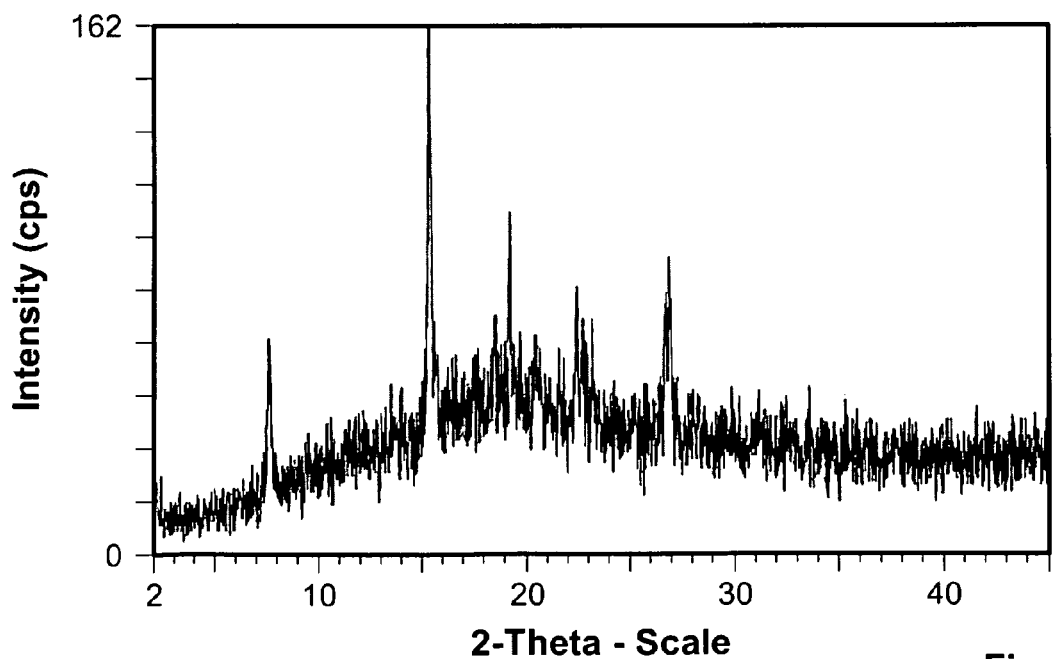
FIG. 68 illustrates the PXRD pattern for a sample of crystalline ezetimibe/simvastatin/aspirin formed in the process of the invention, with the exception that laser radiation was not applied.

The protocol of Example 11 was repeated with the exception that there was no application of laser radiation. The resulting material was visibly crystalline, which was confirmed by PXRD analysis, which demonstrated that a substantial amount of crystalline material was present. A PXRD pattern for the ezetimibe/simvastatin/aspirin obtained without the application of the laser radiation is illustrated in FIG. 68. The PXRD pattern of FIG. 68 has the peaks that correspond to PXRD peaks for ezetimibe, simvastatin, and aspirin illustrated in FIGS. 11, 8, and 1. An FTIR analysis of the resulting ezetimibe/simvastatin/aspirin was also performed, confirming that the crystalline material was ezetimibe, simvastatin, and aspirin. The results demonstrate that the co-amorphous ezetimibe/simvastatin/aspirin is not an artifact of the experiment, but, instead, is a direct result of the application of the laser radiation in the process of the invention.

Example 12

Preparation of Co-Amorphous Ezetimibe/Atorvastatin Calcium/Aspirin

Comparative data for interpretation of results for the co-amorphous combinations was obtained from the PXRD and FTIR analysis of untreated reference samples of each of the ezetimibe and atorvastatin calcium and aspirin and the non-crystalline forms of these compounds treated with the process of the invention. The PXRD pattern of the reference crystalline ezetimibe is illustrated in FIG. 11. The PXRD pattern of laser treated non-crystalline ezetimibe is shown in FIG. 13. The PXRD pattern of crystalline atorvastatin calcium is illustrated in FIG. 19. The PXRD pattern of laser treated non-crystalline atorvastatin calcium is illustrated in FIG. 20. The PXRD pattern of crystalline aspirin is illustrated in FIG. 1. The PXRD pattern of laser treated non-crystalline aspirin is illustrated in FIG. 3.

The FTIR spectrum of the reference crystalline ezetimibe is illustrated in FIG. 12 with the FTIR spectrum of non-crystalline laser treated ezetimibe. The FTIR spectrum of the reference sample of crystalline atorvastatin calcium is illustrated in FIG. 21. The FTIR spectrum of non-crystalline laser treated atorvastatin calcium is illustrated in FIG. 22. The FTIR spectrum of the reference sample of crystalline aspirin is illustrated in FIG. 2. The FTIR spectrum of non-crystalline laser treated aspirin is illustrated in FIG. 4.

A 50 mg sample of crystalline ezetimibe, a 50 mg sample of crystalline atorvastatin calcium, and a 25 mg sample of crystalline aspirin were dissolved in 2400 mg of absolute ethanol by stirring at 9000 rpm with a magnetic stirrer for 12 minutes on a heated plate at 140° C. The solution was then cooled to room temperature, and filtered using a syringe to remove any residual crystals. Then, 20 percent of the solution was decanted into a 60 mm×15 mm glass Petri dish, and covered with a glass lid to provide 10 mg of ezetimibe, 10 mg of atorvastatin calcium, and 5 mg of aspirin in this sample of ezetimibe/atorvastatin calcium/aspirin, i.e., a 2:2:1 weight ratio.

The ezetimibe, atorvastatin calcium, and aspirin were first treated with amplitude modulated laser radiation from a diode laser emitting at a central wavelength of about 408 nm for 2.5 minutes, and then with amplitude modulated laser radiation from a diode laser emitting at a central wavelength of about 674 nm wavelength for 2.5 minutes, rotating the sample slowly through each of the approximately 3 cm diameter expanded beams at a distance of 25 cm from the Strachan Device. The 408 nm laser diode beam had a peak power of 0.71 mW after passing through a Thorlabs 5× beam expander and the Strachan Device. Using the Strachan Device, the 408 nm beam was adjusted to the 80 percent phase cancellation level to achieve a measured power of 0.14 mW. The 674 nm beam was passed through a Thorlabs 5× beam expander and the Strachan Device. The output of the 674 nm beam was optically phase cancelled using the Strachan Device to achieve a measured 80 percent reduction of transmitted power to 0.48 mW over a 3 cm diameter beam. Both beams were electronically amplitude modulated at 6.25 MHz.

Figure 53:
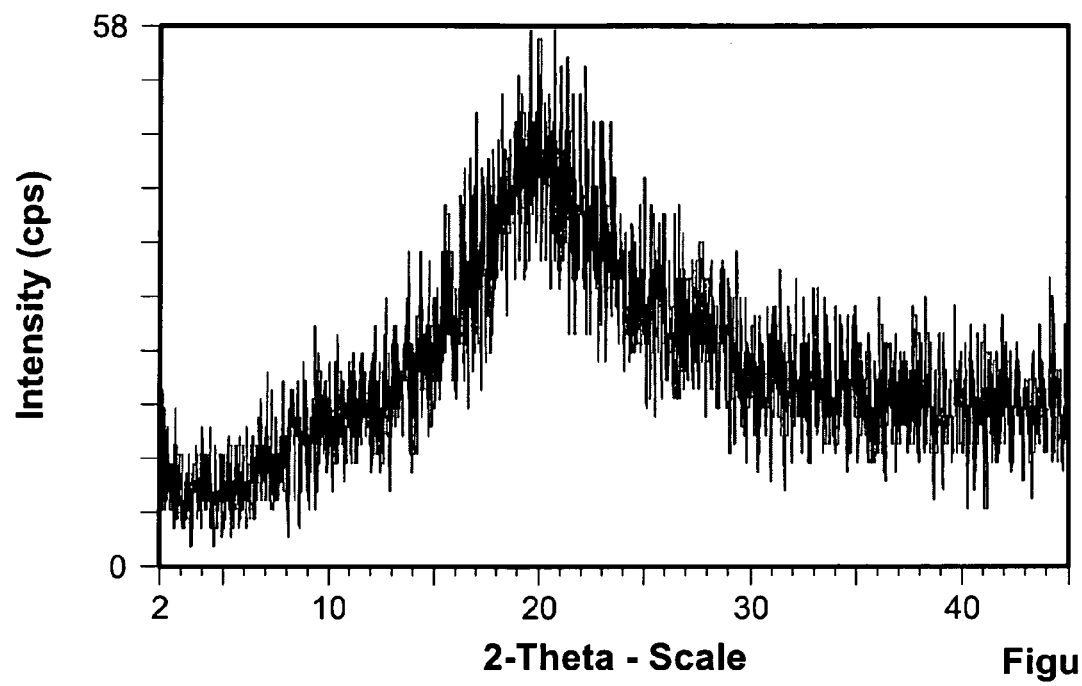
FIG. 53 illustrates the PXRD pattern of a laser treated sample of ezetimibe, atorvastatin calcium, and aspirin in a 2:2:1 ratio by weight.

After the sequenced laser treatment, the lid of the glass Petri dish was removed, and the solution was allowed to dry through slow evaporation at a room temperature of about 20° to 21° C. and 34 percent humidity. The resultant ezetimibe/atorvastatin calcium/aspirin composition dried to a pure transparent glass state. FIG. 53 illustrates the PXRD pattern of the laser treated ezetimibe/atorvastatin calcium/aspirin in a 2:2:1 weight ratio to demonstrate that the combination of ezetimibe, atorvastatin calcium, and aspirin was non-crystalline.

Figure 54:
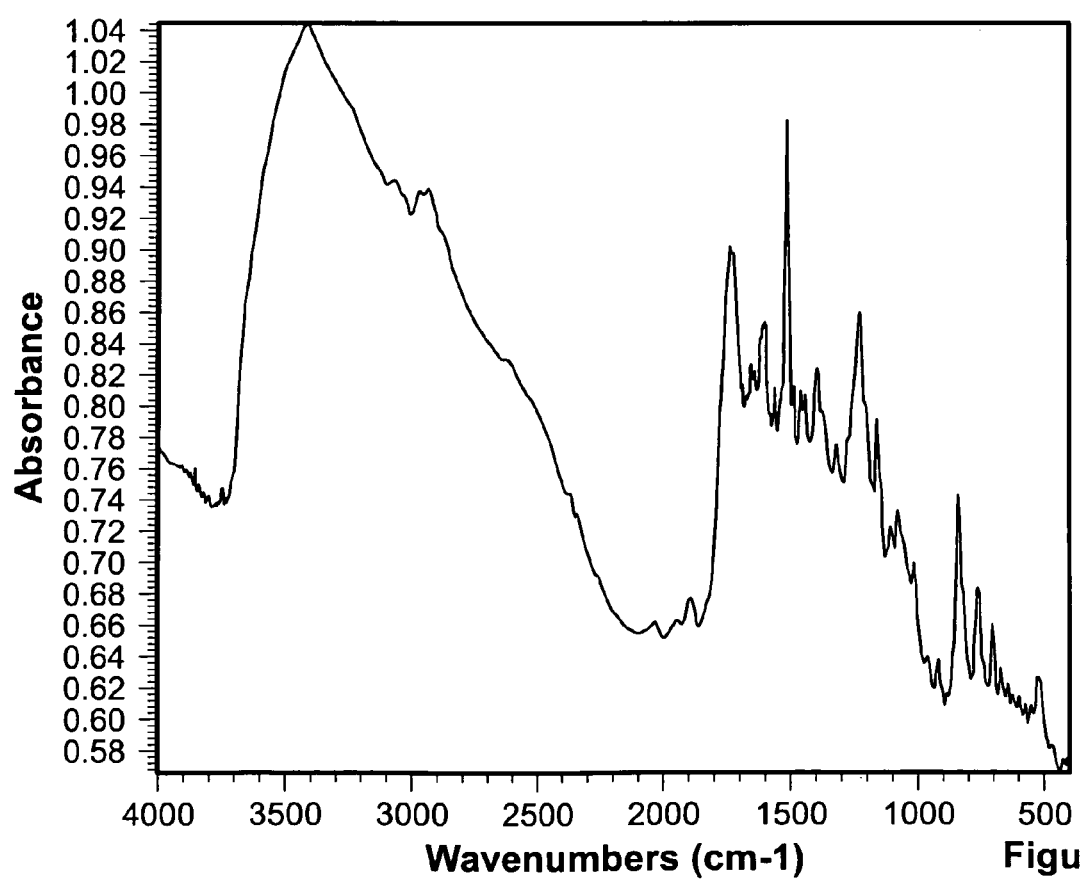
FIG. 54 illustrates the FTIR spectrum of a laser treated sample of ezetimibe, atorvastatin calcium, and aspirin in a 2:2:1 ratio by weight.

The co-amorphous ezetimibe/atorvastatin calcium/aspirin composition was then analyzed using FTIR spectroscopy. FIG. 54 illustrates the FTIR spectroscopic pattern of the laser treated ezetimibe/atorvastatin calcium/aspirin, demonstrating that all three compounds are present and are thoroughly mixed. There is also some broadening of a few of the absorbance lines consistent with a non-crystalline form.

The 2:2:1 weight ratio ezetimibe/simvastatin/aspirin composition found to be very stable at room temperature storage conditions with no observed tendency to recrystallization. With the observed ease of producing and stabilizing of the co-amorphous form of this combination of compounds, increasing production up to the level of large scale manufacturing is expected to be readily accomplished through replication of application modules of this method.

Comparative Example

Ezetimibe/Atorvastatin Calcium/Aspirin

Figure 64:
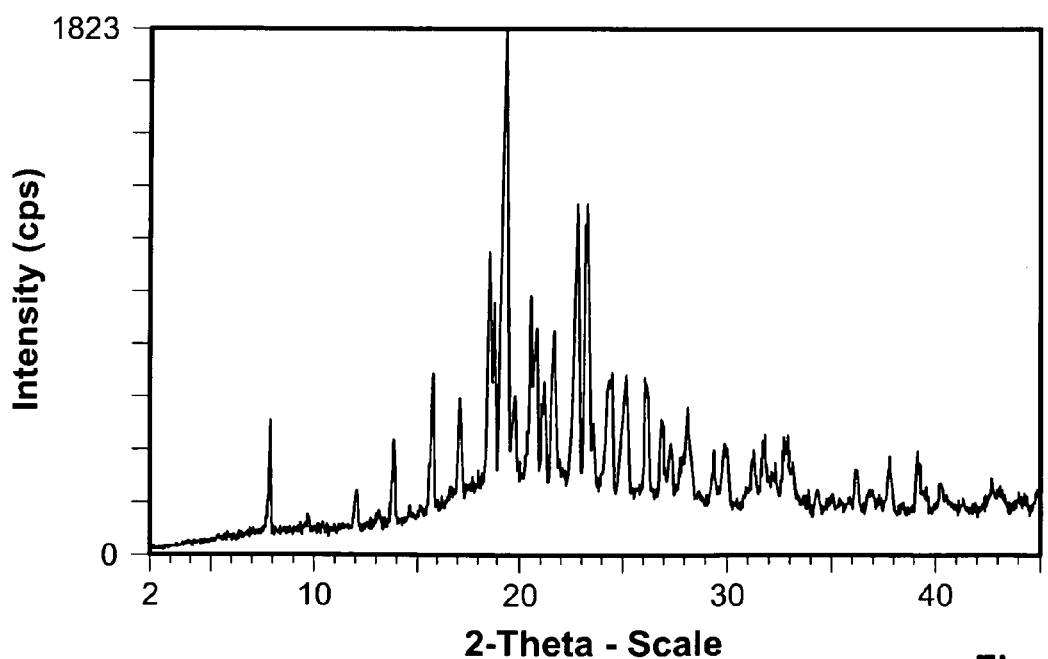
FIG. 64 illustrates the PXRD pattern for a sample of crystalline ezetimibe/atorvastatin calcium/aspirin formed in the process of the invention, with the exception that laser radiation was not applied.

The protocol of Example 12 was repeated with the exception that there was no application of laser radiation. The resulting material was visibly crystalline, which was confirmed by PXRD analysis, which demonstrated that a substantial amount of crystalline material was present. A PXRD pattern for the ezetimibe/atorvastatin calcium/aspirin obtained without the application of the laser radiation is illustrated in FIG. 62. The PXRD pattern of FIG. 64 has the peaks that correspond to PXRD peaks for ezetimibe, atorvastatin calcium, and aspirin illustrated in FIGS. 11, 19, and 1. An FTIR analysis of the resulting ezetimibe/atorvastatin calcium/aspirin was also performed, confirming the material was ezetimibe, atorvastatin calcium, and aspirin. The results demonstrate that the co-amorphous ezetimibe/atorvastatin calcium/aspirin is not an artifact of the experiment, but, instead, is a direct result of the application of the laser radiation in the process of the invention.

Example 13

Preparation of Co-Amorphous
Ezetimibe/Atorvastatin Free Acid/Aspirin

Comparative data for interpretation of results for the co-amorphous combinations was obtained from the PXRD and FTIR analysis of untreated reference samples of each of the ezetimibe and atorvastatin free acid and aspirin and the non-crystalline form of these compounds treated with the process of the invention. The PXRD pattern of the reference crystalline ezetimibe is illustrated in FIG. 11. The PXRD pattern of laser treated non-crystalline ezetimibe is shown in FIG. 13. The PXRD pattern of crystalline atorvastatin free acid is illustrated in FIG. 15. The PXRD pattern of the non-crystalline laser treated atorvastatin free acid is illustrated in FIG. 16. The PXRD pattern of the crystalline aspirin is illustrated in FIG. 1. The PXRD pattern of laser treated non-crystalline aspirin is illustrated in FIG. 3.

The FTIR spectrum of the reference sample of crystalline ezetimibe is illustrated in FIG. 12 with the FTIR spectrum of non-crystalline laser treated ezetimibe. The FTIR spectrum of the reference sample of crystalline atorvastatin free acid is illustrated in FIG. 17. The FTIR spectrum of non-crystalline laser treated atorvastatin free acid is illustrated in FIG. 18. The FTIR spectrum of the reference sample of crystalline aspirin is illustrated in FIG. 2. The FTIR spectrum of non-crystalline laser treated aspirin is illustrated in FIG. 4.

A 50 mg sample of crystalline ezetimibe, a 50 mg sample of crystalline atorvastatin free acid, and a 25 mg sample of crystalline aspirin were dissolved in 2400 mg of absolute ethanol by stirring at 9000 rpm with a magnetic stirrer for 12 minutes at on a heated plate at 140° C. The solution was then cooled to room temperature, and filtered using a syringe to remove any residual crystals. 20 percent of this solution was then decanted into a 60 mm×15 mm glass Petri dish and covered with a glass lid to provide 10 mg of ezetimibe, 10 mg of atorvastatin free acid, and 5 mg of aspirin in this sample of ezetimibe/atorvastatin free acid/aspirin, i.e., a 2:2:1 weight ratio.

The ezetimibe, atorvastatin free acid, and aspirin were first treated with amplitude modulated laser radiation emitted from a diode laser having a central wavelength of about 408 for 2.5 minutes, and then with amplitude modulated laser radiation emitted from a diode laser having a central wavelength of about 674 nm for 2.5 minutes, rotating the sample slowly through each of the approximately 3 cm diameter expanded beams at a distance of 25 cm from the Strachan Device. The 408 nm laser diode beam had a peak power of 0.71 mW after passing through a Thorlabs 5× beam expander and the Strachan Device. Using the Strachan Device, the 408 nm beam was adjusted to the 80 percent phase cancellation level to achieve a measured power of 0.14 mW. The 674 nm beam was passed through a Thorlabs 5× beam expander and the Strachan Device. The output of the 674 nm beam was optically phase cancelled using the Strachan Device to achieve a measured 80 percent reduction of transmitted power to 0.48 mW over a 3 cm diameter beam. Both beams were electronically amplitude modulated at 6.25 MHz.

Figure 55:
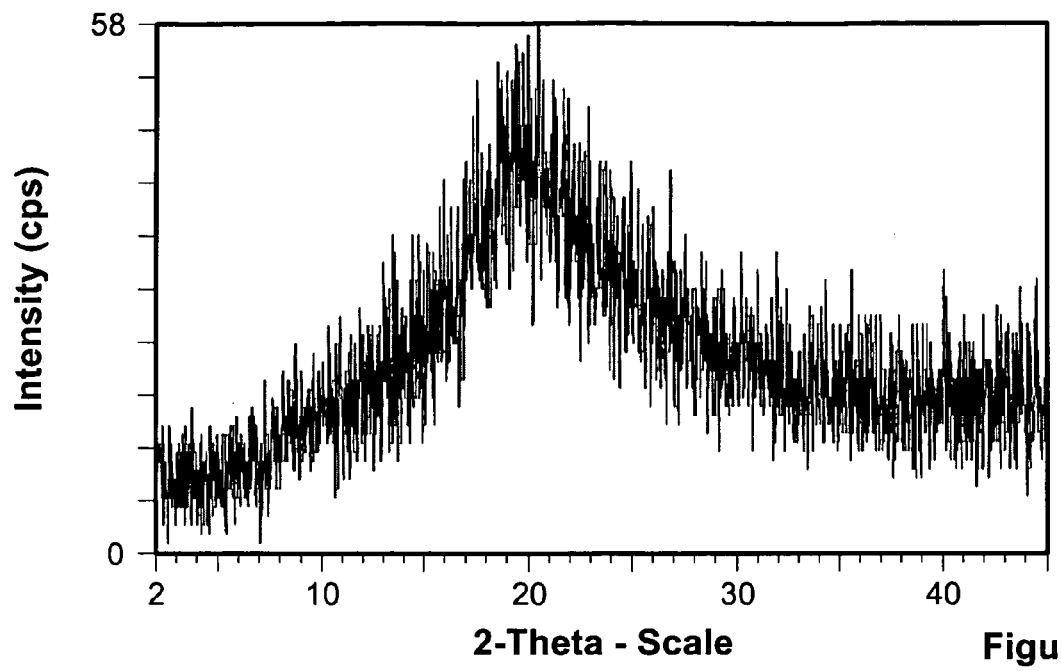
FIG. 55 illustrates the PXRD pattern of a laser treated sample of ezetimibe, atorvastatin free acid, and aspirin in a 2:2:1 ratio by weight.

After the sequenced laser treatment, the lid of the glass Petri dish was removed, and the solution was allowed to dry through slow evaporation at a temperature of 20° C. and 35 percent humidity. The resultant ezetimibe/atorvastatin free acid/aspirin composition dried to a pure transparent glass state. FIG. 55 illustrates the PXRD pattern of the co-amorphous laser treated ezetimibe/atorvastatin free acid/aspirin in a 2:2:1 weight ratio, demonstrating that the composition is non-crystalline.

Figure 56:
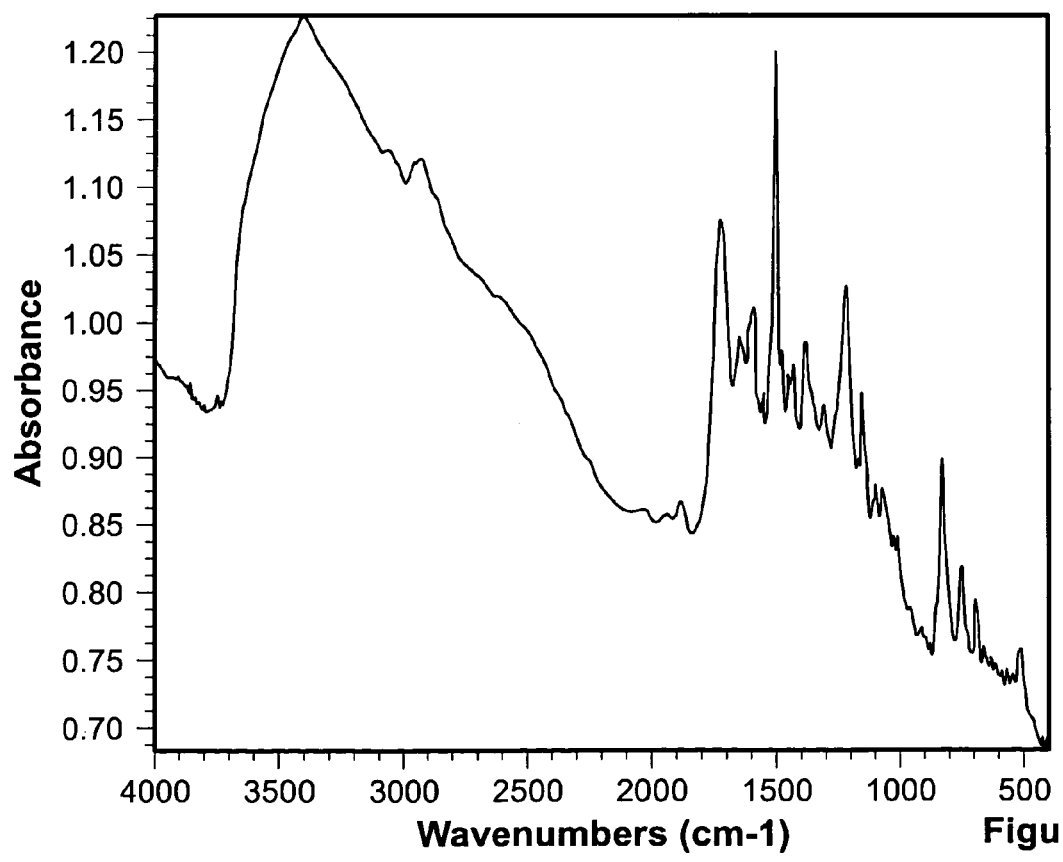
FIG. 56 illustrates the FTIR spectrum of a laser treated sample of ezetimibe, atorvastatin free acid, and aspirin in a 2:2:1 ratio by weight.

The co-amorphous ezetimibe/simvastatin/aspirin composition was then analyzed using FTIR spectroscopy. FIG. 56 illustrates the FTIR spectrum of the co-amorphous laser treated ezetimibe/atorvastatin free acid/aspirin composition, confirming that all three compounds are present and thoroughly mixed. There is also some broadening of a few of the absorbance lines consistent with a non-crystalline form.

The co-amorphous ezetimibe/simvastatin/aspirin composition in a 2:2:1 weight ratio was found to be very stable at room temperature storage conditions with no observed tendency to recrystallization. Given the ease of producing the highly non-crystalline co-amorphous form of this combination, it is likely that a wide range of additional ratios could readily be produced. With the observed ease of producing and stabilizing of the co-amorphous form of this combination of compounds, incrementally increasing production up to the level of large scale manufacturing is expected to be readily accomplished through replication of application modules of this method.

Comparative Example

Ezetimibe/Atorvastatin Free Acid/Aspirin

Figure 65:
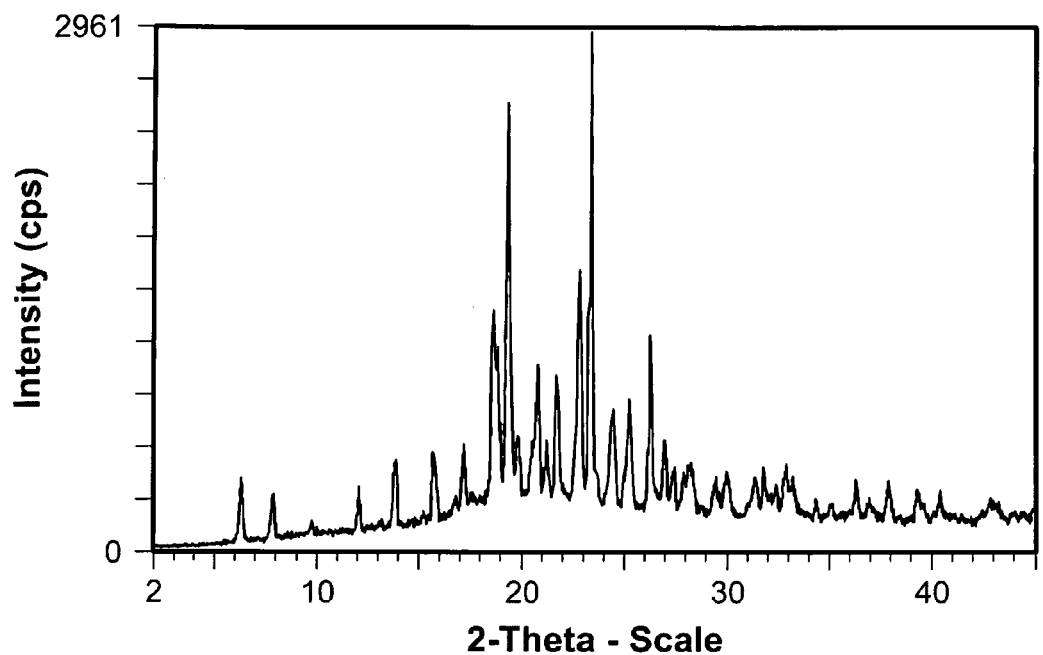
FIG. 65 illustrates the PXRD pattern for a sample of crystalline ezetimibe/atorvastatin free acid/aspirin formed in the process of the invention, with the exception that laser radiation was not applied.

The protocol of Example 13 was repeated with the exception that there was no application of laser radiation. The resulting material was visibly crystalline, which was confirmed by PXRD analysis, which demonstrated that a substantial amount of crystalline material was present. A PXRD pattern for the ezetimibe/atorvastatin free acid/aspirin obtained without the application of the laser radiation is illustrated in FIG. 65. The PXRD pattern of FIG. 65 has the peaks that correspond to PXRD peaks for ezetimibe, atorvastatin free acid, and aspirin illustrated in FIGS. 11, 15, and 1. An FTIR analysis of the resulting ezetimibe/atorvastatin free acid/aspirin was also performed, confirming the material was ezetimibe, atorvastatin free acid, and aspirin. The results demonstrate that the co-amorphous ezetimibe/atorvastatin free acid/aspirin is not an artifact of the experiment, but, instead, is a direct result of the application of the laser radiation in the process of the invention.

Example 14

Preparation of Co-Amorphous Ezetimibe/Rosuvastatin Calcium/Aspirin

Comparative data for interpretation of results for the co-amorphous combinations was obtained from the PXRD and FTIR analysis of untreated reference samples of each of the ezetimibe and rosuvastatin calcium and aspirin and the non-crystalline forms of these compounds treated with the process of the invention. The PXRD pattern of the reference crystalline ezetimibe is illustrated in FIG. 11. The PXRD pattern of laser treated non-crystalline ezetimibe is shown in FIG. 13. The PXRD pattern of the reference sample of rosuvastatin calcium is illustrated in FIG. 25. The PXRD pattern of laser treated non-crystalline rosuvastatin calcium is illustrated in FIG. 26. The PXRD pattern of the reference sample of crystalline aspirin is illustrated in FIG. 1. The PXRD pattern of laser treated non-crystalline aspirin is illustrated in FIG. 3.

The FTIR spectrum of the reference sample of crystalline ezetimibe is illustrated in FIG. 12 with the FTIR spectrum of non-crystalline laser treated ezetimibe. The FTIR spectrum of the reference sample of rosuvastatin calcium is illustrated in FIG. 27. The FTIR spectrum of non-crystalline laser treated rosuvastatin calcium is illustrated in FIG. 28. The FTIR spectrum of the reference sample of crystalline aspirin is illustrated in FIG. 2. The FTIR spectrum of non-crystalline laser treated aspirin is illustrated in FIG. 4.

A 20 mg sample of crystalline ezetimibe, a 20 mg sample of rosuvastatin calcium, and a 10 mg sample of crystalline aspirin were dissolved in 2000 mg of absolute ethanol by stirring at 9000 rpm with a magnetic stirrer for 12 minutes on a heated plate at 140° C. The solution was then cooled to room temperature, and filtered using a syringe to remove any residual crystals. Half of the solution was then decanted into a 60 mm×15 mm glass Petri dish, and covered with a glass lid to provide a solution of 10 mg of ezetimibe, 10 mg of rosuvastatin calcium, and 5 mg of aspirin, i.e., a 2:2:1 weight ratio.

The ezetimibe/rosuvastatin calcium/aspirin solution was first treated with amplitude modulated laser radiation from a diode laser having a central wavelength of about 408 nm 2.5 minutes, and then with amplitude modulated laser radiation from a diode laser having a central wavelength of about 674 nm for 2.5 minutes, rotating the sample slowly through each of the approximately 3 cm diameter expanded beams at a distance of 25 cm from the respective Strachan Device. The 408 μm laser diode beam had a peak power of 2.4 mW after passing through a Thorlabs 5× beam expander and the Strachan Device. Using the Strachan Device, the 408 μm beam was adjusted to the 80 percent phase cancellation level to achieve a measured power of 0.48 mW. The 674 nm beam was passed through a Thorlabs 5× beam expander and the Strachan Device. The output of the 674 nm beam was optically phase cancelled using the Strachan Device to achieve a measured 80 percent reduction of transmitted power to 0.48 mW over a 3 cm diameter beam. Both beams were electronically amplitude modulated at 6.25 MHz.

Figure 57:
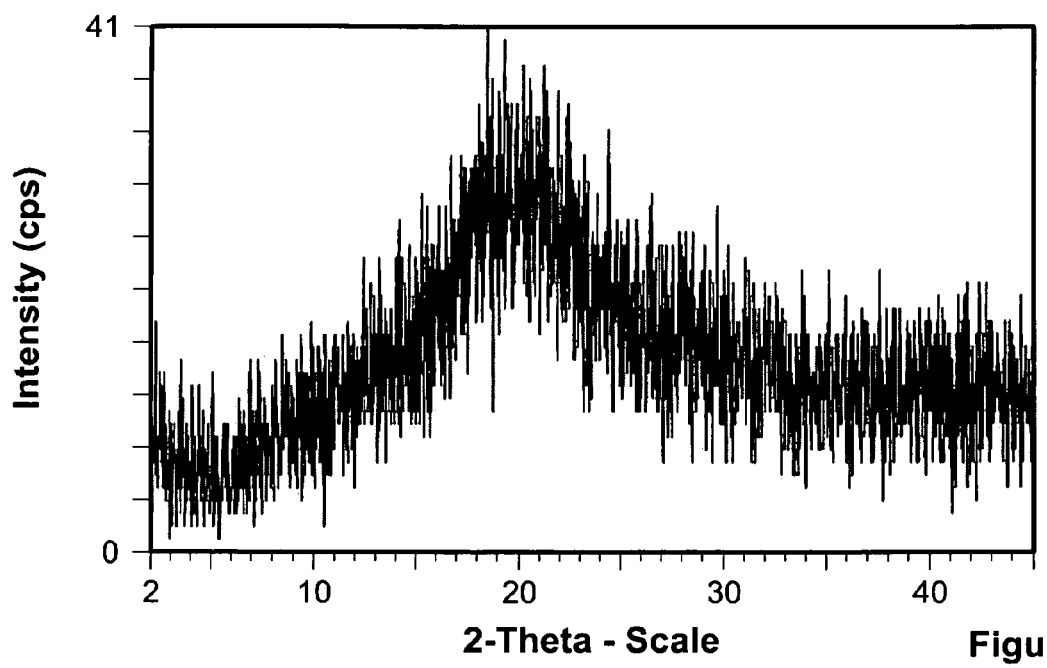
FIG. 57 illustrates the PXRD pattern of a laser treated sample of ezetimibe, rosuvastatin calcium, and aspirin in a 2:2:1 ratio by weight.

After the laser treatment, the lid of the glass Petri dish was removed, and the solution was allowed to dry through slow evaporation at a temperature of 21° C. and 30 percent humidity. The resultant co-amorphous ezetimibe/rosuvastatin calcium/aspirin composition dried to a pure transparent glass state. FIG. 57 illustrates the PXRD pattern of laser treated co-amorphous ezetimibe/rosuvastatin calcium/aspirin composition in a 2:2:1 weight ratio, demonstrating that the composition is non-crystalline.

Figure 58:
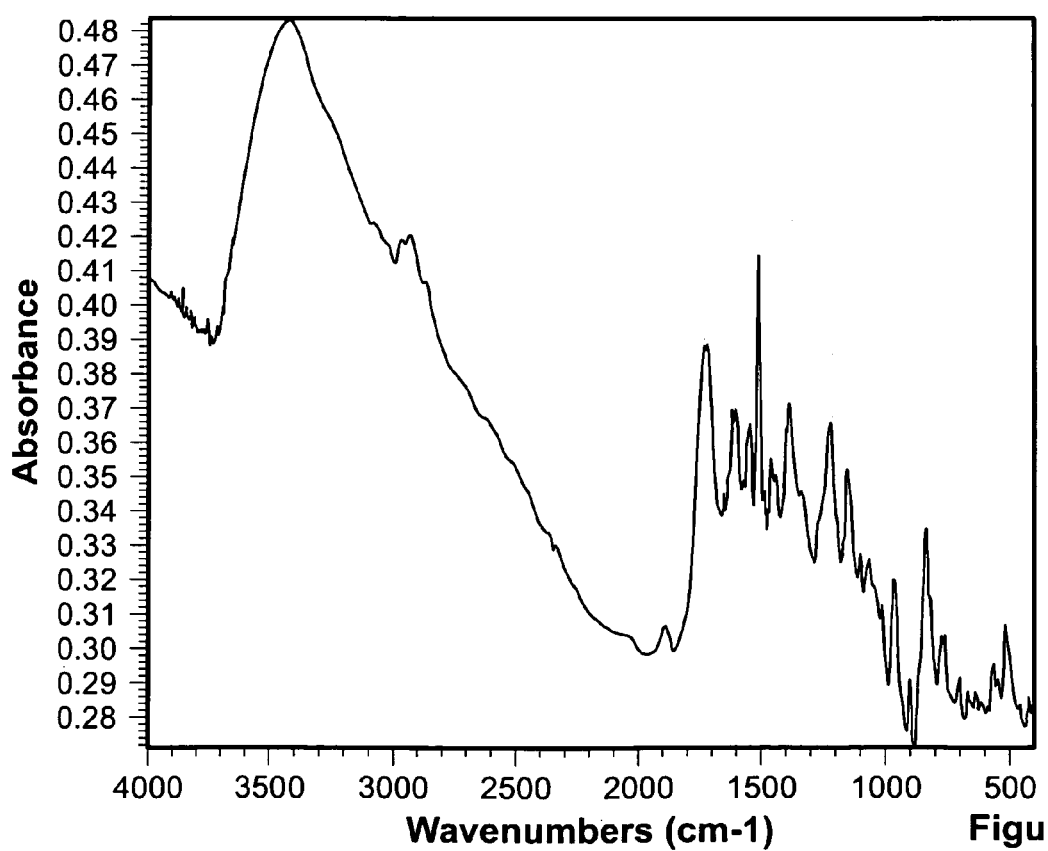
FIG. 58 illustrates the FTIR spectrum of a laser treated sample of ezetimibe, rosuvastatin calcium, and aspirin in a 2:2:1 ratio by weight.

The co-amorphous ezetimibe/rosuvastatin calcium/aspirin composition was then analyzed using FTIR spectroscopy. FIG. 58 illustrates the FTIR spectrum of the laser treated co-amorphous ezetimibe/rosuvastatin calcium/aspirin composition, indicating that all three compounds are present and are thoroughly mixed. There is also some broadening of a few of the absorbance lines consistent with a non-crystalline form.

The co-amorphous ezetimibe/rosuvastatin calcium/aspirin composition in a2:2:1 weight was found to be very stable at room temperature storage conditions with no observed tendency to recrystallize. With the observed ease of producing and stabilizing of the co-amorphous form of this combination of compounds, incrementally increasing production up to the level of large scale manufacturing is expected to be readily accomplished through replication of application modules of this method.

Comparative Example

Ezetimibe/Rosuvastatin Calcium/Aspirin

Figure 66:
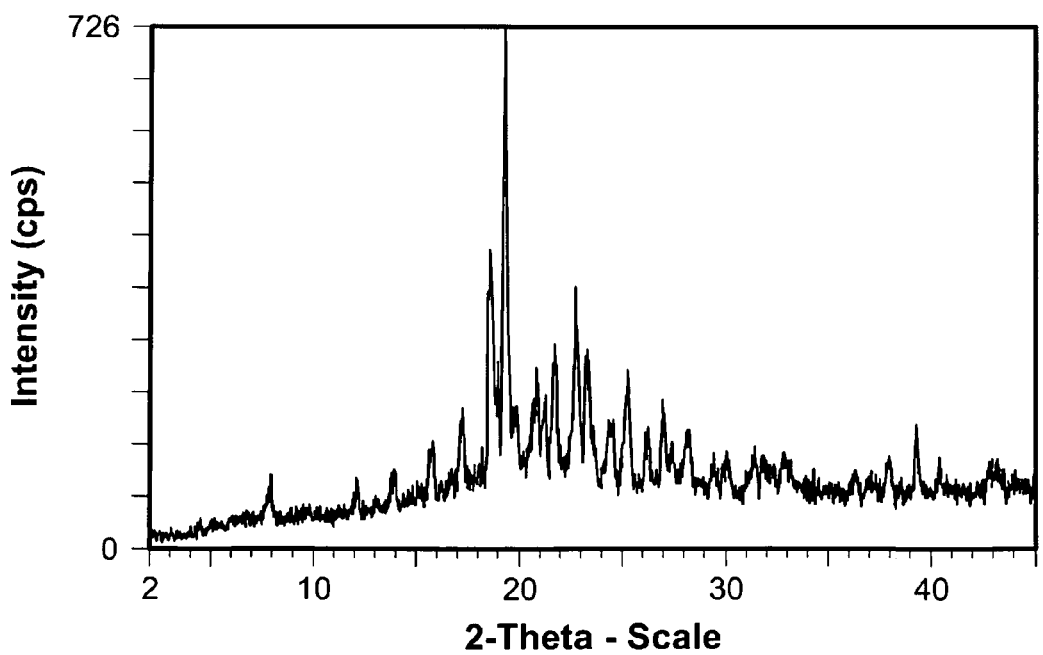
FIG. 66 illustrates the PXRD pattern for a sample of crystalline ezetimibe/rosuvastatin calcium/aspirin formed in the process of the invention, with the exception that laser radiation was not applied.

The protocol of Example 13 was repeated with the exception that there was no application of laser radiation. The resulting material was visibly crystalline, which was confirmed by PXRD analysis, which demonstrated that a substantial amount of crystalline material was present. A PXRD pattern for the ezetimibe/rosuvastatin calcium/aspirin obtained without the application of the laser radiation is illustrated in FIG. 66. The PXRD pattern of FIG. 66 has the peaks that correspond to PXRD peaks for ezetimibe, rosuvastatin calcium, and aspirin illustrated in FIGS. 11, 25, and 1. An FTIR analysis of the resulting ezetimibe/rosuvastatin calcium/aspirin was also performed, confirming the material was ezetimibe, rosuvastatin calcium, and aspirin. The results demonstrate that the co-amorphous ezetimibe/rosuvastatin calcium/aspirin is not an artifact of the experiment, but, instead, is a direct result of the application of the laser radiation in the process of the invention.

Example 15

Preparation of Non-Crystalline Atorvastatin Calcium/Aspirin

The highly non-crystalline glass state of the combination of atorvastatin calcium and aspirin was produced by applying a sequence of long wavelength followed by short wavelength laser light modulated and structured by a Strachan Device. A 60 mg sample of crystalline atorvastatin calcium and a 60 mg sample of crystalline aspirin were dissolved in 1000 mg of absolute ethanol by stirring at 9000 rpm with a magnetic stirrer, while heating to 140° C. for 10 minutes in a stoppered Erlenmeyer flask. The solution was divided equally into six 60 mm×15 mm glass Petri dishes for producing treated and untreated control samples, and each sample was covered with a glass lid. The samples were allowed to cool to room temperature.

One sample of atorvastatin calcium/aspirin in a 1:1 ratio by weight was treated with a sequence of laser radiation modified with a Strachan Device. The first application of amplitude modulated diode laser light was from a diode laser having a central wavelength of 674 µm. The second application of amplitude modulated diode laser light from a diode laser having a central wavelength of 405 µm. The sample was placed above each of the approximately 3 cm diameter expanded beams at a distance of 25 cm from the respective Strachan Devices.

The 674 nm laser diode beam had a peak power of 4.80 mW without optics with about a 50 percent reduction of power to 2.4 mW after passing through a Thorlabs 5× beam expander and the Strachan Device. Using the Strachan Device, the 674 nm beam was adjusted to the 80 percent phase cancellation level to achieve a power of approximately 0.48 mW over a 3 cm diameter expanded beam. The 405 nm beam had a peak power of 11 mW without optics with about a 50 percent reduction of power to 5.5 mW after passing through a Thorlabs 5× beam expander and the Strachan Device. The output of the 405 nm beam was optically phase cancelled using the Strachan Device to achieve a measured 80 percent reduction of transmitted power to approximately 1.1 mW over a 3 cm diameter expanded beam. The 674 nm beam was electronically amplitude modulated at 6.25 Megahertz (MHz) and the 405 nm beam was modulated at 10.8 MHz.

The solution of atorvastatin calcium and aspirin was treated in the covered Petri dish for 2.5 minutes with the 674 nm configuration, then for 2.5 minutes with the 405 nm configuration rotating the sample slowly through each respective beam projected from below the sample. The lid was then removed from the sample and solidification proceeded by slow evaporation at a room temperature of about 20° C.

Figure 69:
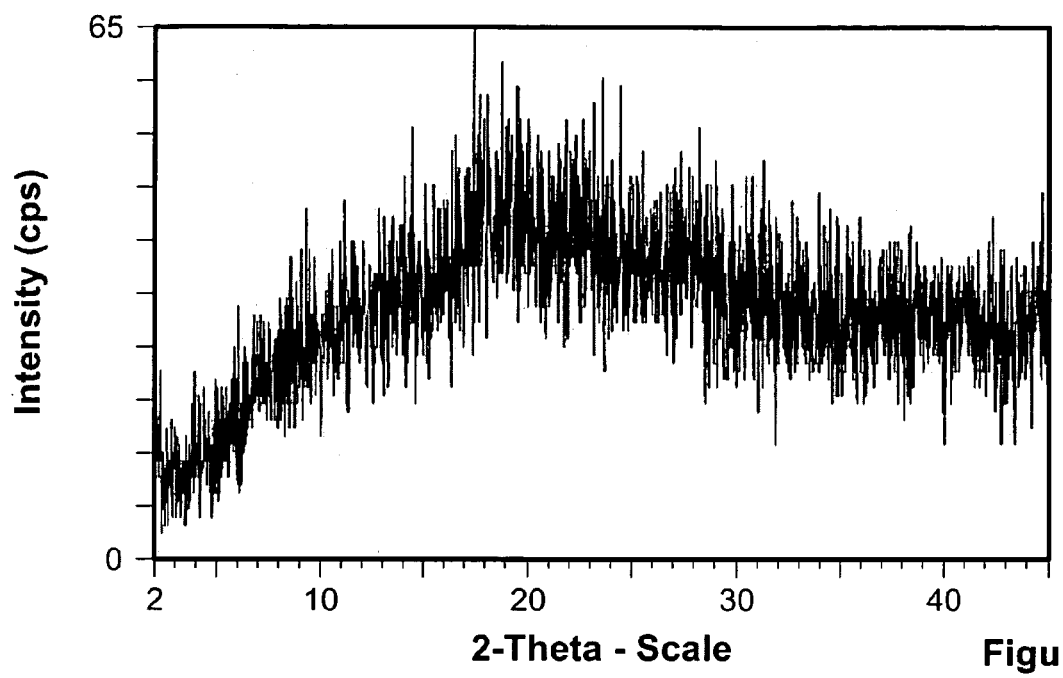
FIG. 69 illustrates the PXRD pattern of a laser treated combination of atorvastatin calcium/aspirin in a 1:1 weight ratio.
Figure 70:
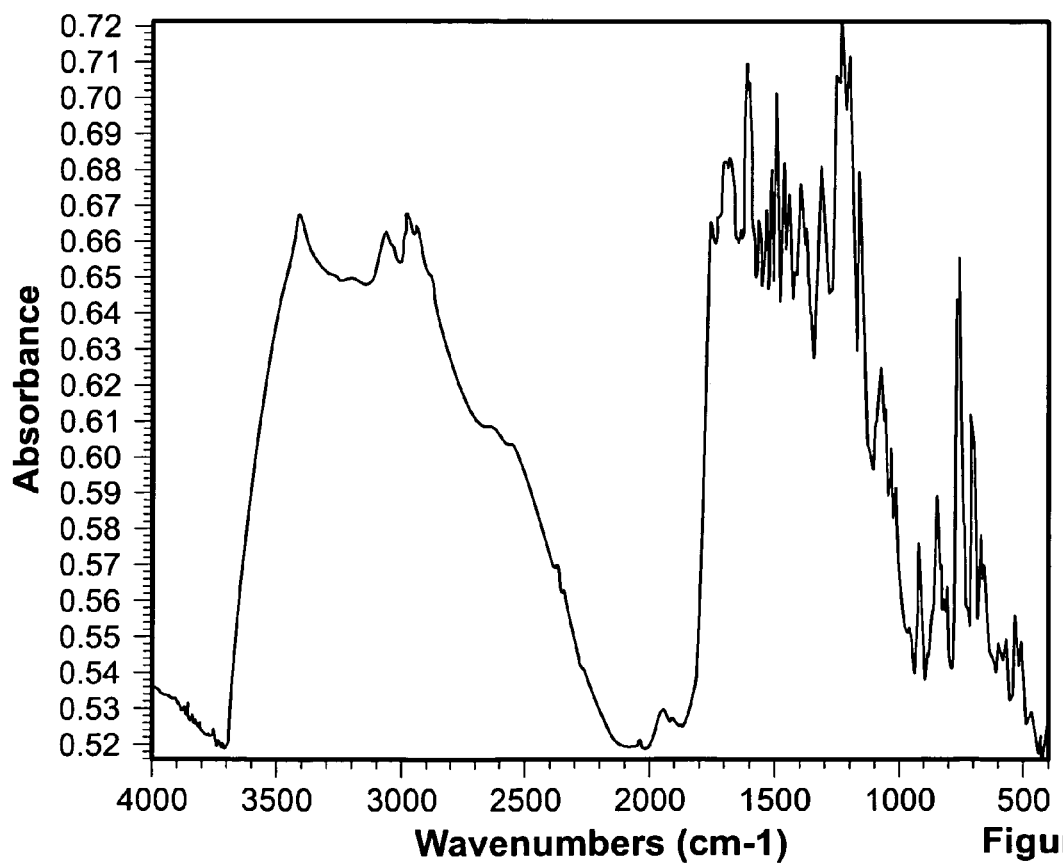
FIG. 70 illustrates the FTIR spectrum a laser treated combination of atorvastatin calcium/aspirin in a 1:1 weight ratio.

The solvent of the sample evaporated, providing a transparent glass appearance throughout the entire sample. FIG. 69 illustrates the PXRD pattern of the combination of atorvastatin calcium and aspirin in a 1:1 weight ratio to be highly non-crystalline. FIG. 70 illustrates the FTIR spectrum of this sample in which the characteristic peaks of the individual compounds are present with broadening of the bands that is typical for non-crystalline forms of compounds.

Comparative Example

Atorvastatin Calcium/Aspirin

Figure 71:
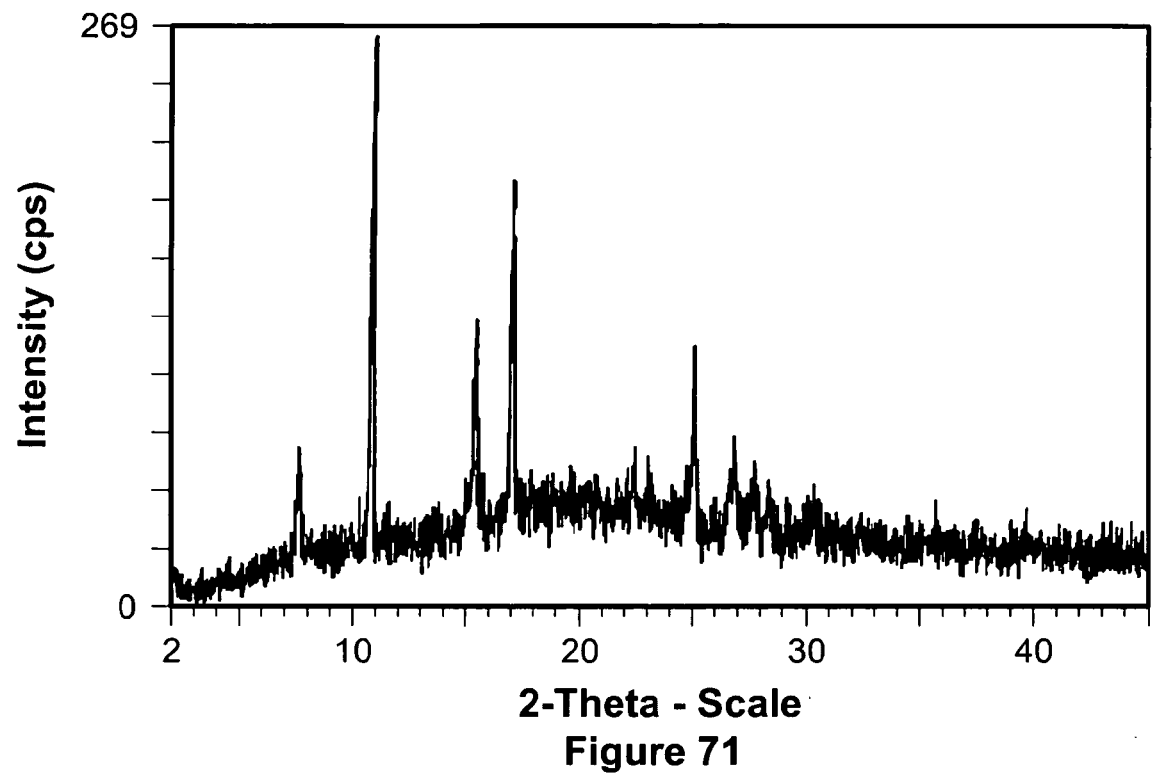
FIG. 71 illustrates the PXRD pattern of a sample of atorvastatin calcium/aspirin in a 1:1 weight ratio formed in the process of the invention, with the exception that laser radiation was not applied.

The protocol of Example 15 was repeated comparative with the exception that there was no application of laser radiation. The resulting material was visibly crystalline, which was confirmed by PXRD analysis, which demonstrated that a substantial amount of crystalline material was present. A PXRD pattern for the atorvastatin calcium/aspirin obtained without the application of the laser radiation is illustrated in FIG. 71. An FTIR analysis of the resulting atorvastatin calcium/aspirin was also performed, confirming the material was a combination of atorvastatin calcium and aspirin. The results demonstrate that the non-crystalline atorvastatin calcium/aspirin is not an artifact of the experiment, but, instead, is a direct result of the application of the laser radiation in the process of the invention.

The molecular weight of atorvastatin calcium is 1155.36 and that of aspirin 180.16. Although the compounds in this combination are in a 1:1 ratio by weight, the smaller relative size of aspirin results in a molar ratio of aspirin to atorvastatin calcium of 6.413:1.

Example 16

Preparation of Atorvastatin Free Acid/Aspirin

The highly non-crystalline glass state of the combination of atorvastatin free acid and aspirin was produced by applying a sequence of short wavelength followed by long wavelength laser light modulated and structured by a Strachan Device. A 60 mg sample of crystalline atorvastatin free acid and a 120 mg sample of crystalline aspirin were dissolved in 1800 mg of absolute ethanol by stirring at 9000 rpm with a magnetic stirrer, while heating to 140° C. for 10 minutes in a stoppered Erlenmeyer flask. The solution was filtered, and then divided equally into 6 polystyrene Petri dishes for producing treated and untreated control samples. Each sample was covered with a polystyrene lid. The samples were allowed to cool to room temperature.

The exemplary sample of atorvastatin free acid/aspirin in a weight ratio of 1:2 was treated with a sequence of laser radiation modified with a Strachan Device. The first application of amplitude modulated diode laser light was from a diode laser having a central wavelength of 405 nm. The second application of amplitude modulated diode laser light from a diode laser having a central wavelength of 674 μm. The sample was placed above an approximately 3 cm expanded beam at a distance of 25 cm from the Strachan Device.

The 405 μm beam had a peak power of 11 mW without optics with about a 50 percent reduction of power to 5.5 mW after passing through a Thorlabs 5× beam expander and the Strachan Device. The output of the 405 μm beam was optically phase cancelled using the Strachan Device to achieve a measured 90 percent reduction of transmitted power to approximately 0.55 mW over a 3 cm diameter expanded beam. The 674 nm laser diode beam had a peak power of 4.80 mW without optics with about a 50 percent reduction of power to 2.4 mW after passing through a Thorlabs 5× beam expander and the Strachan Device. Using the Strachan Device, the 674 nm beam was adjusted to the 80 percent phase cancellation level to achieve a power of approximately 0.48 mW over a 3 cm diameter expanded beam. The 405 nm beam was electronically amplitude modulated at 10.8 MHz, and the 674 nm beam was modulated at 46.2 MHz.

The solution of atorvastatin free acid and aspirin was treated in the covered Petri dish for 2.5 minutes with the 405 nm laser radiation modulated by the Strachan Device, then for 2.5 minutes with the 674 nm configuration with the samples stationary as the 3 cm beam covered the entire sample dish. The lid was then removed from the sample and solidification proceeded by slow evaporation at a room temperature of about 22° C.

Figure 72:
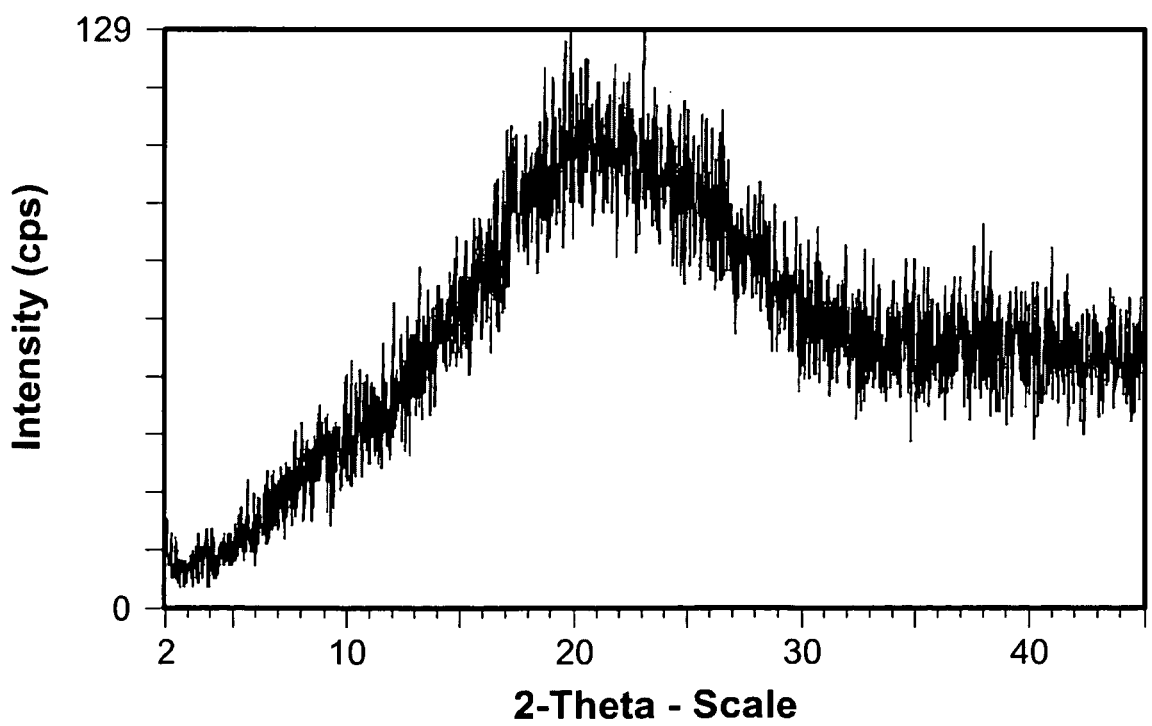
FIG. 72 illustrates the PXRD pattern of a laser treated combination of atorvastatin free acid/aspirin in a 1:2 weight ratio.

The solvent evaporated, providing a sample having a transparent glass appearance throughout the entire sample. FIG. 72 illustrates the PXRD pattern of the 1:2 weight ratio combination of atorvastatin free acid and aspirin to be highly non-crystalline. An FTIR analysis of this sample demonstrated that the characteristic peaks of the individual compounds are present with broadening of the bands that is typical for non-crystalline forms of compounds.

Comparative Example

Atorvastatin Free Acid/Aspirin

Figure 73:
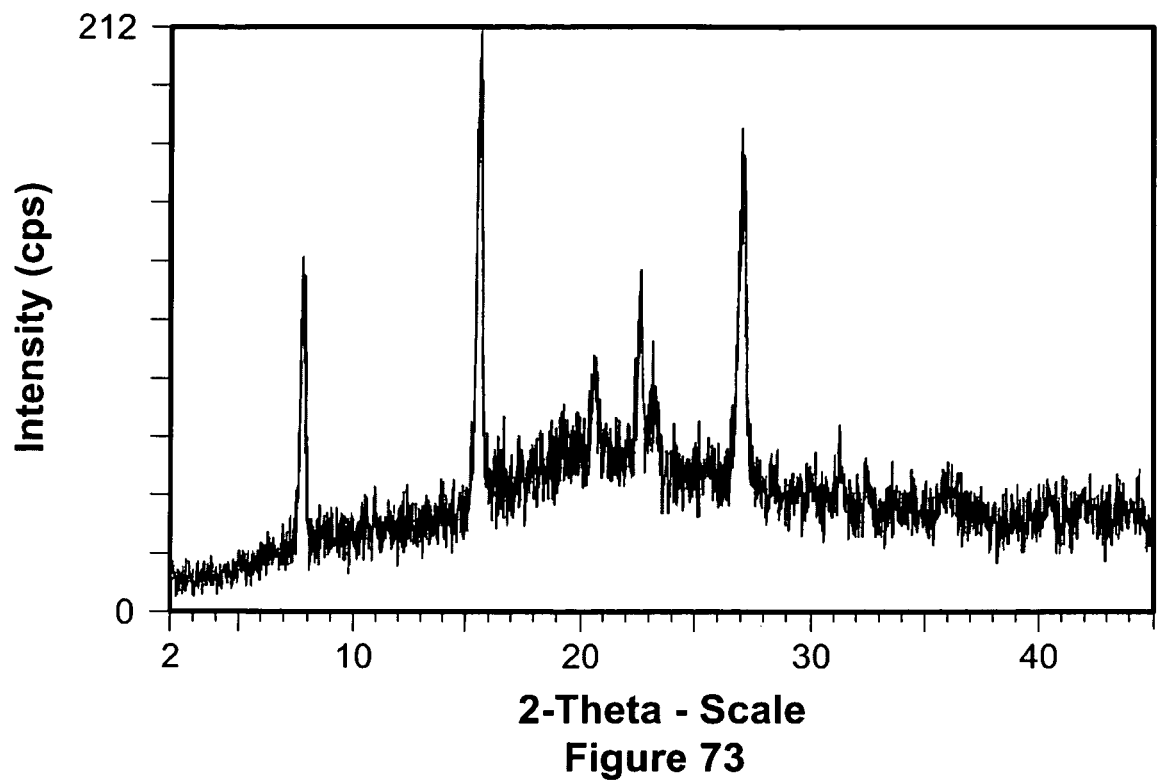
FIG. 73 illustrates the PXRD pattern of a sample of atorvastatin free acid/aspirin in a 1:2 weight ratio formed in the process of the invention, with the exception that laser radiation was not applied.

The protocol of Example 16 was repeated comparative with the exception that there was no application of laser radiation. The resulting material was visibly crystalline, which was confirmed by PXRD analysis, which demonstrated that a substantial amount of crystalline material was present. A PXRD pattern for the atorvastatin free acid/aspirin obtained without the application of the laser radiation is illustrated in FIG. 73. An FTIR analysis of the resulting atorvastatin free acid/aspirin was also performed, confirming the material was a combination of atorvastatin free acid and aspirin. The results demonstrate that the non-crystalline atorvastatin free acid/aspirin combination is not an artifact of the experiment, but, instead, is a direct result of the application of the laser radiation in the process of the invention.

The molecular weight of atorvastatin free acid is 558.64. Although the compounds in this combination are in a 1:2 ratio by weight, the smaller relative size of aspirin results in a molar ratio of aspirin to atorvastatin free acid of 6.202:1.

Example 17

Preparation of Rosuvastatin Calcium/Aspirin

The highly non-crystalline glass state of the combination of rosuvastatin calcium and aspirin was produced by applying a repeated sequence of short wavelength followed by long wavelength laser light modulated and structured by a Strachan Device. A 60 mg sample of rosuvastatin calcium and a 60 mg sample of crystalline aspirin were dissolved in 1200 mg of absolute ethanol by stirring at 9000 rpm with a magnetic stirrer, while heating to 140° C. for 10 minutes in a stoppered Erlenmeyer flask. The solution was filtered, and then divided equally into 6 polystyrene Petri dishes for producing treated and untreated control samples and each sample was covered with a polystyrene lid. The samples were allowed to cool to room temperature.

The exemplary sample of rosuvastatin/aspirin in a 1:1 ratio by weight was treated with a repeated sequence of laser radiation modified with a Strachan Device. The first application of amplitude modulated diode laser light was from a diode laser having a central wavelength of 405 nm. The second application of amplitude modulated diode laser light from a diode laser having a central wavelength of 674 nm. The sample was placed above an approximately 3 cm expanded beam at a distance of 25 cm from the Strachan Device.

The 405 μm beam had a peak power of 11 mW without optics with about a 50 percent reduction of power to 5.5 mW after passing through a Thorlabs 5× beam expander and the Strachan Device. The output of the 405 nm beam was optically phase cancelled using the Strachan Device to achieve a measured 90 percent reduction of transmitted power to approximately 0.55 mW over a 3 cm diameter expanded beam. The 674 μm laser diode beam had a peak power of 4.80 mW without optics with about a 50 percent reduction of power to 2.4 mW after passing through a Thorlabs 5× beam expander and the Strachan Device. Using the Strachan Device, the 674 μm beam was adjusted to the 80 percent phase cancellation level to achieve a power of approximately 0.48 mW over a 3 cm diameter expanded beam. The 405 nm beam was electronically amplitude modulated at 10.8 MHz and the 674 μm beam was modulated at 46.2 MHz.

The solution of rosuvastatin calcium and aspirin was treated in the covered Petri dish for 1 minute with the 405 nm configuration, then for 1 minute with the 674 μm configuration with the samples stationary as each of the 3 cm beams covered the entire sample dish. This was repeated for two more identical cycles for a total treatment duration of 6 minutes. The lid was then removed from the sample and solidification proceeded by slow evaporation at a room temperature of about 23° C.

Figure 74:
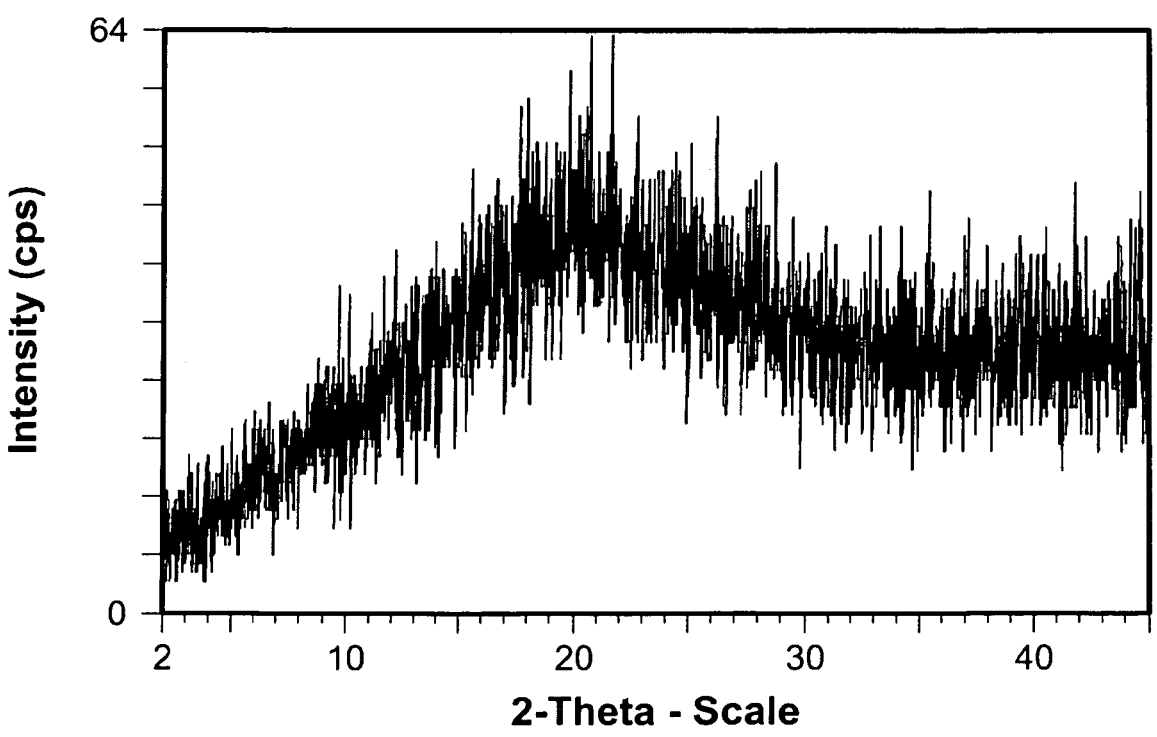
FIG. 74 illustrates the PXRD pattern of a laser treated combination of rosuvastatin calcium/aspirin in a 1:1 weight ratio.

The solvent in the sample evaporated, providing a transparent glass appearance throughout the entire sample. FIG. 74 illustrates the PXRD pattern of the 1:1 weight ratio combination of rosuvastatin calcium and aspirin to be highly non-crystalline. An FTIR analysis of this sample demonstrates that the characteristic peaks of the individual compounds are present with broadening of the bands that is typical for non-crystalline forms of compounds.

Comparative Example

Rosuvastatin Calcium/Aspirin

Figure 75:
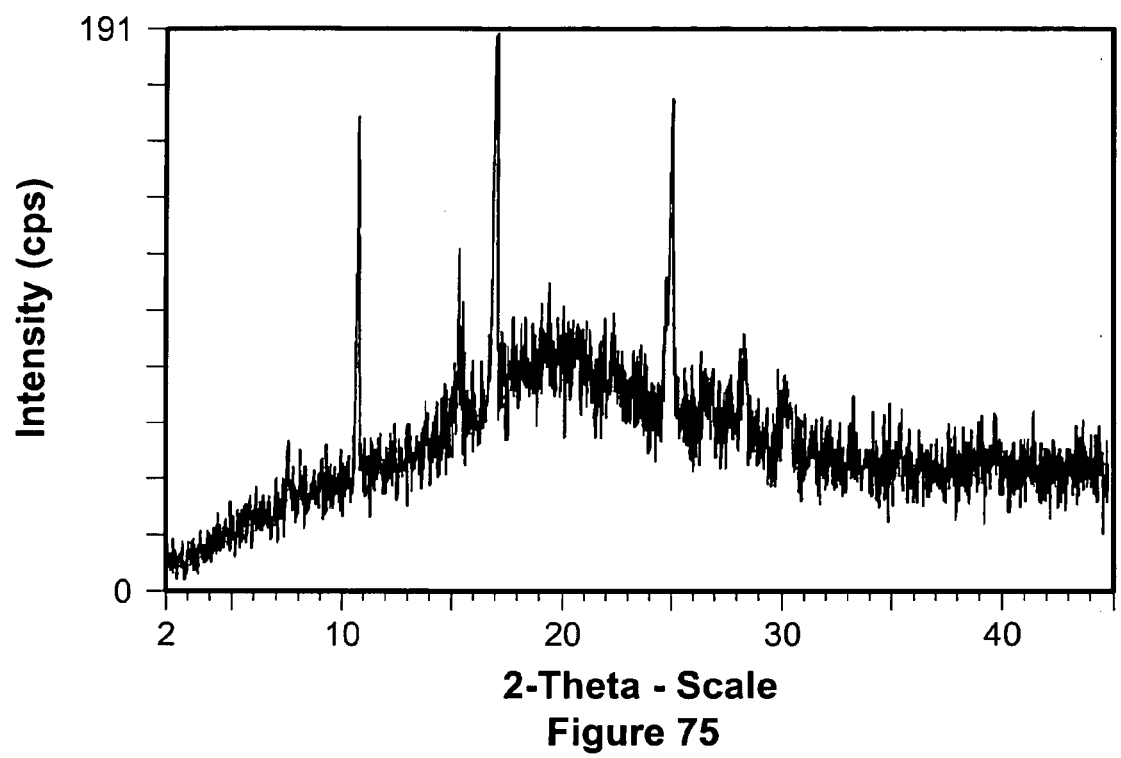
FIG. 75 illustrates the PXRD pattern of a sample of rosuvastatin calcium/aspirin in a 1:1 weight ratio formed in the process of the invention, with the exception that laser radiation was not applied.

The protocol of Example 17 was repeated comparative with the exception that there was no application of laser radiation. The resulting material was visibly crystalline, which was confirmed by PXRD analysis, which demonstrated that a substantial amount of crystalline material was present. A PXRD pattern for the rosuvastatin calcium/aspirin obtained without the application of the laser radiation is illustrated in FIG. 75. An FTIR analysis of the resulting rosuvastatin calcium/aspirin was also performed, confirming the material was a combination of rosuvastatin calcium and aspirin. The results demonstrate that the non-crystalline combination of rosuvastatin calcium and aspirin is not an artifact of the experiment, but, instead, is a direct result of the application of the laser radiation in the process of the invention.

The molecular weight of rosuvastatin calcium is 1001.14. Although the compounds in this combination are in a 1:1 ratio by weight, the smaller relative size of aspirin results in a molar ratio of aspirin to atorvastatin free acid of 5.557:1.

Example 18

Preparation of Simvastatin/Aspirin

The highly non-crystalline glass state of the combination of simvastatin and aspirin was produced by applying a repeated sequence of short wavelength followed by long wavelength laser light modulated and structured by a Strachan Device. A 60 mg sample of crystalline simvastatin and a 30 mg sample of crystalline aspirin were dissolved in 900 mg of absolute ethanol by stirring at 9000 rpm with a magnetic stirrer, while heating to 140° C. for 10 minutes in a stoppered Erlenmeyer flask. The solution was filtered, and then divided equally into 6 polystyrene Petri dishes for producing treated and untreated control samples. Each sample was covered with a polystyrene lid. The samples were allowed to cool to room temperature.

The exemplary sample of simvastatin/aspirin in a 2:1 ratio by weight was treated with a repeated sequence of laser radiation modified with a Strachan Device. The first application of amplitude modulated diode laser light was from a diode laser having a central wavelength of 405 μm. The second application of amplitude modulated diode laser light from a diode laser having a central wavelength of 674 μm. The sample was placed above each of the approximately 3 cm expanded beams at a distance of 25 cm from the Strachan Device.

The 405 μm beam had a peak power of 11 mW without optics with about a 50 percent reduction of power to 5.5 mW after passing through a Thorlabs 5× beam expander and the Strachan Device. The output of the 405 nm beam was optically phase cancelled using the Strachan Device to achieve a measured 90 percent reduction of transmitted power to approximately 0.55 mW over a 3 cm diameter expanded beam. The 674 nm laser diode beam had a peak power of 4.80 mW without optics with about a 50 percent reduction of power to 2.4 mW after passing through a Thorlabs 5× beam expander and the Strachan Device. Using the Strachan Device, the 674 nm beam was adjusted to the 80 percent phase cancellation level to achieve a power of approximately 0.48 mW over a 3 cm diameter expanded beam. The 405 nm beam was electronically amplitude modulated at 10.8 MHz and the 674 nm beam was modulated at 46.2 MHz.

The solution of simvastatin and aspirin was treated in the covered Petri dish for 1 minute with the 405 nm configuration, then for 1 minute with the 674 nm configuration with the samples stationary as each of the 3 cm diameter beams covered the entire sample dish. This was repeated for two more identical cycles for a total treatment duration of 6 minutes. The lid was then removed from the sample and solidification proceeded by slow evaporation at a room temperature of 21° C.

Figure 76:
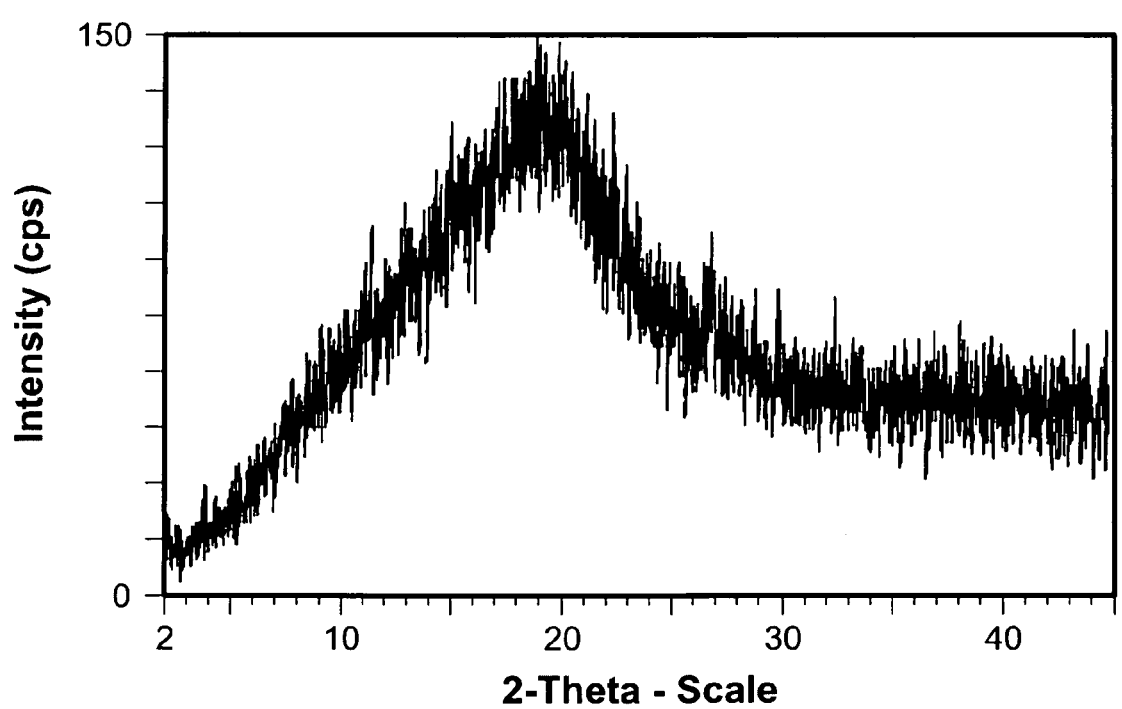
FIG. 76 illustrates the PXRD pattern of a laser treated combination of simvastatin/aspirin in a 2:1 weight ratio.
Figure 77:
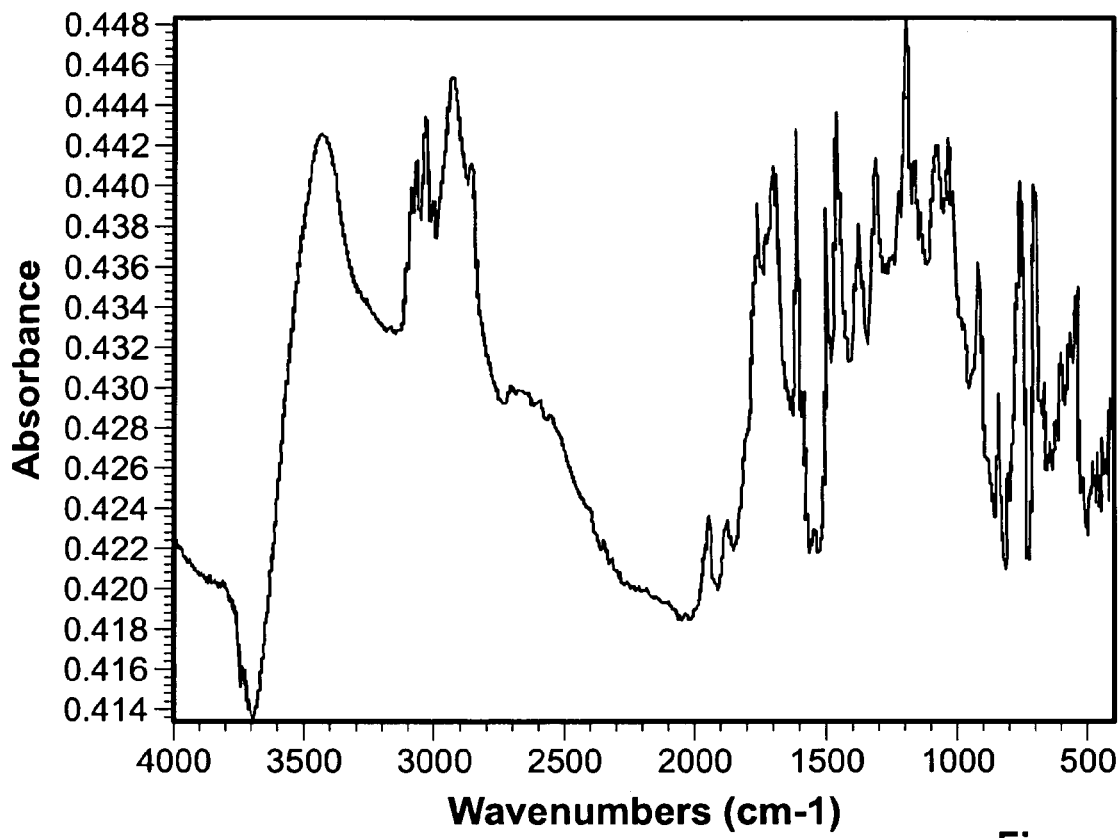
FIG. 77 illustrates the FTIR spectrum a laser treated combination of simvastatin/aspirin in a 2:1 weight ratio.

The solvent in the sample evaporated, providing a transparent glass appearance throughout the entire sample. FIG. 76 illustrates the PXRD pattern of the 2:1 weight ratio combination of simvastatin and aspirin to be highly non-crystalline. FIG. 77 illustrates the FTIR analysis of this sample to indicate that the characteristic peaks of the individual compounds are present with broadening of the bands that is typical for non-crystalline forms of compounds.

Comparative Example

Simvastatin/Aspirin

Figure 78:
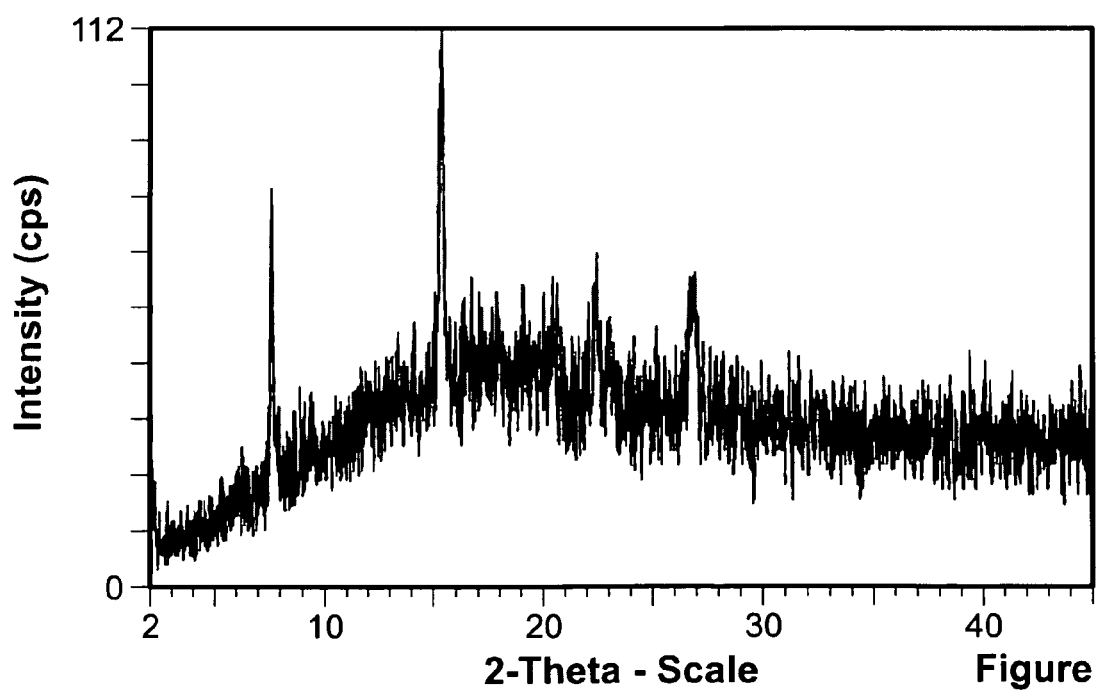
FIG. 78 illustrates the PXRD pattern of a sample of simvastatin/aspirin in a 2:1 weight ratio formed in the process of the invention, with the exception that laser radiation was not applied.

The protocol of Example 18 was repeated comparative with the exception that there was no application of laser radiation. The resulting material was visibly crystalline, which was confirmed by PXRD analysis, which demonstrated that a substantial amount of crystalline material was present. A PXRD pattern for the simvastatin/aspirin obtained without the application of the laser radiation is illustrated in FIG. 78. An FTIR analysis of the resulting simvastatin/aspirin was also performed, confirming the material was a combination of simvastatin and aspirin. The results demonstrate that the non-crystalline simvastatin/aspirin is not an artifact of the experiment, but, instead, is a direct result of the application of the laser radiation in the process of the invention.

The molecular weight of simvastatin is 418.56. Although the compounds in this combination are in a 1:1 ratio by weight, the smaller relative size of aspirin results in a molar ratio of aspirin to atorvastatin free acid of 1.162:1.

The ability to stabilize a room temperature glass form of aspirin into which single molecules or small clusters of molecules are embedded offers marked enhancement of solubility for the embedded compounds. To the degree a compound is hydrophobic and of low aqueous solubility, surrounding this compound in a matrix of glass aspirin of much higher solubility, the rate of dissolution, bioavailability, and absorption of the hydrophobic compound or compounds will be enhanced. The greater the relative molar ratio of aspirin and the higher the intrinsic solubility of the embedded compound, the greater the likely solubility of the co-amorphous combination.

As an example, the solubility of crystalline simvastatin in water is 0.03 mg/ml, which is relatively low. In contrast, the solubility of crystalline aspirin in water is 3.33 mg/ml at room temperature, a 111-fold differential. By producing both simvastatin and aspirin in an amorphous state, which often increases the solubility of hydrophobic compounds by a factor of 2- to 8-fold and embedding the simvastatin with a matrix of non-crystalline aspirin, it is expected that the solubility of simvastatin will be significantly increased.

For the particularly high molar ratios achieved with the co-amorphous combination of aspirin with atorvastatin calcium, atorvastatin free acid, and rosuvastatin calcium, aspirin molecules can completely surround individual or a few molecules of the embedded statin. In this manner pockets are formed within the non-crystalline matrix of aspirin at the scale of nanometers, and this system could be described as a glass aspirin nanopocket packaging and delivery system for relatively less soluble compounds. The combination of aspirin (or other suitable matrix compound that could be prepared through this method) with a statin can create an environment that confers greater long-term stability of the non-crystalline state of the statin or other hydrophobic or poorly soluble compound or compounds thus embedded.

The pharmacological benefit of the statins is primarily focused on reducing total and LDL cholesterol. Use of statins has been associated with the observation of the reduction of systemic inflammatory markers such as C-reactive protein. Reduced total and especially LDL cholesterol levels as well as decreased systemic inflammation have been identified as factors that improve cardiovascular health outcomes. Aspirin has well demonstrated effects on reducing the tendency to vascular clot formation that is independently associated with improved cardiovascular outcomes. The particular pairing of a statin and aspirin together in a co-absorbed matrix will offer additive and even synergistic benefits for cardiac and vascular health.

Particularly pronounced therapeutic enhancement is anticipated for atorvastatin. With absorption of only 30 percent, solubility enhancement may promote considerably greater initial absorption. To the degree that absorption is enhanced, the current systemic bioavailability of 12 percent may be commensurately increased. The ability to achieve comparable or greater clinical benefits at lower doses can reduce the side effect profile and make statins acceptable to a wider number of persons who may benefit from the pharmacology of statins.

To achieve large scale production of this form, microencapsulation permits generation and sealing of smaller particle sizes that are intrinsically more stable than larger particles composed of the non-crystalline aspirin and statins or other compounds in a co-amorphous combination. Microencapsulation will facilitate retaining stability during long term storage over a wider range of temperature and humidity. Microencapsulation techniques are well known in the art.

Whereas ezetimibe and the statins described in this disclosure were readily produced in the non-crystalline state as individual compounds and as co-amorphous glass combinations of ezetimibe and a statin, when aspirin was added to this combination there was a concentration threshold above which a tendency to crystallization occurred. When ezetimibe and a statin were combined in an equal ratio by weight and aspirin was added to produce a 1:1:1 ratio of ezetimibe/statin/aspirin, fine threads of crystals appeared in an otherwise transparent glass matrix, most likely reflecting aggregation of crystallizing aspirin. When aspirin was reduced in proportion to the 2:2:1 weight ratio for the ezetimibe/statin/aspirin composition, a stable co-amorphous glass form was readily produced with the process of the invention. Thus, it appears that this method can produce stable co-amorphous combinations of ezetimibe and a statin in a wide range of ratios and aspirin can be added to the combination at a level of up to at least about 20 percent by weight to produce a stable highly co-amorphous combination of ezetimibe, a statin, and plus aspirin.

The molecular structures of the compounds treated in the examples of the invention describe above are significantly different, as shown below.

Aspirin,

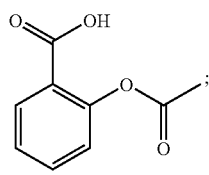

Simvastatin,

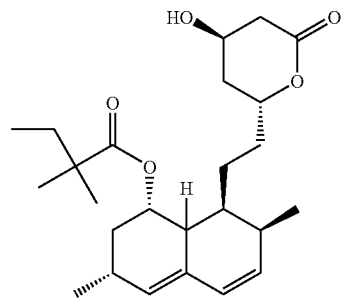

Ezetimibe,

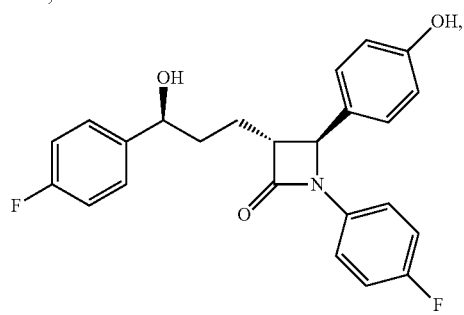

Atorvastatin free acid,

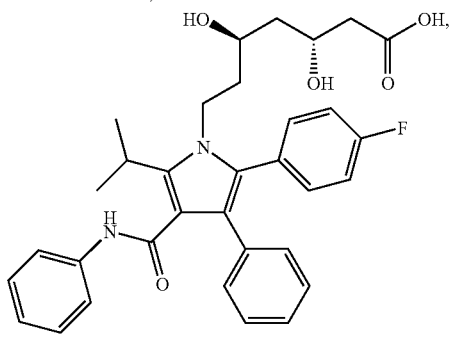

Atorvastatin calcium,

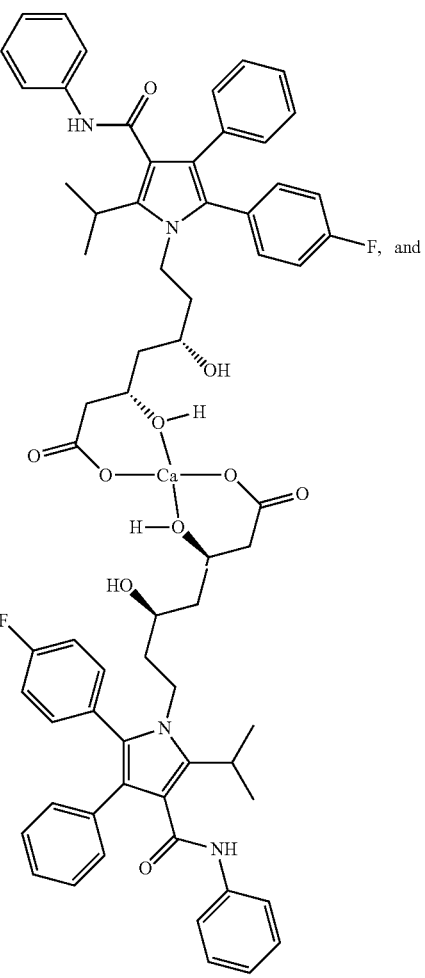

F, and

Rosuvastatin calcium,

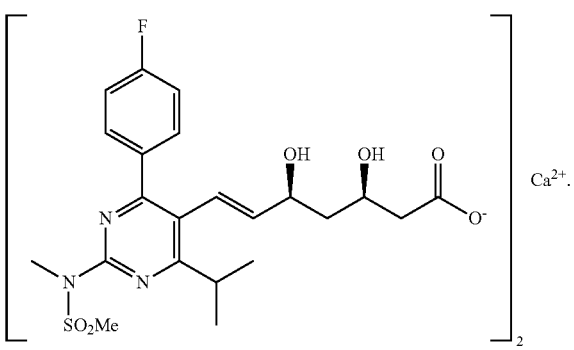

As the molecular structures for those compounds differ significantly, those skilled in the art would expect the molecular orbitals and spectroscopic absorption bands of each of those compounds to also be significantly different, such that different laser wavelengths were required to effect the observed changes. However, as disclosed above, non-crystalline and co-amorphous compositions of those compounds were prepared by treatment with the process of the invention. For each composition in each example, the laser radiation from diode lasers emitting at essentially the same two wavelengths was modified by transmission through a Strachan Device, and applied to the composition. That is, there was no significant difference in the emission spectra of the lasers used in each example. One of the diode lasers used in the examples emitted laser radiation in the violet range having a wavelength centered at about 408 μm (Examples 1 to 14) or at about 405 μm (Examples 15 to 18). The other diode laser used in the examples emitted laser radiation having a wavelength centered at about 674 nm. Each example provided a non-crystalline form of the composition, despite the differences in molecular structure.

As discussed above, without being bound by theory, it is believed that the output bandwidth of the lasers is broadened by the short pulse length. This follows from the Uncertainty Principle. As a result, the short pulses of laser light are believed to provide photons that interact with the different vibrational and/or electronic states of the compositions to provide the non-crystalline forms. Lasers having an emission that corresponds to specific absorption bands of the compositions are not required. Accordingly, it is submitted that the process of the invention can be readily extended to other pharmaceutical and organic compositions.

What is claimed is:

1. A co-amorphous pharmaceutical composition, comprising a solid non-crystalline, co-amorphous blend of at least two pharmaceutical compounds, wherein the pharmaceutical compounds are selected from the group consisting of aspirin, ezetimibe, simvastatin, atorvastatin free acid, atorvastatin calcium, and rosuvastatin calcium.

2. The co-amorphous pharmaceutical composition according to claim 1, selected from the group consisting of ezetimibe/simvastatin, ezetimibe/atorvastatin calcium, ezetimibe/atorvastatin free acid, ezetimibe/rosuvastatin calcium, ezetimibe/simvastatin/aspirin, ezetimibe/atorvastatin calcium/aspirin, ezetimibe/atorvastatin free acid/aspirin, ezetimibe/rosuvastatin calcium/aspirin, and co-amorphous compositions comprising at least one statin and aspirin.

3. The co-amorphous pharmaceutical composition according to claim 1, selected from the group consisting of atorvastatin free acid/aspirin, atorvastatin calcium/aspirin, simvastatin/aspirin, and rosuvastatin calcium/aspirin.

4. The co-amorphous pharmaceutical composition according to claim 1, wherein the pharmaceutical composition is homogeneous.

5. A process for preparing a solid non-crystalline composition comprising at least one organic compound, the process comprising applying laser radiation from at least two different lasers to a solution of the at least one organic compound in a solvent, and evaporating the solvent, wherein the laser radiation has pulses with an effective average pulse length of no more than about $10^{-9}$ seconds, and the laser radiation from each laser has a different wavelength.

6. The process according to claim 5, wherein the at least one organic compound is a pharmaceutical composition.

7. The process according to claim 5, wherein the at least one organic compound is selected from the group consisting of aspirin, ezetimibe, simvastatin, atorvastatin free acid, atorvastatin calcium, rosuvastatin calcium, and mixtures thereof.

8. The process according to claim 5, wherein at least one of the lasers emits visible light.

9. The process according to claim 5, wherein one laser emits radiation in the near UV to blue range, and one laser emits radiation in the red to near IR range.

10. The process according to claim 5, wherein one laser emits radiation having a wavelength in the range of from about 400 to about 470 nm, and one laser emits radiation having a wavelength in the range of from about 620 to about 680 nm.

11. The process according to claim 5, wherein the laser radiation is modified with a Strachan Device, the Strachan Device comprising a first diffraction grating and a second diffraction grating and a refractive element positioned between the first and second diffraction gratings.

12. The process according to claim 11, wherein the lasers are diode lasers.

13. The process according to claim 5, wherein the laser radiation has an effective average pulse length of no more than about $10^{-12}$ seconds.

14. The process according to claim 5, wherein the laser radiation has an effective average pulse length of no more than about $10^{-15}$ seconds.

15. The process according to claim 5, further comprising applying the laser pulses from at least two different lasers simultaneously.

16. The process according to claim 5, further comprising applying laser pulses from at least two different lasers in alternating sequences.

17. The process according to claim 5, wherein the solvent is an alcohol.

18. The process according to claim 5, wherein the solvent is an absolute alcohol.

19. The process according to claim 5, further comprising obtaining a solution of the at least one organic compound in a solvent;
placing the solution of the at least one organic compound in a covered container;
applying the laser radiation pulses to the solution; and
evaporating at least a portion of the solvent while applying the laser pulses, thereby forming the non-crystalline composition.

20. The process according to claim 19, further comprising heating the solution of the at least one organic compound during the application of the laser pulses.

21. The process according to claim 20, further comprising heating the solution to a temperature of about 100° C.

22. The process according to claim 19, further comprising applying the laser radiation to the solution of the at least one organic compound until the evaporation of the solvent is completed.

23. The process according to claim 22, further comprising cooling the solution of the at least one organic compound to room temperature as the solvent evaporates.

24. The process according to claim 19, further comprising preventing evaporation of solvent for a period of time after the application of laser radiation is initiated, and then evaporating solvent while the application of laser pulses is continued.

25. The process according to claim 24, further comprising applying the laser radiation of the solution until the evaporation of the solvent is completed.

26. The process according to claim 19, further comprising applying the laser radiation from at least two different lasers simultaneously.

27. The process according to claim 19, further comprising applying laser pulses from at least two different lasers in alternating sequences.

28. A process for preparing a solid non-crystalline co-amorphous composition, the process comprising:

passing laser radiation through a Strachan Device, the Strachan Device comprising a first diffraction grating and a second diffraction grating and a refractive element positioned between the first and second diffraction gratings, canceling a portion of the laser radiation by destructive interference, and producing effective pulses of laser radiation by constructive interference;

applying the laser radiation passed through the Strachan Device to a solution comprising at least two pharmaceutical compositions in a solvent; and evaporating the solvent.

29. The process according to claim 28, wherein the pulses of laser radiation have an effective average pulse length of no more than about $10^{-9}$ seconds.

30. The process according to claim 28, wherein at least one pharmaceutical composition is selected from the group consisting of aspirin, ezetimibe, simvastatin, atorvastatin free acid, atorvastatin calcium, rosuvastatin calcium, and mixtures thereof.

31. The process according to claim 28, wherein one of the pharmaceutical compositions is selected from the group consisting of ezetimibe/simvastatin, ezetimibe/atorvastatin calcium, ezetimibe/atorvastatin free acid, ezetimibe/rosuvastatin calcium, ezetimibe/simvastatin/aspirin, ezetimibe/atorvastatin calcium/aspirin, ezetimibe/atorvastatin free acid/aspirin, ezetimibe/rosuvastatin calcium/aspirin, and co-amorphous compositions comprising at least one statin and aspirin.

32. The process according to claim 28, wherein the co-amorphous pharmaceutical composition is selected from the group consisting of atorvastatin free acid/aspirin, atorvastatin calcium/aspirin, simvastatin/aspirin, and rosuvastatin calcium/aspirin.

* * * * *